United States Patent
Miyoshi et al.

(10) Patent No.: US 9,868,793 B2
(45) Date of Patent: Jan. 16, 2018

(54) CATIONIC GROUP-CONTAINING CELLULOSE ETHER

(71) Applicant: KAO CORPORATION, Tokyo (JP)

(72) Inventors: Eisuke Miyoshi, Wakayama (JP); Yumi Yamaguchi, Wakayama (JP); Naoyuki Yamazaki, Edogawa (JP); Ryosuke Fujii, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/899,039

(22) PCT Filed: Jan. 20, 2014

(86) PCT No.: PCT/JP2014/051596
§ 371 (c)(1),
(2) Date: Dec. 16, 2015

(87) PCT Pub. No.: WO2014/203548
PCT Pub. Date: Dec. 24, 2014

(65) Prior Publication Data
US 2016/0122441 A1   May 5, 2016

(30) Foreign Application Priority Data
Jun. 20, 2013  (JP) .................. 2013-129671

(51) Int. Cl.
*A61Q 5/02* (2006.01)
*A61Q 5/10* (2006.01)
*A61Q 5/12* (2006.01)
*A61Q 19/10* (2006.01)
*A61K 8/73* (2006.01)
*A61K 8/22* (2006.01)
*C08B 11/193* (2006.01)
*A61Q 5/04* (2006.01)
*A61Q 5/08* (2006.01)
*C08B 11/20* (2006.01)
*C08B 11/14* (2006.01)
*C08L 1/28* (2006.01)
*A61K 8/19* (2006.01)
*C08B 15/06* (2006.01)

(52) U.S. Cl.
CPC .......... *C08B 11/193* (2013.01); *A61K 8/19* (2013.01); *A61K 8/22* (2013.01); *A61K 8/731* (2013.01); *A61Q 5/02* (2013.01); *A61Q 5/04* (2013.01); *A61Q 5/08* (2013.01); *A61Q 5/12* (2013.01); *A61Q 19/10* (2013.01); *C08B 11/14* (2013.01); *C08B 11/20* (2013.01); *C08B 15/06* (2013.01); *C08L 1/288* (2013.01); *A61K 2800/5426* (2013.01)

(58) Field of Classification Search
None
See application file for complete search history.

(56) References Cited

U.S. PATENT DOCUMENTS

| 4,663,159 A * | 5/1987 | Brode, II ............... A61K 8/731 424/70.13 |
| 2007/0031362 A1 | 2/2007 | Kreeger et al. |
| 2013/0005957 A1 | 1/2013 | Kimura et al. |
| 2013/0296212 A1 | 11/2013 | Fujii et al. |
| 2015/0239993 A1 | 8/2015 | Miyoshi et al. |

FOREIGN PATENT DOCUMENTS

| DE | 33 01 667 A1 | 7/1984 | |
| DE | 3301667 A1 * | 7/1984 | ............. A61K 8/731 |
| EP | 0 189 935 A2 | 8/1986 | |
| EP | 2 500 012 A1 | 9/2012 | |
| EP | 2 659 879 A1 | 11/2013 | |
| JP | 61-181801 A | 8/1986 | |
| JP | 2006-52778 A | 12/2006 | |
| JP | 2012-140576 A | 7/2012 | |
| JP | 2014-131988 A | 7/2014 | |
| JP | 2014-131989 A | 7/2014 | |
| JP | 2014-131990 A | 7/2014 | |
| JP | 2014-131991 A | 7/2014 | |
| JP | 2014-193840 A | 10/2014 | |
| WO | WO 2005/000903 A1 | 1/2005 | |
| WO | WO 2012/091072 A1 | 7/2012 | |
| WO | WO 2013/137474 A1 | 9/2013 | |

OTHER PUBLICATIONS

International Search Report, issued in PCT/JP2014/051596, dated Apr. 29, 2014.

* cited by examiner

*Primary Examiner* — H. Sarah Park
(74) *Attorney, Agent, or Firm* — Birch, Stewart, Kolasch & Birch, LLP

(57) ABSTRACT

Provided is a cationic group-containing cellulose which, when incorporated in a hair wash composition, is able to give an excellent smootheness feeling and its sustained feeling in rinsing and give a good coat feeling, and which, when incorporated in a skin cleanser composition, is able to give an excellent moist feeling to the skin after washing and drying, and also provided are a surfactant composition, a hair wash composition, a skin cleanser composition, a hair conditioner composition and a hair treatment composition containing the cellulose ether. [1] A cationic group-containing cellulose ether, which has a main chain derived from an anhydroglucose, and in which the degree of substitution with a cationized oxyalkylene group per the anhydroglucose unit is from 0.01 to 1.0, the degree of substitution with a glycerol group is from 0.5 to 5.0, and the degree of substitution with a group that contains a branched hydrocarbon group having from 8 to 18 carbon atoms and has a specific structure is from 0.001 to 0.2; [2] a surfactant composition containing the cationic group-containing cellulose ether, a surfactant and water; [3] a hair wash composition, a skin cleanser composition, a hair conditioner composition and a hair treatment composition containing the cationic group-containing cellulose ether, a surfactant and water.

15 Claims, No Drawings

CATIONIC GROUP-CONTAINING CELLULOSE ETHER

TECHNICAL FIELD

The present invention relates to a cationic group-containing cellulose ether, and to a surfactant composition, a hair wash composition, a skin cleanser composition, a hair conditioner composition and a hair treatment composition containing the cellulose ether.

BACKGROUND ART

Hair is damaged by living environments (UV and heat from sunlight, drying), daily hair-care actions (hair washing, brushing, heat by drier) and chemical treatments (coloring, perming, etc.), and hair is kept in friction with each other while wetted, the surface thereof receives a great frictional force so that, while in hair washing, hair would generate a feeling of squeakiness and a feeling of entanglement. In a hair-care composition, in general, a cationic polymer such as typically a cationized hydroxyethyl cellulose is incorporated for the purpose of securing good feeling in finger-combability, smoothness and good slip retention in rinsing, in addition to securing the basic function thereof of washing away the dirt from hair.

For example, PTL 1 discloses hydrophobe-substituted water-soluble cationic polysaccharides, and in Examples therein, there are exemplified water-soluble cationic polysaccharides that are produced by reacting a cellulose-type starting substance with glycidol followed by quaternizing/alkylating it. The literature further says that aqueous solutions of the cationic polysaccharides enable powerful viscosity increase and foaming, and are therefore useful as hair-care compositions such as shampoos, hair conditioners, etc.

PTL 2 discloses a cellulose ether substituted with a substituent containing an alkyl or arylalkyl group with from 8 to 24 carbon atoms and a quaternary nitrogen-containing substituent, in a ratio of from 0.0003 to 0.08 mol per mol of the anhydroglucose unit therein, and a hair-care composition such as shampoo and the like containing the cellulose ether, further illustrating that the hair-care composition can better the combability of hair in wet and in dry.

PTL 3 illustrates a hair-care composition containing a cationized glycerolated cellulose in which the mean addition molar number of the cationic group is from 0.2 to 0.5 and the mean addition molar number of the glycerol group is from 1 to 2.58, saying that the composition can better the combability of hair in hair washing.

CITATION LIST

Patent Literature

[PTL 1] JP-A 61-181801
[PTL 2] JP-T 2006-527785
[PTL 3] German Patent 3301667

SUMMARY OF INVENTION

The present invention relates to the following [1] to [10].
[1] A cationic group-containing cellulose ether, which has a main chain derived from an anhydroglucose represented by the following general formula (1), and in which the degree of substitution with a cationized oxyalkylene group per the anhydroglucose unit is from 0.01 to 1.0, the degree of substitution with a glycerol group is from 0.5 to 5.0, and the degree of substitution with a group that contains a branched hydrocarbon group having from 8 to 18 carbon atoms and is represented by any of the following general formulae (6) to (8) is from 0.001 to 0.2:

[Chem. 1]

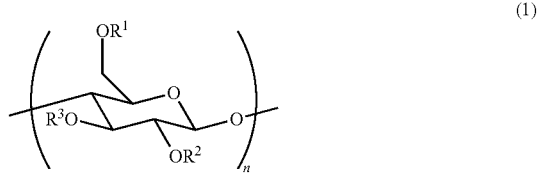

(In the formula, $R^1$, $R^2$ and $R^3$ each independently represent a substituent comprising at least one structural unit selected from the following formulae (2) to (8), or a hydrogen atom. n indicates a mean degree of polymerization of the anhydroglucose-derived main chain, and is a number of from 100 to 12000.)

[Chem. 2]

(In these formulae, the structural unit represented by the formula (2) or (3) is a cationized oxyalkylene group; the structural unit represented by the formula (4) or (5) is a glycerol group; and the structural unit represented by any of the formulae (6) to (8) is a group that contains a branched hydrocarbon group having from 8 to 18 carbon atoms. $R^4$ to $R^9$ each independently represent a linear or branched alkyl group having from 1 to 3 carbon atoms; $X^-$ and $Y^-$ each represent an anion; and r and s each indicate an integer of from 0 to 3. $R^{10}$ and $R^{11}$ each independently represent a branched hydrocarbon group having from 6 to 16 carbon atoms. $R^{12}$ represents a branched hydrocarbon group having from 8 to 18 carbon atoms; and p indicates an integer of 0 or 1. In the structural unit represented by any of the formulae (2) to (7), the oxygen atom bonds to a hydrogen atom or to the carbon atom of the above-mentioned structural unit.)

[2] A surfactant composition containing the cationic group-containing cellulose ether of the above [1], a surfactant and water.

[3] A hair wash composition containing the cationic group-containing cellulose ether of the above [1], a surfactant and water.

[4] A skin cleanser composition containing the cationic group-containing cellulose ether of the above [1], a surfactant and water.

[5] A hair conditioner composition containing the cationic group-containing cellulose ether of the above [1], a surfactant, an oily agent and water.

[6] A hair treatment composition containing the cationic group-containing cellulose ether of the above [1], as well as at least one treatment agent selected from a hair-coloring dye, an oxidizing agent, an alkali agent, and a keratin-reducing agent.

[7] A method of washing hair, including washing hair with the hair wash composition of the above [3], then rinsing and drying the hair.

[8] A method of cleansing a skin, including washing a skin with the skin cleanser composition of the above [4], then rinsing and drying the skin.

[9] A method of conditioning hair, including washing hair with a detergent, and then applying the hair conditioner composition of the above [5] to the hair.

[10] A method of treating hair, including treating hair with the hair treatment composition of the above [6], then rinsing and drying the hair.

DESCRIPTION OF EMBODIMENTS

The present invention relates to a cationic group-containing cellulose, which has a main chain derived from an anhydroglucose represented by the above-mentioned general formula (1), and in which the degree of substitution with a cationized oxyalkylene group per the anhydroglucose unit is from 0.01 to 1.0, the degree of substitution with a glycerol group is from 0.5 to 5.0, and the degree of substitution with a group that contains a branched hydrocarbon group having from 8 to 18 carbon atoms and is represented by any of the above-mentioned general formulae (6) to (8) is from 0.001 to 0.2, and to a surfactant composition, a hair wash composition, a skin cleanser composition, a hair conditioner composition and a hair treatment composition containing the cellulose ether.

The present invention relates to a cationic group-containing cellulose which, when incorporated in a hair wash composition, is able to give an excellent smoothness feeling and its sustained feeling in rinsing and give a good coated feeling, and also relates to a surfactant composition, a hair wash composition, a skin cleanser composition, a hair conditioner composition and a hair treatment composition containing the cellulose ether.

The present inventors have found that the specific cationic group-containing cellulose ether can solve the above-mentioned problems.

The cationic group-containing cellulose that is provided by the present invention can give, when incorporated in a hair wash composition, foam softness, good finger-combability of hair and hair softness in hair washing, can give an excellent smootheness feeling and its sustained feeling as well as softness and a coated feeling in rinsing, and can give a moist feeling and uniformity in drying.

The cationic group-containing cellulose that is provided by the present invention can give, when incorporated in a skin cleanser composition, an excellent moist feeling to the skin washed with the composition and dried.

The cationic group-containing cellulose that is provided by the present invention can give, when incorporated in a hair conditioner composition, an excellent presence in application of the composition to hair, can give an excellent smootheness feeling and its sustained feeling as well as softness in rinsing, and can give an excellent coated feeling after drying.

The cationic group-containing cellulose that is provided by the present invention can give, when incorporated in a hair treatment composition, a smootheness property, a good coated feeling and softness to hair in rinsing after treated with the composition, and can further give a smootheness property, a good coated feeling and softness to hair in rinsing after treated with a conditioner. Hereinafter these effects are referred to as the effects of the present invention.

Further according to the present invention, there are provided the hair wash composition excellent in foam softness, good finger-combability of hair and hair softness in hair washing, capable of giving an excellent smootheness feeling and its sustained feeling as well as softness and a coated feeling in rinsing, and capable of giving an excellent moist feeling and uniformity in drying; a skin cleanser composition capable of giving an excellent moist feeling to the skin washed with the composition and dried; a hair conditioner composition capable of giving an excellent presence in application of the composition to hair, capable of giving an excellent smootheness feeling and its sustained feeling as well as softness in rinsing, and capable of giving an excellent coated feeling after drying; and a hair treatment composition capable of giving a smootheness property, a good coat feeling and softness to hair in rinsing after treated with the composition, and can further capable of giving a smootheness property, a good coat feeling and softness to hair in rinsing after treated with a conditioner.

[Cationic Group-Containing Cellulose Ether]

The cationic group-containing cellulose ether (hereinafter this may be referred to as "CCE") of the present invention has a main chain derived from an anhydroglucose represented by the following general formula (1), in which the degree of substitution with a cationized oxyalkylene group per the anhydroglucose unit is from 0.01 to 1.0, the degree of substitution with a glycerol group is from 0.5 to 5.0, and the degree of substitution with a group that contains a branched hydrocarbon group having from 8 to 18 carbon atoms and is represented by any of the following general formulae (6) to (8) is from 0.001 to 0.2.

[Chem. 3]

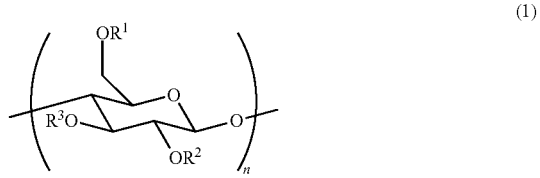

(1)

In the general formula (1), $R^1$, $R^2$ and $R^3$ each independently represent a substituent comprising at least one structural unit selected from the following formulae (2) to (8), or a hydrogen atom. n indicates a mean degree of polymerization of the anhydroglucose-derived main chain, and is a number of from 100 to 12000.

[Chem. 4]

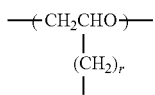   (2)

   (3)

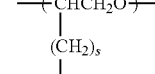   (4)

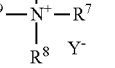   (5)

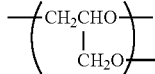   (6)

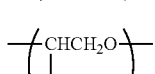   (7)

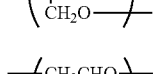   (8)

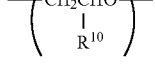

In these formulae, the structural unit represented by the formula (2) or (3) is a cationized oxyalkylene group; the structural unit represented by the formula (4) or (5) is a glycerol group; and the structural unit represented by any of the formulae (6) to (8) is a group that contains a branched hydrocarbon group having from 8 to 18 carbon atoms. $R^4$ to $R^9$ each independently represent a linear or branched alkyl group having from 1 to 3 carbon atoms; $X^-$ and $Y^-$ each represent an anion; and r and s each indicate an integer of from 0 to 3. $R^{10}$ and $R^{11}$ each independently represent a branched hydrocarbon group having from 6 to 16 carbon atoms. $R^{12}$ represents a branched hydrocarbon group having from 8 to 18 carbon atoms; and p indicates an integer of 0 or 1. In the structural unit represented by any of the formulae (2) to (7), the oxygen atom bonds to a hydrogen atom or to the carbon atom of the above-mentioned structural unit.

Though not clear, the reason why CCE of the present invention could exhibit the effects of the present invention would be considered as follows:

CCE of the present invention has a group that contains a branched hydrocarbon group having from 8 to 18 carbon atoms, and therefore, as compared with that of CCE having a linear hydrocarbon group-containing group, the hydrophobicity thereof could increase suitably. Consequently, CCE of the present invention that has such a branched hydrocarbon group-containing group could readily precipitate and could suitably adhere to hair and skin. As a result, when CCE of the present invention is incorporated in a hair wash composition, then the composition can provide an excellent smootheness feeling and its sustained feeling as well as softness and a coated feeling in rinsing, and can provide an excellent moist feeling and uniformity in drying; and when incorporated in a skin cleanser composition, then the composition can provide an excellent moist feeling to the skin washed with the composition and dried. When incorporated in a hair conditioner composition, then the composition can provide an excellent presence in application of the composition to hair, can provide an excellent smootheness feeling and softness in rinsing, and can provide an excellent coated feeling after drying; and when incorporated in a hair treatment composition, then the composition can provide excellent effects of giving a smootheness property, a good coated feeling and softness to hair in rinsing.

(Substituents $R^1$, $R^2$ and $R^3$)

In the above-mentioned general formula (1), when the substituent $R^1$ is a substituent comprising at least one structural unit selected from the formulae (2) to (8), then the substituent $R^1$ may be a substituent comprising multiple structural units selected from the formulae (2) to (8), or may be a substituent of only one structural unit selected from the formulae (2) to (8) of such that a hydrogen atom bonds to the oxygen atom of the structural unit.

When the substituent $R^1$ is a substituent comprising multiple structural units selected from the formulae (2) to (7), then the structural units bond to each other via the oxygen atom of one structural unit and the carbon atom of the other structural unit, and in the case, the oxygen atom not bonding to the carbon atom of the other structural unit, for example, the oxygen atom positioned at the terminal of the substituent bonds to a hydrogen atom.

The combination of the structural units is not specifically defined. Multiple structural units of one and the same formula selected from formulae (2) to (8) may bond together, or from 2 to 7 different types of structural units selected from the formulae (2) to (8) may bond together. In the general formula (1), in case where $R^1$ is a substituent having two or more different groups selected from a group containing any of a cationized oxyalkylene group, a glycerol group and a branched hydrocarbon group having from 8 to 18 carbon atoms, the bonding mode may be any of block bonding, random bonding, or alternate bonding. From the viewpoint of easiness in production, preferred is block bonding.

In case where the substituent $R^1$ is a substituent thatcontains at least one structural unit selected from the formulae (2) to (8), the terminal carbon atom bonds to the oxygen atom of the hydroxyl group in the anhydroglucose-derived main chain.

In case where the substituent $R^2$ is a substituent that comprises at least one structural unit selected from the formulae (2) to (8), the embodiments of the substituent are the same as the embodiments of the case where the above-mentioned substituent $R^1$ is a substituent that comprises at least one structural unit selected from the formulae (2) to (8).

In case where the substituent $R^3$ is a substituent that comprises at least one structural unit selected from the formulae (2) to (8), the embodiments of the substituent are the same as the embodiments of the case where the above-mentioned substituent $R^1$ is a substituent that comprises at least one structural unit selected from the formulae (2) to (8).

The substituents $R^1$, $R^2$ and $R^3$ are independent of each other, and may be the same or different.

Within a range not detracting from the effects of the present invention, the substituent $R^1$ may contain any other structural unit than the structural units of the formulae (2) to (8).

(Cationized Oxyalkylene Group Represented by Formula (2) or (3))

In the above-mentioned formula (2) or (3), $R^4$ to $R^9$ each independently represent a linear or branched alkyl group having from 1 to 3 carbon atoms. Specific examples of the group include a methyl group, an ethyl group, an n-propyl group and an isopropyl group. Of those, preferred are a methyl group and an ethyl group from the viewpoint of the availability of the reactants; and more preferred is a methyl group.

In the formulae (2) and (3), $X^-$ and $Y^-$ each represent an anion that is a counter ion to the quaternary ammonium ion. Not specifically defined, $X^-$ and $Y^-$ may be any anion, and as specific examples thereof, there may be mentioned at least one selected from an alkylsulfate ion having from 1 to 3 carbon atoms, a sulfate ion, a phosphate ion, a fatty acid ion having from 1 to 3 carbon atoms and a halide ion.

Of those, preferred are an alkylsulfate ion having from 1 to 3 carbon atoms, a sulfate ion and a halide ion, from the viewpoint of the easiness in production; and more preferred is a halide ion. As the halide ion, there may be mentioned at least one selected from a fluoride ion, a chloride ion, a bromide ion and an iodide ion. From the viewpoint of the water-solubility and the chemical stability of CCE, preferred are at least one selected from a chloride ion and a bromide ion; and more preferred is a chloride ion.

r and s each indicate an integer of from 0 to 3. From the viewpoint of the availability of the starting materials, r and s each are preferably 1.

(Group Containing Branched Hydrocarbon Group Having from 8 to 18 Carbon Atoms)

In the present invention, the group that contains a branched hydrocarbon group having from 8 to 18 carbon atoms is the structural unit represented by any of the above-mentioned general formulae (6) to (8). The carbon number of the branched hydrocarbon group is preferably from 8 to 16, more preferably from 8 to 14, even more preferably from 8 to 12, from the viewpoint of providing the effects of the present invention.

CCE of the present invention has the above-mentioned structural unit, and therefore, especially when incorporated in a hair wash composition, that CCE can give an excellent smoothness feeling and its sustained feeling as well as softness and, in addition thereto, an excellent coated feeling in rinsing. The coated feeling in rinsing as referred to in the present invention means that the surface of the hair has a feeling that is likely coated with a gel-like lubricant substance, and when the washed hair could have an excellent coated feeling, then the hair could enjoy more strongly the effects of the present invention, smoothness feeling and its sustained feeling.

In the formulae (6) and (7), $R^{10}$ and $R^{11}$ each independently represent a branched hydrocarbon group having from 6 to 16 carbon atoms, and accordingly, the formulae (6) and (7) have a branched hydrocarbon group having from 8 to 18 carbon atoms. Specific examples of $R^{10}$ and $R^{11}$ includes a branched alkyl group or branched alkenyl group having from 6 to 16 carbon atoms, for example, a 2-methylpentyl group, a 2-methylhexyl group, a 2-ethylpentyl group, a 3-ethylpentyl group, a 2-methylheptyl group, a 2-ethylhexyl group, a 3-ethylhexyl group, a 2-methyloctyl group, a 2-ethyloctyl group, an isodecyl group, an isotridecyl group, an isotetradecyl group, an isohexadecyl group, an isohexenyl group, an isooctenyl group, an isodecenyl group, an isotridecenyl group, an isotetradecenyl group, an isohexadecenyl group, etc. Of those, $R^{10}$ and $R^{11}$ each are preferably a branched alkyl or branched alkenyl group having from 6 to 14 carbon atoms, from the viewpoint of the water solubility of CCE and of the ability to provide the effects of the present invention, such as excellent smoothness feeling and its sustained feeling as well as excellent coated feeling in rinsing in use in a hair wash composition, and is more preferably a branched alkyl or branched alkenyl group having from 6 to 12 carbon atoms, even more preferably a branched alkyl group having from 6 to 12 carbon atoms.

In the above-mentioned formula (8), $R^{12}$ represents a branched hydrocarbon group having from 8 to 18 carbon atoms. From the viewpoint of the availability of the starting materials, the substituent is preferably a branched alkyl or branched alkenyl group having from 8 to 18 carbon atoms. $R^{12}$ includes, for example, a 2-methylheptyl group, a 2-ethylhexyl group, a 3-ethylhexyl group, a 2-methyloctyl group, a 2-ethyloctyl group, an isodecyl group, an isotridecyl group, an isotetradecyl group, an isohexadecyl group, an isooctadecyl group, an isooctenyl group, an isodecenyl group, an isotridecenyl group, an isotetradecenyl group, an isohexadecenyl group, an isooctadecenyl group, etc. Of those, $R^{12}$ is preferably a branched alkyl or branched alkenyl group having from 8 to 16 carbon atoms, from the viewpoint of the water solubility of CCE and of the ability to provide the effects of the present invention, such as excellent smoothness feeling and its sustained feeling as well as excellent coated feeling in rinsing in use in a hair wash composition, and is more preferably a branched alkyl or branched alkenyl group having from 8 to 14 carbon atoms, even more preferably a branched alkyl or branched alkenyl group having from 8 to 12 carbon atoms, still more preferably a branched alkyl group having from 8 to 12 carbon atoms. In addition, from the viewpoint of providing the effects of the present invention, such as excellent smoothness feeling and its sustained feeling as well as excellent coated feeling in use in a hair wash composition, $R^{12}$ is even more preferably a 2-ethylhexyl group or an isodecyl group, further more preferably a 2-ethylhexyl group.

From the viewpoint of the chemical stability of CCE, p is preferably 0.

Specifically, the formula (8) is preferably a 2-ethylhexyl group or an isodecyl group, and more preferably a 2-ethylhexyl group.

The group that contains a branched hydrocarbon group having from 8 to 18 carbon atoms is preferably a substituent that comprises the structural unit represented by the above-mentioned formula (8), especially from the viewpoint of providing the effects of the present invention, such as excellent smoothness feeling and its sustained feeling as well as excellent coated feeling in use in a hair wash composition.

The group that contains a branched hydrocarbon group having from 8 to 18 carbon atoms is preferably a branched alkyl group or branched alkenyl group having from 8 to 14 carbon atoms, from the viewpoint of providing the effects of the present invention, such as excellent smoothness feeling and its sustained feeling as well as excellent coated feeling in use in a hair wash composition, and is more preferably a branched alkyl group or branched alkenyl group having from 8 to 12 carbon atoms, even more preferably a branched alkyl group having from 8 to 12 carbon atoms, still more preferably a 2-ethylhexyl group or an isodecyl group, furthermore preferably a 2-ethylhexyl group.

(Degree of Substitution with Cationized Oxyalkylene Group)

In the present invention, the degree of substitution with a cationized oxyalkylene group (hereinafter this may be referred to as "MS(N+)") means a mean value of the number of the cationized oxyalkylene groups existing in the molecule of CCE per one anhydroglucose unit that constitutes the main chain of the molecule. MS(N+) may be measured and calculated according to the method described in the section of Examples to be given hereinunder.

MS(N+) in the cationized group-containing cellulose ether of the present invention is from 0.01 to 1.0. When MS(N+) falls within the range, then the present invention can provide the effects of the invention. From this viewpoint, MS(N+) is preferably at least 0.05, more preferably at least 0.08, even more preferably at least 0.11, still more preferably at least 0.16, further preferably at least 0.18, further more preferably at least 0.20, and is preferably at most 0.9, more preferably at most 0.7, even more preferably at most 0.5, still more preferably at most 0.35, further preferably at most 0.32, further more preferably at most 0.28, and still further more preferably at most 0.25.

(Degree of Substitution with Glycerol Group)

In the present invention, the degree of substitution with a glycerol group (hereinafter this may be referred to as "MS(Gly)") means a mean value of the number of the glycerol groups existing in the CCE molecule per one anhydroglucose unit that constitutes the main chain of the molecule. MS(Gly) may be measured and calculated according to the method described in the section of Examples to be given hereinunder.

MS(Gly) in the cationized group-containing cellulose ether of the present invention is from 0.5 to 5.0. When MS(Gly) falls within the range, then the present invention can provide the effects of the invention. In addition when MS(Gly) falls within the range, then the solubility of CCE in a surfactant composition is high, and therefore CCE could be readily incorporated in the composition. From these viewpoints, MS(Gly) is preferably at least 0.6, more preferably at least 0.7, even more preferably at least 1.2, still more preferably at least 1.6, further preferably at least 1.8, further more preferably at least 2.0. From the above-mentioned viewpoints and from the viewpoint of the cost of CCE of the present invention, MS(Gly) is preferably at most 4.0, more preferably at most 3.5, even more preferably at most 3.0, still more preferably at most 2.5, further preferably at most 2.4, further more preferably at most 2.3, and still further more preferably at most 2.2.

(Degree of Substitution with Group Containing Branched Hydrocarbon Group Having from 8 to 18 Carbon Atoms)

In the present invention, the degree of substitution with a group that contains a branched hydrocarbon group having from 8 to 18 carbon atoms (hereinafter this may be referred to as "MS(HC)") means a mean value of the number of the groups that contain a branched hydrocarbon group having from 8 to 18 carbon atoms and represented by any of the above-mentioned formulae (6) to (8) and exist in the CCE molecule per one anhydroglucose unit that constitutes the main chain of the molecule. MS(HC) may be measured and calculated according to the method described in the section of Examples to be given hereinunder.

MS(HC) in the cationized group-containing cellulose ether of the present invention is from 0.001 to 0.2. When MS(HC) falls within the range, then the present invention can provide the effects of the invention. From this viewpoint, MS(HC) is preferably at least 0.002, more preferably at least 0.005, even more preferably at least 0.01. From the above-mentioned viewpoint and from the viewpoint of the production cost of CCE of the present invention, MS(HC) is preferably at most 0.15, more preferably at most 0.10, and from the viewpoint of attaining the above-mentioned good smoothness feeling and its sustained feeling, MS(HC) is even more preferably at most 0.08, still more preferably at most 0.06, further preferably at most 0.05, further more preferably at most 0.04, and still further more preferably at most 0.03.

(Cation Charge Density)

Of CCE of the present invention, the cation charge density is preferably at least 0.05 mmol/g, more preferably at least 0.15 mmol/g, even more preferably at least 0.2 mmol/g from the viewpoint of attaining the effects of the present invention, and is even more preferably at least 0.3 mmol/g from the viewpoint of attaining the above-mentioned good smoothness feeling and its sustained feeling. From the same viewpoints, the cation charge density is preferably at most 2.0 mmol/g, more preferably at most 1.7 mmol/g, even more preferably at most 1.5 mmol/g; but from the viewpoint of attaining the above-mentioned good smoothness feeling and its sustained feeling, the cationic charge density is still more preferably at most 1.2 mmol/g, further preferably at most 1.0 mmol/g, further more preferably at most 0.9 mmol/g.

In the present invention, the cation charge density means the molar number of the cationic groups contained in 1 g of CCE, and is calculated according to the following math formula. Cation Charge Density (mmol/g)=nitrogen content (%)/14×10 (In the formula, the nitrogen content (%) is measured according to the method described in the section of Examples.)

(Mean Degree of Polymerization of CCE)

Starting from cellulose, CCE of the present invention can be obtained by introducing a cationized oxyalkylene group, a glycerol group and a group that contains a branched hydrocarbon group having from 8 to 18 carbon atoms, into the starting material. In case where the reaction of introducing these substituents is carried out in the presence of an inert gas such as nitrogen or the like, depolymerization of cellulose does not occur, and therefore the mean degree of polymerization of the starting cellulose could be considered to be the same as that of CCE. In the present invention, the mean degree of polymerization of cellulose that is the starting material for CCE is considered to be the same as the mean degree of polymerization of CCE. In the present invention, the mean degree of polymerization of cellulose means the viscosity-average mean degree of polymerization of cellulose, and concretely, it may be measured according to the method described in the section of Examples.

The mean degree of polymerization, n is at least 100, but preferably at least 200, more preferably at least 500, even more preferably at least 1000 from the viewpoint of securing the effects of the present invention. In addition, from that viewpoint and from the other viewpoint of the handleability of CCE of the present invention and that of the composition to which CCE has been incorporated, the mean degree of polymerization, n is at most 12000, but preferably at most 10000, more preferably at most 5000, even more preferably at most 2500.

(Viscosity of 1 Mass % Aqueous Solution)

From the viewpoint of securing the effects of the present invention, CCE of the present invention is preferably such that the viscosity of the 1 mass % aqueous solution thereof at 25° C. is at least 10 mPa·s, more preferably at least 20 mPa·s, even more preferably at least 50 mPa·s, still more preferably at least 100 mPa·s. On the other hand, from the viewpoint of improving the handleability of CCE of the present invention and that of the composition to which CCE has been incorporated, the viscosity of the 1 mass % aqueous solution of CCE at 25° C. is preferably at most 10000 mPa·s, more preferably at most 5000 mPa·s, even more preferably at most 3000 mPa·s, still more preferably at most 2000 mPa·s. The viscosity of the aqueous solution of CCE can be measured according to the method described in the section of Examples.

[Production of CCE]

CCE of the present invention may be produced by reacting cellulose with a cationizing agent that corresponds to the cationized oxyalkylene group in CCE of the present invention (hereinafter this may be simply referred to as "cationizing agent"), a glycerolating agent, and a reagent for introducing a group that contains a branched hydrocarbon group having from 8 to 18 carbon atoms (hereinafter this may be simply referred to as "hydrocarbon group-containing group). Here the order of the cationization reaction, the glycerolation reaction and the hydrocarbon group-containing group introduction reaction is not specifically defined, and any of these may be carried out first, or all of these may be carried out at a time, or may be repeated in any desired order. In case where the introduction of the cationized oxyalkylene group or the hydrocarbon group-containing group into cellulose is carried out first, then it is desirable that the glycerolation reaction is first carried out and thereafter the cationization reaction and the hydrocarbon group-containing introduction reaction are carried since the yield of glycerolation reaction based on the glycerolating agent may readily lower.

In general, cellulose has a high crystallinity, and is therefore poorly reactive. Accordingly, it is desirable that the crystallinity of cellulose is lowered before reaction, or that is, cellulose is preferably pre-treated for reactivity increase. For producing such CCE, for example, there are mentioned the following methods (i) to (iii).

Method (i):

This is an activation method of generally so-called alcelization of mercerization, in which cellulose is mixed with a large amount of water and with a large excessive amount of an alkali metal hydroxide to give an alkali cellulose, and thereafter this is reacted with a glycerolating agent, a cationizing agent, and a hydrocarbon group-containing group-introducing agent.

Method (ii):

Using a solvent capable of dissolving cellulose, such as tetrabutylammonium fluoride-containing dimethyl sulfoxide, paraformaldehyde-containing dimethyl sulfoxide, lithium chloride-containing dimethylacetamide or the like, as in "Cellulose Dictionary", edited by the Cellulose Society of Japan, published by Asakura Publishing, "Macromol. Chem. Phys. 201", 627-631 (2000) or the like, the starting cellulose is dissolved therein, and thereafter the starting cellulose is reacted with a glycerolating agent, a cationizing agent, and a hydrocarbon group-containing group-introducing agent.

Method (iii):

Any excess alkali or specific solvent for dissolving cellulose, as in the above-mentioned methods (i) and (ii), are not used. Apowdery or floc-like starting cellulose is reacted with a glycerolating agent, a cationizing agent and a hydrocarbon group-containing group-introducing agent in the presence of an alkali.

The cellulose, the glycerolating agent, the cationizing agent and the hydrocarbon group-containing group-introducing agent that are used as the materials for producing CCE of the present invention, as well as the activation methods and others are described below.

<Starting Cellulose>

Cellulose that is used as the starting material for CCE of the present invention (hereinafter this may be referred to as "starting cellulose") is not specifically defined in point of the type thereof; but from the viewpoint of the cellulose purity, the degree of polymerization and the availability, preferred are various types of wood chips; pulps such as wood pulp produced from wood, cotton linter pulp obtained from fibers around cotton seeds, etc.

From the viewpoint of securing the effects of the present invention, the mean degree of polymerization of the starting material is preferably at least 100, more preferably at least 200, even more preferably at least 500, still more preferably at least 1000; and from the above-mentioned viewpoint and from the other viewpoint of the handleability of CCE of the present invention and that of the composition in which CCE has been incorporated, the mean degree of polymerization is preferably at most 12000, more preferably at most 10000, even more preferably at most 5000, still more preferably at most 2500.

The mean degree of polymerization of the starting cellulose means the viscosity-average mean degree of polymerization thereof measured according to the copper-ammonia method described in the section of Examples or the like.

The shape of the starting cellulose is not specifically defined so far as not interfering with the introduction thereof into a production apparatus, but from the viewpoint of handleability thereof, preferred is use of sheet-like, pellet-like, chip-like, floc-like or powder one. More preferred is a chip-like, floc-like or powdery cellulose, and even more preferred is a floc-like or powdery cellulose. A chip-like cellulose can be prepared, for example, by cutting a starting cellulose. A floc-like or powdery cellulose can be prepared, for example, by cutting a starting cellulose, then optionally drying it, and thereafter grinding it.

(Cutting Treatment)

Depending on the type and the shape of the starting cellulose, cutting treatment is preferably carried out as the pretreatment prior to grinding treatment. The method of cutting a starting cellulose may be suitably selected depending on the type and the shape of the starting cellulose. For example, there may be mentioned a method of using one or more different types of cutting machines selected from a shredder, a slitter cutter and a rotary cutter.

In case where a sheet-like starting cellulose is used here, preferably used is a shredder or a slitter cutter as the cutting machine; and from the viewpoint of the producibility, more preferred is use of a slitter cutter.

A slitter cutter is a cutting machine that cuts a sheet longitudinally in the machine direction parallel to the lengthwise direction of the sheet with a roll cutter, thereby giving thin and long strips, in which the thus-cut slips are thereafter further cut laterally into short strips with a fixed blade and a rotary blade. Using such a slitter cutter, the starting cellulose can be chopped into fine pellets. As the slitter cutter, preferably used is a sheet pelletizer by Horai. Using the apparatus, a sheet-like starting cellulose can be cut into pellets of from about 1 to 20 mm square.

In case where wood materials such as timber from forest thinning, pruned branches, scrap wood in building or the like, or any other cellulose materials than sheet-like ones are cut, preferred is use of a rotary cutter. A rotary cutter comprises a rotary blade and a screen. Using such a rotary cutter, a starting cellulose that has been cut with the rotary blade into a size not larger than the screen mesh can be readily obtained. If desired, a fixed blade may be arranged in the cutter, in which materials may be cut with both the rotary blade and the fixed blade.

In case where a rotary cutter is used, the size of the roughly cut material to be obtained may be controlled by changing the screen mesh.

The size of the starting cellulose to be obtained after the cutting treatment is preferably at least 1 mm square, more preferably at least 2 mm square from the viewpoint of the producibility; but from the viewpoint of reducing the load in grinding in the subsequent grinding treatment and from the viewpoint of more efficiently carrying out the subsequent drying treatment to be mentioned below, the size is preferably at most 70 mm square, more preferably at most 50 mm square.

(Drying Treatment)

The water content of the starting cellulose to be ground is preferably smaller. The lower limit of the water content during grinding treatment could be 0% by mass relative to the starting cellulose; however, from the viewpoint of the producibility, the water content is preferably at least 0.01% by mass, more preferably at least 0.05% by mass, even more preferably at least 0.1% by mass. On the other hand, from the viewpoint of the starting cellulose grinding efficiency, the water content is preferably at most 10% by mass, more preferably at most 7% by mass, even more preferably at most 4% by mass, still more preferably at most 2% by mass.

In general, a starting cellulose of commercially-available pulps, as well as paper materials, wood materials, plant stems and leaves, plant shells and the like contains water in an amount of more than 5% by mass, and generally contains water in an amount of from 5 to 30% by mass. Accordingly, by drying such a starting cellulose, preferably a starting cellulose obtained after cutting treatment, it is desirable to control the water content of the starting cellulose for use herein.

As the drying method, any known drying means may be suitably selected, and for example, there may be mentioned a hot air heat-receiving drying method, a conductive heat-receiving drying method, a dehumidified air drying method, a cold air drying method, a microwave drying method, an IR drying method, a solar drying method, a vacuum drying method, a freeze drying method, etc.

In the above-mentioned drying method, any known drier may be suitably selected and used. For example, various driers usable herein are described in "Introduction to Powder Technology" (edited by the Society of Powder Technology, Japan, published by the Information Center of Particle Technology, Japan, 1995), page 176.

One alone or two or more different types of such drying methods and driers may be used here either singly or as combined. The drying treatment may be in any mode of batch treatment or continuous treatment, but from the viewpoint of the producibility, continuous treatment is preferred.

As a continuous drier, preferred is a conductive heat-receiving, horizontal stirring drier from the viewpoint of the heat conductivity efficiency. Further, from the viewpoint that fine powder hardly forms and from the viewpoint of the stability in continuous discharge, also preferred is a double-screw horizontal stirring drier. As such a double-screw horizontal stirring drier, Nara Machinery's Double-Screw Paddle Drier is preferably used here.

The temperature in the drying treatment could not be indiscriminately defined as varying depending on the drying means, the drying time and others, but is preferably not lower than 10° C., more preferably not lower than 25° C., even more preferably not lower than 50° C. Also preferably, the temperature is not higher than 250° C., more preferably not higher than 180° C., even more preferably not higher than 150° C. The treatment time is preferably nor shorter than 0.01 hours, more preferably not shorter than 0.02 hours, and is preferably not longer than 2 hours, more preferably not longer than 1 hour. If desired, the drying treatment may be carried out under reduced pressure, and the pressure is preferably not lower than 1 kPa, more preferably not lower than 50 kPa, and is preferably not higher than 120 kPa, more preferably not higher than 105 kPa.

(Grinding Treatment)

The grinder for use for grinding treatment is not specifically defined, and may be any and every device capable of powdering or flocculating the starting cellulose.

Specific examples of the grinder include a roll mill such as a high-pressure compression mill, a roll tumbling mill, etc.; a vertical roller mill such as a ring roller mill, a roller-race mill, a ball-race mill, etc.; a vessel-driving medium mill such as a tumbling ball mill, a shaking ball mill, a shaking rod mill, a shaking tube mill, a planetary ball mill, a centrifugal fluidization mill, etc.; a medium stirring mill such as a tower grinder, a stirring tank mill, a circulation tank mill, an annular mill, etc.; a consolidation shear mill such as a fast centrifugal roller mill, an angmill, etc.; as well as a mortar, a stone mill, a mass-colloider, a fret mill, an edge runner mill, a knife mill, a pin mill, a cutter mill, etc.

Of those, preferred are a vessel driving medium mill and a medium stirring mill, from the viewpoint of the cellulose grinding efficiency, the producibility and the efficiency of the subsequent glycerolation or the like introducing agent efficiency; and more preferred is a vessel driving medium mill. Further preferred is a shaking mill such as a shaking ball mill, a shaking rod mill or a shaking tube mill; and still further preferred is a shaking rod mill. The grinding method may be in any mode of batch treatment or continuous treatment.

The material of the apparatus and the material of the media to be used for the grinding treatment are not specifically defined, including, for example, iron, stainless, alumina, zirconia, silicon carbide, silicon nitride, glass, etc. From the viewpoint of the starting cellulose grinding efficiency, preferred are iron, stainless, zirconia, silicon carbide and silicon nitride; and from the viewpoint of the industrial applicability, especially preferred are iron and stainless.

In case where the apparatus to be used is a shaking mill and the media are rods, the diameter of the rods is preferably not less than 0.1 mm and more preferably not less than 0.5 mm from the viewpoint of the starting cellulose grinding efficiency; and from the same viewpoint, the diameter is preferably not more than 100 mm, more preferably not more than 50 mm.

A preferred range of the rods packing ratio varies depending on the type of the shaking mill. From the viewpoint of the cellulose grinding efficiency and the producibility, the ratio is preferably not less than 10%, more preferably not less than 15%, even more preferably not less than 50%, and is preferably not more than 97%, more preferably not more than 95%.

When the packing ratio falls within the range, then the contact frequency between cellulose and rods could increase and the grinding efficiency could be improved not interfering with the movement of the media. Here the packing ratio means the volume of the rods relative to the capacity of the stirring site of the shaking mill.

The temperature during the grinding treatment is not specifically defined. From the viewpoint of preventing cellulose decomposition and from the viewpoint of the operation cost, the temperature is preferably not lower than −100° C., more preferably not lower than 0° C., even more preferably not lower than 10° C., and is preferably not higher than 200° C., more preferably not higher than 100° C., even more preferably not higher than 70° C.

The grinding treatment time may be suitably controlled so that the starting cellulose could be powdered or flocculated. The grinding treatment time may vary depending on the grinder to be used, the necessary energy amount and others, but may be generally from 10 seconds to 12 hours. From the viewpoint of sufficiently powdering or flocculating the starting cellulose, the grinding treatment time is preferably not shorter than 15 seconds, more preferably not shorter than 1 minutes; and from the viewpoint of the producibility, the grinding treatment time is preferably not longer than 3 hours, more preferably not longer than 1 hour, even more preferably not longer than 20 minutes.

<Glycerolating Agent>

The glycerolating agent for use in producing CCE of the present invention may be at least one selected from glycidol; 3-halo-1,2-propanediols such as 3-chloro-1,2-propanediol, 3-bromo-1,2-propanediol, etc.; glycerin; glycerin carbonates. Of those, preferred is glycidol from the viewpoint of the property thereof not producing any salt and from the viewpoint of the reactivity thereof.

One alone or two or more different types of such glycerolating agents may be used here either singly or as combined. The amount of the glycerolating agent to be used may be suitably selected in consideration of the desired MS (Gly). From the viewpoint of the solubility in water of CCE and of the object of securing the effects of the present invention, the amount is preferably at least 0.2 mols relative to one mol of the anhydroglucose unit (hereinafter this may be referred to as "AGU") in the starting cellulose, more preferably at least 1 mol, even more preferably at least 3 mols, still more preferably at least 4 mols; and from the above viewpoint and additionally from the viewpoint of the production cost, the amount is preferably at most 60 mols, more preferably at most 50 mols, even more preferably at most 45 mols, still more preferably at most 40 mols.

Regarding the mode of addition thereof, the glycerolating agent may be added to the system all at a time, or intermittently or continuously. From the viewpoint of increasing the reaction yield of the starting cellulose with the glycerolating agent, continuous addition is preferred.

<Cationizing Agent>

The cationizing agent for use in producing CCE of the present invention includes compounds represented by the following general formula (9) or (10), etc.

[Chem. 5]

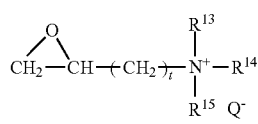
(9)

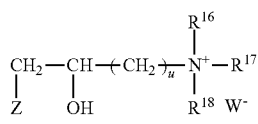
(10)

In the general formulae (9) and (10), $R^{13}$ to $R^{18}$ and preferred embodiments thereof are the same as $R^4$ to $R^9$ in the above-mentioned general formulae (2) and (3). t and u and preferred embodiments thereof are also the same as r in the formula (2) and s in the formula (3). $Q^-$ and $W^-$ and preferred embodiments thereof are the same as $X^-$ in the formula (2) and $Y^-$ in the formula (3). Z represents a halogen atom. $R^{13}$ to $R^{18}$ may be the same or different.

Specific examples of the compounds represented by the above-mentioned general formulae (9) and (10) include glycidyltrimethylammonium, glycidyltriethylammonium and glycidyltripropylammonium chlorides, bromides and iodides; 3-chloro-2-hydroxypropyltrimethylammonium, 3-chloro-2-hydroxypropyltriethylammonium and 3-chloro-2-hydroxytripropylammonium chlorides; 3-bromo-2-hydroxypropyltrimethylammonium, 3-bromo-2-hydroxypropyltriethylammonium and 3-bromo-2-hydroxypropyltripropylammonium bromides; 3-iodo-2-hydroxypropyltrimethylammonium, 3-iodo-2-hydroxypropyltriethylammonium and 3-iodo-2-hydroxypropyltripropylammonium iodides.

Of those, from the viewpoint of the availability of the starting materials and of the chemical stability of the compound, preferred is at least one selected from glycidyltrimethylammonium or glycidyltriethylammonium chlorides or bromides; 3-chloro-2-hydroxypropyltrimethylammonium or 3-chloro-2-hydroxypropyltriethylammonium chlorides; and 3-bromo-2-hydroxypropyltrimethylammonium or 3-bromo-2-hydroxypropyltriethylammonium bromides. More preferred is at least one selected from glycidyltrimethylammonium chloride and 3-chloro-2-hydroxypropyltrimethylammonium chloride; and even more preferred is glycidyltrimethylammonium chloride.

One alone or two or more different types of these cationizing agents may be used here either singly or as combined.

The amount of the cationizing agent to be used may be suitably selected in consideration of the desired MS(N+) and the reaction yield. From the viewpoint of the solubility in water of CCE and of the object of securing the effects of the present invention, the amount is preferably at least 0.01 mols relative to one mol of AGU in the starting cellulose, more preferably at least 0.03 mols, even more preferably at least 0.05 mols, still more preferably at least 0.1 mols; and from the above viewpoint and the viewpoint of the CCE production cost, the amount is preferably at most 30 mols, more preferably at most 25 mols, even more preferably at most 10 mols.

Regarding the mode of addition thereof, the cationizing agent may be added to the system all at a time, or intermittently or continuously.

<Hydrocarbon Group-Containing Group-Introducing Agent>

The hydrocarbon group-containing group-introducing agent for use in producing CCE of the present invention may be any one capable of introducing the structural unit represented by any of the above-mentioned general formulae (6) to (8).

The introducing agent for introducing the structural unit represented by the general formula (6) or (7) includes compounds represented by the following general formula (11) or (12), etc.

[Chem. 6]

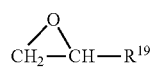
(11)

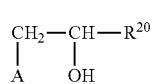
(12)

In the general formulae (11) and (12), $R^{19}$ and $R^{20}$ and preferred embodiments thereof are the same as $R^{10}$ in the above-mentioned general formula (6) and $R^{11}$ in the general formula (7). A represents a halogen atom.

Specific examples of the compounds represented by the general formula (11) include 1,2-epoxyalkanes and 1,2-epoxyalkanes having a branched hydrocarbon group and having from 8 to 18 carbon atoms, such as 1,2-epoxy-5-methylheptane, 1,2-epoxy-6-methylheptane, etc. Specific examples of the compounds represented by the general formula (12) include 1-halo-2-alkanols and 1-halo-2-alkenols having a branched hydrocarbon group with from 8 to 18 carbon atoms, such as 1-chloro-5-methylheptan-2-ol, 1-chloro-6-methylheptan-2-ol, etc.

Of those, preferred are the compounds represented by the general formula (11) from the viewpoint of no salt generation during reaction, and from the viewpoint of the availability of the starting materials and the chemical stability of the compounds.

One alone or two or more different types of those compounds may be used here either singly or as combined.

The introducing agent capable of introducing the structural unit represented by the general formula (8) includes compounds represented by the following formula (13), (14) or (15), etc.

[Chem. 7]

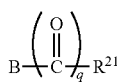  (13)

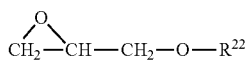  (14)

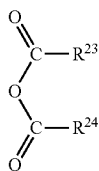  (15)

In the general formulae (13), (14) and (15), $R^{21}$, $R^{22}$, $R^{23}$ and $R^{24}$ and preferred embodiments thereof are the same as $R^{12}$ in the above-mentioned general formula (8). q and preferred embodiments thereof are the same as p in the general formula (8). B represents a halogen atom. In the general formula (15), $R^{23}$ and $R^{24}$ may be the same or different, but are preferably the same. When the compound represented by the general formula (14) is used, a glycerol group represented by the general formula (4) or (5) and a structural unit represented by the general formula (8) (in which p is 0) may be introduced at the same time.

Specific examples of the compounds represented by the general formula (13) include halides having a branched hydrocarbon group with from 8 to 18 carbon atoms, such as 2-methylheptyl halides, 2-ethylhexyl halides, 3-ethylhexyl halides, 2-methyloctyl halides, 2-ethyloctyl halides, isodecyl halides, isotridecyl halides, isotetradecyl halides, isohexadecyl halides, isooctadecyl halides, isooctenyl halides, isodecenyl halides, isotridecenyl halides, isotetradecenyl halides, isohexadecenyl halides, isooctadecenyl halides, etc.; carboxylic acid halides having a branched hydrocarbon group with from 8 to 18 carbon atoms, etc.

Specific examples of the compounds represented by the general formula (14) include glycidyl ethers having a branched alkyl group with from 8 to 18 carbon atoms, such as 2-methylheptyl glycidyl ether, 2-ethylhexyl glycidyl ether, 3-ethylhexyl glycidyl ether, 2-methyloctyl glycidyl ether, 2-ethyloctyl glycidyl ether, isodecyl glycidyl ether, isotridecyl glycidyl ether, isotetradecyl glycidyl ether, isohexadecyl glycidyl ether, isooctadecyl glycidyl ether, etc.; glycidyl ethers having a branched alkenyl group with from 8 to 18 carbon atoms, such as isooctenyl glycidyl ether, isodecenyl glycidyl ether, isotridecenyl glycidyl ether, isotetradecenyl glycidyl ether, isohexadecenyl glycidyl ether, isooctadecenyl glycidyl ether, etc.

Specific examples of the compounds represented by the general formula (15) include the above-mentioned carboxylic acid anhydrides having a branched hydrocarbon group with from 8 to 18 carbon atoms, etc.

Of those, preferred are the compounds represented by the general formula (14), from the viewpoint of the availability of the starting materials and of the chemical stability of CCE; but from the viewpoint of the solubility in water of CCE and the object of securing the effects of the present invention, preferred are glycidyl ethers having a branched alkyl group with from 8 to 18 carbon atoms, more preferred are glycidyl ethers having a branched alkyl group with from 8 to 14 carbon atoms, even more preferred are glycidyl ethers having a branched alkyl group with from 8 to 12 carbon atoms, still more preferred is at least one selected from 2-ethylhexyl glycidyl ether and isodecyl glycidyl ether, and further more preferred is 2-ethylhexyl glycidyl ether.

One alone or two or more different types of these may be used here either singly or as combined.

The amount of the hydrocarbon group-containing group-introducing agent to be used here may be suitably selected in consideration of the desired MS(HC) and the reaction yield. From the viewpoint of the solubility in water of CCE and of the object of securing the effects of the present invention, the amount is preferably at least 0.01 mols relative to 1 mol of AGU in the starting cellulose, more preferably at least 0.03 mols; and from the above viewpoint and from the viewpoint of the production cost of CCE, the amount is preferably at most 5 mols, more preferably at most 3 mols, even more preferably at most 1 mol, still more preferably at most 0.5 mols, further more preferably at most 0.2 mols.

Regarding the mode of addition thereof, the hydrocarbon group-containing group-introducing agent may be added to the system all at a time, or intermittently or continuously.

<Alkali Compound>

CCE of the present invention can be obtained by reacting a powdery cellulose or a flock-like cellulose that has been prepared preferably through the above-mentioned grinding treatment, with the above-mentioned glycerolating agent, the cationizing agent and the hydrocarbon group-containing group-introducing agent, thereby attaining the glycerolation reaction, the cationization reaction and the hydrocarbon group-containing group introduction reaction. These reactions are all carried out in the presence of an alkali compound. The alkali compound for use in these reactions includes alkali metal hydroxides such as sodium hydroxide, potassium hydroxide, lithium hydroxide, etc.; alkaline earth metal hydroxides such as magnesium hydroxide, calcium hydroxide, etc.; tertiary amines such as trimethylamine, triethylamine, etc. Of those, from the viewpoint of the reaction speed in the glycerolation reaction, the cationization reaction and the hydrocarbon group-containing group introduction reaction, preferred are alkali metal hydroxides and alkaline earth metal hydroxides, more preferred are alkali metal hydroxides, and even more preferred are sodium hydroxide and potassium hydroxide. One alone or two or more different types of these alkali metal compounds may be used here either singly or as combined.

Regarding the mode of addition thereof, the alkali compound may be added to the system all at a time, or intermittently or continuously. The alkali compound may be added thereto in a solid state or may be added as an aqueous solution thereof.

Except in the case of the above-mentioned method (i), the amount of the alkali compound to be used in the glycerolation reaction is, when the alkali compound is a monohydric basic compound such as an alkali metal hydroxide or a compound having one tertiary amine in the molecule or the like, preferably at least 0.2 mols relative to 1 mol of AGU in the starting cellulose, from the viewpoint of improving the cellulose reactivity and of the reaction selectivity of the glycerolation reaction agent, more preferably at least 0.7 mols, even more preferably at least 0.8 mols; and from the same viewpoint, the amount is preferably at most 2.0 mols, more preferably at most 1.3 mols, even more preferably at most 1.2 mols.

Except in the case of the above-mentioned method (i), the amount of the alkali compound to be used in the cationization reaction and in the hydrocarbon group-containing group introduction reaction is, when the alkali compound is a monohydric basic compound, preferably at least 0.01 mols relative to 1 mol of AGU in the starting cellulose, from the viewpoint of the reaction selectivity of the reactant, more preferably at least 0.05 mols, even more preferably at least 0.1 mols; and from the same viewpoint, the amount is preferably at most 1.0 mol, more preferably at most 0.8 mols, even more preferably at most 0.5 mols.

The preferred amount of the alkali compound to be used in the case where the cationization reaction and the hydrocarbon group-containing group introduction reaction are carried out simultaneously is the same as the amount of the alkali compound to be used in the case where the cationization reaction and the hydrocarbon group-containing group introduction reaction are carried out separately.

In case where the alkali compound for use in the glycerolation reaction, the cationization reaction or the hydrocarbon group-containing group introduction reaction is a polyhydric base such as an alkaline earth hydroxide or the like, the preferred range of the amount of the alkali compound to be used falls within the range obtained by dividing the range of the preferred amount of the alkali compound to be used in each reaction by the valence of the polyhydric base. For example, when the alkali compound to be used is calcium hydroxide (dihydric base), then the amount of calcium hydroxide to be used in the glycerolation reaction is, except in the case of the method (i), preferably at least 0.1 mols relative to 1 mol of AGU in the starting cellulose, from the viewpoint of improving the cellulose reaction activity and of the reaction selectivity of the glycerolation reaction agent, more preferably at least 0.35 mols, even more preferably at least 0.4 mols; and from the same viewpoint, the amount is preferably at most 1.0 mol, more preferably at most 0.65 mols, even more preferably at most 0.6 mols.

CCE of the present invention can be obtained by reacting a powdery cellulose or a flock-like cellulose that has been prepared preferably through the above-mentioned grinding treatment, with the above-mentioned glycerolating agent, the cationizing agent and the hydrocarbon group-containing group-introducing agent, thereby attaining the glycerolation reaction, the cationization reaction and the hydrocarbon group-containing group introduction reaction. Hereinunder the glycerolation reaction, the cationization reaction and the hydrocarbon group-containing group introduction reaction may be referred to as a collective term "reaction in CCE production".

In each reaction in CCE production, the mode of addition of the glycerolating agent, the cationizing agent and the hydrocarbon group-containing group-introducing agent is not specifically defined. In case where the glycerolating agent, the cationizing agent and the hydrocarbon group-containing group-introducing agent each are in a liquid state, they may be used directly as they are, or may be diluted with a good solvent for the glycerolating agent or the cationizing agent, such as water, a nonaqueous solvent or the like, and may be used in the form of a diluted solution thereof.

The nonaqueous solvent to be used for dilution may be any one to be used generally in the art, including secondary or tertiary lower alcohols having from 3 to 4 carbon atoms, such as isopropanol, tert-butanol, etc.; ketones having from 3 to 6 carbon atoms such as acetone, methyl ethyl ketone, methyl isobutyl ketone, etc.; ethers such as tetrahydrofuran, 1,4-dioxane, ethylene glycol dimethyl ether, diethylene glycol dimethyl ether, etc.; other aprotic polar solvents such as dimethylsulfoxide, etc.

Each reaction in CCE production in the above-mentioned method (ii), a solvent capable of dissolving cellulose is used and the starting cellulose is dissolved therein, and also in the methods (i) and (iii), the reaction may be carried out in the presence of a nonaqueous solvent from the viewpoint of the reaction yield with the glycerolating agent, the cationizing agent and the hydrocarbon group-containing group-introducing agent. As the nonaqueous solvent, usable is any of the above-mentioned nonaqueous solvents.

The amount of the nonaqueous solvent to be used is preferably at least 100% by mass relative to the starting cellulose, from the viewpoint of the addition effect of the nonaqueous solvent, more preferably at least 1000% by mass, even more preferably at least 5000% by mass, but from the viewpoint of the producibility and the reaction yield, the amount is preferably at most 100000% by mass, more preferably at most 50000% by mass, even more preferably at most 20000% by mass.

As the apparatus for use for each reaction in CCE production mentioned above, there are mentioned mixing machines, for example, a mixer such as a stirrable Ledige mixer, etc.; and a so-called kneader for use for kneading powders, high-viscosity substances, resins, etc.

The temperature in each reaction in CCE production is preferably not lower than 0° C., from the viewpoint of the reaction speed, more preferably not lower than 20° C., even more preferably not lower than 30° C. From the viewpoint of preventing decomposition of the glycerolating agent, the cationizing agent and the hydrocarbon group-containing group-introducing agent used, the temperature is preferably nit higher than 200° C., more preferably not higher than 100° C., even more preferably not higher than 80° C.

The reaction time for each reaction in CCE production may be suitably controlled, depending on the reaction speed of the glycerolating agent, the cationizing agent and the hydrocarbon group-containing group-introducing agent used. In general, the reaction time is from 0.1 hours to 72 hours, but from the viewpoint of the reaction yield and the producibility, the time is preferably not shorter than 0.2 hours, more preferably not shorter than 0.5 hours, even more preferably not shorter than 1 hour, still more preferably not shorter than 3 hours. Also preferably, the time is not longer than 36 hours, more preferably not longer than 18 hours, even more preferably not longer than 12 hours, still more preferably not longer than 8 hours.

Each reaction in CCE production may be carried out, if desired, in an inert gas atmosphere such as nitrogen or the like, from the viewpoint of preventing discoloration of the products and preventing reduction in the molecular weight of the anhydroglucose-derived main chain in the products.

After the reaction, the alkali compound may be neutralized with an acid. In case where the glycerolation reaction, the cationization reaction and the hydrocarbon group-containing group introduction reaction are carried out separately, the compound may be neutralized in each reaction; however, from the viewpoint of preventing the formation of neutralized salts, it is desirable that the neutralization is carried out after all the reactions. As the acid, usable is an inorganic acid such as sulfuric acid, hydrochloric acid, phosphoric acid, etc., or an organic acid such as acetic acid, lactic acid, etc.

Before use, CCE obtained after all those reactions in CCE production may be, if desired, fractionated through filtration or the like, or may be washed with hot water, water-containing isopropyl alcohol, water-containing acetone or the like solvent to thereby remove the unreacted cationizing agent, glycerolating agent, hydrocarbon group-containing group-introducing agent, as well as side products derived from those reactants, and salts formed as side products through neutralization or the like. In addition, as the purification methods, also usable are ordinary purification methods of reprecipitating purification, centrifugation, dialysis, etc.

CCE of the present invention may be formulated in a surfactant composition containing CCE of the present invention, a surfactant and water, and may be applied to a hair wash composition, a skin cleanser composition, a hair conditioner composition or a hair treatment composition. When CCE of the present invention is applied to a hair wash composition, then the hair wash composition can give foam softness, good finger-combability of hair and hair softness in hair washing, can give an excellent smoothness feeling and its sustained feeling as well as softness and a coated feeling in rinsing, and can give a moist feeling and uniformity in drying. When CCE of the present invention is applied to a skin cleanser composition, the skin cleanser composition can give an excellent moist feeling to the skin washed with the composition and dried. When CCE of the present invention is applied to a hair conditioner composition, the hair conditioner composition can give an excellent presence in application of the composition to hair, can give an excellent smoothness feeling and its sustained feeling as well as softness in rinsing, and can give an excellent coated feeling after drying.

In the present invention, the coated feeling after drying means that the hair coated with the conditioning component could take an almost healthy hair feeling with no damage.

In addition, CCE of the present invention is applicable to various hair treatment compositions such as a hair color composition, a hair bleach composition, a perm wave composition, a straight perm composition, a sustainable hair styling composition, a hair relaxer composition, etc. When CCE of the present invention is applied to such a hair treatment composition, the hair treatment composition can give a smoothness property, a good coated feeling and softness to hair in rinsing after treated with the composition, and can further give a smoothness property, a good coated feeling and softness to hair in rinsing after treated with a conditioner.

[Surfactant Composition]

The surfactant composition of the present invention comprises CCE of the present invention, a surfactant and water.

<CCE>

The CCE content in the surfactant composition of the present invention is preferably at least 0.01% by mass, from the viewpoint of providing the effects of the present invention, more preferably at least 0.05% by mass. On the other hand, from the viewpoint of the handleability of the surfactant composition, the content is preferably at most 10% by mass, more preferably at most 5% by mass, even more preferably at most 1% by mass. From these viewpoints, the CCE content in the surfactant composition is preferably from 0.01 to 10% by mass, more preferably from 0.05 to 5% by mass, even more preferably from 0.05 to 1% by mass.

From the viewpoint of providing the effects of the present invention, CCE contained in the surfactant of the present invention preferably has MS(N+) of from 0.03 to 0.9, MS(Gly) of from 0.5 to 3.0 and MS(HC) of from 0.001 to 0.1, more preferably has MS(N+) of from 0.05 to 0.7, MS(Gly) of from 0.5 to 2.5 and MS(HC) of from 0.001 to 0.06.

<Surfactant>

The surfactant to be in the surfactant composition of the present invention may be any and every surfactant capable of being generally used in drugs, quasi-drugs, cosmetics, toiletry goods, sundries, etc. Concretely, there are mentioned alone or in a combination of two or more kinds selected from anionic surfactants, nonionic surfactants, cationic surfactants and ampholytic surfactants.

(Anionic Surfactant)

As the anionic surfactant, preferred are at least one selected from sulfate ester salts, sulfonate salts, carboxylate salts, phosphate ester salts and amino acid salts having a hydrophobic site.

Concretely, there are mentioned sulfate ester salts having a hydrophobic site, such as alkylsulfate salts, alkenylsulfate salts, polyoxyalkylene alkyl ether sulfate salts, polyoxyalkylene alkenyl ether sulfate salts, polyoxyalkylene alkylphenyl ether sulfate salts, etc.; sulfonate salts having a hydrophobic site, such as alkyl sulfosuccinate salts, alkyl polyoxyalkylenesulfosuccinate salts, alkanesulfonate salts, acylisethionates, acylmethyl taurates, internal olefinsulfonate salts having from 12 to 24 carbon atoms to be mentioned below, etc.; carboxylic acid salts having a hydrophobic site, such as higher fatty acid salts having from 8 to 16 carbon atoms, alkyl ether acetate salts represented by the following general formula (I), etc.; phosphate ester salts having a hydrophobic site, such as alkylphosphate salts, polyoxyalkylene alkyl ether phosphate salts, etc.; amino acid salts having a hydrophobic site, such as acylglutamate salts, alanine derivatives, glycine derivatives, arginine derivatives, etc.

$$R—O—(CH_2CH_2O)_a—CH_2—COOM \quad (I)$$

(In the formula, R represents an alkyl group having from 4 to 22 carbon atoms, a indicates a number of from 4 to 16, M represents a hydrogen atom, an alkali metal, an alkaline earth metal (½ atom), an ammonium or an organic ammonium.)

Except the above-mentioned internal olefinsulfonate salts having from 12 to 24 carbon atoms, the above-mentioned cationic surfactants preferably have, as the hydrophobic site therein, an alkyl group or alkenyl group having from 8 to 20 carbon atoms, from the viewpoint of the washing performance, the foaming performance and the foam quality of the wash composition and from the viewpoint of providing the effects of the present invention. The alkyl group or alkenyl group more preferably has at least 10 carbon atoms and more preferably has at most 16 carbon atoms.

Of the above-mentioned anionic surfactants, more preferred are at least one selected from alkylsulfate salts such as sodium lauryl sulfate, etc.; polyoxyethylene alkyl ether sulfate salts such as sodium polyoxyethylene lauryl ether sulfate (sodium laureth-1 sulfate, sodium laureth-2 sulfate), etc.; higher fatty acid salts having from 8 to 16 carbon atoms, such as potassium laurate, etc.; alkyl ether acetate salts represented by the above-mentioned general formula (I), such as sodium laureth-4,5 acetate, etc.; alkyl sulfosuccinate salts such as sodium laureth-2 sulfosuccinate, etc.; acylglutamate salts such as sodium N-acyl-L-glutamate (sodium cocoylglutamate), etc.; and acylisethionates, acylmethyl taurates, and internal olefinsulfonate salts having from 12 to 24 carbon atoms. More preferred are at least one selected from polyoxyethylene alkyl ether sulfate salts, alkylsulfate salts, and internal olefinsulfonate salts having from 12 to 24 carbon atoms.

[Internal Olefinsulfonate Salts]

The surfactant composition of the present invention may contain, as a cationic surfactant therein, an internal olefinsulfonate salt having from 12 to 24 carbon atoms (hereinafter this may be simply referred to as "internal olefinsulfonate salt"), from the viewpoint of the stability of the composition to the environment and the mildness thereof, from the viewpoint of improving the washing performance of the composition, improving the foam quality thereof, improving the good foam sustainability and improving the rinsing performance thereof, and in washing hair, improving the finger-combability of the composition, in rinsing hair, improving the good smoothness feeling and its sustained feeling thereof, and after drying, giving a good moist feeling, uniformity and manageability to the hair, and further from the viewpoint of giving a good most feeling to the skin treated with the composition.

In the present invention, the internal olefinsulfonate salt is a sulfonate salt obtained by sulfonating a starting internal olefin (olefin having a double bond inside the olefin chain), followed by neutralizing and hydrolyzing it. In the broad sense thereof, such an internal olefin includes a case that contains a minor amount of a so-called α-olefin in which the double bond is positioned at the 1-position of the carbon chain. In other words, when such an internal olefin is sulfonated, then a β-sultone is quantitatively formed, and a part of the β-sultone is changed into a γ-sultone and an olefinsulfonic acid, and further, these are converted into a hydroxyalkanesulfonate salt and an olefinsulfonate salt in the neutralization/hydrolysis step (for example, J. Am. Oil Chem. Soc., 69, 39 (1992)). The hydroxyl group in the hydroxyalkanesulfonate salt obtained here exists inside the alkane chain, and the double bond of the olefinsulfonate salt exists inside the olefin chain. The obtained product is mainly a mixture of these, and in a part thereof, there may be contained a minor amount of a hydroxyalkanesulfonate salt having a hydroxy group at the terminal of the carbon chain therein, or an olefinsulfonate salt having a double bond at the terminal of the carbon chain therein. In this specification, these products and their mixtures are referred to as a collective term of an internal olefinsulfonate salt. In addition, a hydroxyalkanesulfonate salt may be referred to as a hydroxy form of an internal olefinsulfonate salt (hereinafter this may also be referred to as HAS), and an olefinsulfonate salt may be referred to as an olefin form of an internal olefinsulfonate salt (hereinafter this may be also referred to as IOS).

The carbon number of the internal olefinsulfonate salt is preferably at least 12, from the viewpoint of improving the foamability, the foaming sustainability and the rinsing performance and therefore improving the finger-combability in hair washing, the smoothness performance in rinsing, the moist feeling and uniformity after drying, and the moist feeling of skin, more preferably at least 14, even more preferably at least 16. In addition, from the viewpoint of improving the finger-combining performance in hair washing, the smoothness performance and the smoothness feeling sustainability in rinsing, the moist feeling and uniformity after drying, and the moist feeling of skin, the carbon number is preferably at most 24, more preferably at most 20, even more preferably at most 18. Various types of those hydroxy forms and olefin forms each having a different carbon number are derived from the internal olefins used as the starting material, and the surfactant for use herein may contain any other hydroxy forms and olefin forms of which the carbon number differs from that of the above-mentioned ones.

One alone or two or more different types of such internal olefinsulfonate salts may be used here either singly or as combined.

In case where two or more different types of internal olefinsulfonate salts are used as combined, preferred is use of a combination of an internal olefinsulfonate salt having 16 carbon atoms and an internal olefinsulfonate salt having 18 carbon atoms, from the viewpoint of improving the foaming performance, the foaming sustainability and the rinsing performance, improving the finger-combability in hair washing, improving the smoothness feeling and its sustained feeling in rinsing, improving the most feeling, uniformity and manageability after drying, and improving the moist feeling of the skin.

In this case, in the surfactant composition of the present invention, the ratio by mass of the content of the internal olefinsulfonate salt having 16 carbon atoms to the content of the internal olefinsulfonate salt having 18 carbon atoms (internal olefinsulfonate salt having 16 carbon atoms/internal olefinsulfonate salt having 18 carbon atoms) is preferably from 50/50 to 99/1, from the above-mentioned viewpoints, more preferably from 60/40 to 95/5, even more preferably from 70/30 to 90/10, still more preferably from 75/25 to 90/10, further more preferably from 75/25 to 85/15, still further more preferably from 78/22 to 85/15.

The ratio by mass may be determined through high-performance liquid chromatography-mass spectrometry (hereinafter this is abbreviated as "HPLC-MS"). Concretely, from the internal olefinsulfonate salt or the obtained surfactant composition to be analyzed, the internal olefinsulfonate salt having 16 carbon atoms and the internal olefinsulfonate salt having 18 carbon atoms are separated through HPLC, and the two are further analyzed through MS for identification. From the HPLC-MS peak area, the intended mass ratio may be determined.

The content of the internal olefinsulfonate salts in which the sulfonate group exists at the 2-position to the total amount of the internal olefinsulfonate salts in the surfactant composition of the present invention is preferably at most 25% by mass, from the viewpoint of improving the foaming performance, the foaming sustainability and the rinsing performance, improving the finger-combability in hair washing, improving the smoothness feeling and its sustained feeling in rinsing, improving the most feeling, uniformity and manageability after drying and improving the moist feeling of the skin, more preferably at most 23% by mass; but from the viewpoint of reducing the production cost, increasing the producibility and improving the foaming sustainability and the finger-combability in hair washing, the content is preferably at least 5% by mass, more preferably at least 8% by mass.

The content of the internal olefinsulfonate salts in which the sulfonate group exists at the 2-position therein may be determined according to the method of nuclear magnetic resonance spectrometry. Concretely, the content may be determined according to the method of gas chromatography described in the section of Examples given hereinunder.

Preferably, the internal olefinsulfonate salt is a mixture of the hydroxy form and the olefin form thereof. The ratio by mass of the content of the hydroxy form of the internal olefinsulfonate salt to the content of the olefin form of the internal olefinsulfonate salt (hydroxy form/olefin form) in the surfactant composition is preferably from 50/50 to 100/0, from the viewpoint of improving the producibility and reducing impurities, more preferably from 70/30 to 100/0, even more preferably from 75/25 to 95/5.

The ratio by mass of the content of the hydroxy form of the internal olefinsulfonate salt to the content of the olefin form of the internal olefinsulfonate salt in the surfactant composition of the present invention may be determined by separating the hydroxy form and the olefin form from the internal olefinsulfonate salt or the surfactant composition containing the salt through HPLC and quantifying them according to the method described in the section of Examples.

The internal olefinsulfonate salt may be obtained by sulfonating a starting internal olefin having from 12 to 24 carbon atoms followed by neutralizing and hydrolyzing it. The conditions of sulfonation, neutralization and hydrolysis are not specifically defined. For example, herein referred to are the conditions described in Japanese Patent 1633184 and 2625150, and Tenside Surf. Det. 31 (5) 299 (1994).

In the present invention, the starting internal olefin means an olefin substantially having a double bond inside the olefin chain thereof, as described above. The carbon number of the starting internal olefin is preferably at least 12, from the viewpoint of improving the foamability, the foaming sustainability and the rinsing performance of the surfactant composition and therefore improving the finger-combability in hair washing, the smoothness performance and its long-lasting smoothness feeling in rinsing, the moist feeling and uniformity after drying, and the moist feeling of skin, more preferably at least 14, even more preferably at least 16. In addition, from the viewpoint of improving the finger-combining performance in hair washing, the smoothness performance and the smoothness feeling sustainability in rinsing, the moist feeling and uniformity after drying, and the moist feeling of skin, the carbon number is preferably at most 24, more preferably at most 20, even more preferably at most 18. One alone or two or more different types of the starting olefins may be used here either singly or as combined.

The content of the internal olefin in which the double bond exists in the 2-position therein in the starting internal olefin is preferably at most 40% by mass, from the viewpoint of improving the foamability, the foaming sustainability and the rinsing performance and therefore improving the finger-combability in hair washing, the smoothness performance and its long-lasting smoothness feeling in rinsing, the moist feeling, the uniformity and the manageability after drying, and the moist feeling of skin, more preferably at most 35% by mass; and from the viewpoint of reducing the production cost and improving the producibility and from the viewpoint of imparting to the composition a good finger-combing feeling in hair washing, the content is preferably at most 5% by mass, more preferably at most 9% by mass, even more preferably at most 15% by mass.

The double bond distribution in the starting internal olefin may be analyzed, for example, through gas chromatography-mass spectrometry (hereinafter abbreviated as "GC-MS"). Concretely, using a gas chromatography analyzer (hereinafter abbreviated as "GC"), the components differing from each other in point of the carbon chain length and the double bond position are accurately separated from each other, and each component is subjected to mass spectrometry (hereinafter abbreviated as "MS") to thereby identify the double bond position therein. From the GC peak area, the proportion of each component may be determined.

The sulfonation reaction may be attained by reacting one mol of a starting internal olefin with from 1.0 to 1.2 mols of sulfur trioxide gas. The reaction temperature is preferably from 20 to 40° C.

For the neutralization, an aqueous alkali solution of sodium hydroxide, ammonia, 2-aminoethanol or the like is reacted with the sulfonated product in an amount of from 1.0 to 1.5 molar times relative to the theoretical amount of the sulfonate group in the product.

The hydrolysis may be carried out at from 90 to 200° C. for 30 minutes to 3 hours in the presence of water. These reactions may be carried out continuously. After the reaction, the product may be purified through extraction, washing, etc.

In producing the internal olefinsulfonate salt, a starting internal olefin having a carbon number distribution of from 12 to 24 may be used for sulfonation, neutralization and hydrolysis; or a starting internal olefin having a single carbon number may be used for sulfonation, neutralization and hydrolysis; and if desired, different types of internal olefinsulfonate salts each having a different carbon number and having been produced separately may be mixed.

(Nonionic Surfactant)

The nonionic surfactant for use herein includes polyethylene glycol-type nonionic surfactants such as polyoxyethylene sorbitan fatty acid esters, polyoxyethylene sorbitol fatty acid esters, polyoxyethylene glycerin fatty acid esters, polyoxyethylene fatty acid esters, polyoxyethylene alkyl ethers, polyoxyethylene alkylphenyl ethers, polyoxyethylene (hardened) castor oil, etc.; polyalcohol-type nonionic surfactants such as sucrose fatty acid esters, polyglycerin alkyl ethers, polyglycerin fatty acid esters, alkyl glycosides, etc.; and fatty acid alkanolamides.

From the viewpoint of providing the effects of the present invention, the nonionic surfactant preferably has, as the hydrophobic site therein, an alkyl group or alkenyl group having from 8 to 20 carbon atoms.

Of those, preferred are at least one selected from polyoxyalkylene alkyl ethers, polyoxyethylene hardened castor oil, fatty acid alkanolamides and alkyl glucosides; more preferred are at least one selected from polyoxyalkylene alkyl ethers and fatty acid alkanolamides; and even more preferred are at least one selected from polyoxyethylene alkyl ethers such as polyoxyethylene lauryl ether, polyoxyethylene cetostearyl ether, etc., and fatty acid monoalkanolamides such as coconut oil fatty acid monoethanolamide, coconut oil fatty acid N-methylmonoethanolamide, etc.

(Ampholytic Surfactant)

The ampholytic surfactant includes betaine-type surfactants such as imidazoline betaines, alkyldimethylaminoacetate betaines, fatty acid amide propylbetaines, sulfobetaines, etc.; and amine oxide-type surfactants such as alkyldimethylamine oxides, etc.

Of those, from the effect of providing the effects of the present invention, preferred are at least one selected from imidazoline betaines, alkyldimethylaminoacetate betaines, fatty acid amide propylbetaines, and alkylhydroxysulfobetaines; concretely preferred are at least one selected from coconut oil fatty acid amide propylbetaine, Laurylcarboxymethylhydroxyimidazolium betaine, lauryldimethylaminoacetate betaine and laurylhydroxysulfobetaine.

(Cationic Surfactant)

The cationic surfactant includes quaternary ammonium salts having a hydrocarbon group having from 12 to 28 carbon atoms and optionally interrupted by an amide group, an ester group or an ether group, pyridinium salts, as well as tertiary amine salts with mineral acids or organic acids. Concretely, there are mentioned mono-long chain alkyltrimethylammonium salts such as cetyltrimethylammonium salts, stearyltrimethylammonium salts, behenyltrimethylammonium salts, octadecyloxypropyltrimethylammonium salts, etc.; di-long chain alkyldimethylammonium salts such as distearyldimethylammonium salts, diisotetradecyldimethylammonium salts, etc.; mono-long chain alkyldimethylamine salts such as stearyldimethylamine, behenyldimethylamine, octadecyloxypropyldimethylamine, dimethylaminopropylstearamide hydrochloride, citrate or lactate, etc.

Of those, from the viewpoint of providing the effects of the present invention, preferred are mono-long chain alkyltrimethylammonium salts such as behenyltrimethylammonium chloride, cetyltrimethylammonium chloride, etc.

(Content of Surfactant)

The content of the surfactant in the surfactant composition of the present invention is, from the viewpoint of providing the effects of the present invention, preferably at least 0.01% by mass, more preferably at least 0.1% by mass; and from the same viewpoint, the content is preferably at most 80% by mass, more preferably at most 50% by mass, even more preferably at most 36% by mass. Accordingly from the viewpoint as above, the content of the surfactant in the surfactant composition of the present invention is preferably within a range of from 0.01 to 80% by mass, preferably from 0.1 to 50% by mass, even more preferably from 0.1 to 36% by mass.

(Ratio by Mass of CCE to Surfactant)

In the surfactant composition of the present invention, the ratio by mass of CCE to the surfactant [CCE/surfactant] is, from the viewpoint of providing the effects of the present invention, preferably at least 0.0002, more preferably at least 0.005, and is also preferably at most 10, more preferably at most 5, even more preferably at most 3. Accordingly from the viewpoint as above, [CCE/surfactant] is preferably from 0.0002 to 10, more preferably from 0.0002 to 5, even more preferably from 0.005 to 3.

<Water>

The content of water in the surfactant composition of the present invention is, from the viewpoint of providing the effects of the present invention, preferably at least 10% by mass in the surfactant composition, more preferably at least 40% by mass, and is preferably at most 99.5% by mass.

Accordingly from the viewpoint as above, the water content is preferably from 10 to 99.5% by mass, more preferably from 40 to 99.5% by mass.

<Cationic Polymer Except CCE>

The surfactant composition of the present invention may additionally contain any other cationic polymer than CCE, from the viewpoint of, in application thereof to a hair wash composition, the foam softness and the good finger-combing feeling and softness of hair in hair washing, the smoothness feeling, the softness, the long-lasting smoothness feeling and the coated feeling in hair rinsing, from the viewpoint of further improving the rinsing performance, and, in application of the surfactant composition of the present invention to a hair wash composition or a hair conditioner composition, from the viewpoint of the ability thereof to give softness to hair in rinsing or after towel-drying, and, in application thereof to a skin cleanser composition, from the viewpoint of further improving the moist feeling after drying. The cationic polymer as referred to in the present invention means a polymer that has a substituent capable of being a cation (cationic group) under the condition where the surfactant composition of the present invention is used. The cationic group includes, for example, quaternary ammonium groups, and primary to tertiary amino groups.

As the other cationic polymer than CCE, there may be mentioned at least one selected from cationic galactomannans, cationized hydroxyalkyl celluloses, cationized starches, and cationic synthetic polymers produced through radical polymerization.

The cationic galactomannan is a polymer prepared by introducing a cationic group into a galactomannan polysaccharide, and is preferably a cationic polymer prepared by introducing a quaternary nitrogen-containing group thereinto. The cationic galactomannan may be produced by reacting a galactomannan polysaccharide with a cationizing agent.

The cationic galactomannan includes cationized tara gum (*Caesalpinia* gum) such as Catinal CTR-100 (by Toho Chemical), etc.; cationized locust bean gum such as Catinal CLB-100 (by Toho Chemical), etc.; cationized fenugreek gum such as Catinal CG-100 (by Toho Chemical), etc.; cationized guar gum such as Jaguar C-13S, Jaguar C-14S, Jaguar C-17, Jaguar C-500, Jaguar C-162 and Jaguar EXCEL sold by Rhodia, N-Hance BF17, N-Hance 3215, N-Hance CCG450, N-Hance 3196, N-Hance BF13, N-Hance CG13, N-Hance CCG45, N-Hance 3000, AquaCat PF618, AquaCat CG518 and N-Hance HPCG1000 sold by Ashland, etc.; cationized cassia gum such as Sensomer CT-250 polymer and Sensomer ST-400 polymer sold by Lubrizol, etc.; cationized honey locust gum; and cationized Chinese parasol-tree gum, etc.

Of those, from the viewpoint of the foam softness, the finger-combability and the softness of hair in hair washing, and the smootheness property, the softness, the long-lasting smoothness property and the coated feeling in hair rinsing in application of the surfactant composition of the present invention to a hair wash composition, and from the viewpoint of the moist feeling of skin after washed and dried in application of the composition to a skin cleanser composition, preferred are cationized tara gum, cationized locust bean bum, cationized fenugreek gum, cationized guar gum, and cationized cassia gum, more preferred are cationized tara gum, cationized locust bean gum, cationized guar gum and cationized cassia gum, and even more preferred is cationized guar gum.

The cationized hydroxyalkyl cellulose includes a cationized hydroxyethyl cellulose (hereinafter this may be referred to as "C-HEC"), a cationized hydroxypropyl cellulose, etc. The cationized hydroxyalkyl cellulose may be obtained by adding a cationic group and an alkyleneoxy group to cellulose. The cationic group is preferably a quaternary ammonium group.

Examples of commercial products of C-HEC include UCARE JR125, UCARE JR4.00, UCARE JR30M, UCARE LR400, UCARE LR30M, SOFTCAT SL-5, SOFTCAT SL-30, SOFTCAT SL-60, SOFTCAT SL-100, SOFTCAT SX-400X, SOFTCAT SX-1300H, SOFTCAT SX-1300X, SOFTCAT SK-H and SOFTCAT SK-MH sold by Dow Chemical, etc.

The cationized hydroxypropyl cellulose may be produced by reacting cellulose with a cationizing agent and propylene oxide, and for the details of the production method, for example, referred to is WO2012/091072.

The cationized starch is a starch derivative prepared by introducing a quaternary nitrogen-containing group into starch. The cationized starch may be produced by reacting starch with a cationizing agent. The cationic group is preferably a quaternary ammonium group. Commercial products of the cationized starch include Sensomer CI-50 sold by Lubrizol, etc.

The cationic polymer produced through radical polymerization includes, for example, methacryloxyalkyl quaternary ammonium salt-acrylamide copolymers such as Merquat 5 (by Lubrizol), etc.; diallyl quaternary ammonium salts-acrylamide copolymers such as Merquat 550, Merquat 740, Merquat 2200 and Merquat S (all by Lubrizol), etc.; diallyl quaternary ammonium-acrylic acid copolymers such as Merquat 280 and Merquat 295 (both by Lubrizol), etc.; diallyl quaternary ammonium salt-acrylamide-acrylic acid copolymers such as Merquat 3330DRY (by Lubrizol), etc.; methacrylamide alkyl quaternary ammonium salt-acrylic acid-acrylate copolymers such as Merquat 2001 (by Lubrizol), etc.; methacrylamide alkyl quaternary ammonium salt-acrylic acid-acrylamide copolymers such as Merquat 2003 (by Lubrizol), etc.; diallyl quaternary ammonium salt-vinylpyrrolidone-vinylimidazole copolymers such as Luviquat Sensation (by BASF), etc.; and crosslinked copolymers of cationic synthetic polymers produced through radical polymerization as mentioned above, such as Sofcare KG-301W (by Kao), Sofcare KG-101W (by Kao), etc.

Of those, from the viewpoint of the foam softness, the finger-combability and the softness of hair in hair washing, and the smoothness property, the softness, the long-lasting smoothness property and the coated feeling in hair rinsing in application of the surfactant composition of the present invention to a hair wash composition, preferred are diallyl quaternary ammonium salt-acrylamide copolymers, diallyl quaternary ammonium salt-acrylamide-acrylic acid copolymers, methacrylamide alkyl quaternary ammonium salt-acrylic acid-acrylate copolymers, methacrylamide alkyl quaternary ammonium salt-acrylic acid-acrylamide copolymers, diallyl quaternary ammonium salt-vinylpyrrolidone-vinylimidazole copolymers and their crosslinked copolymers, and more preferred are diallyl quaternary ammonium salt-acrylamide copolymers.

Of the above, as the cationic polymer except CCE, from the viewpoint of the foam softness, the finger-combability and the softness of hair in hair washing, and the smoothness property, the softness, the long-lasting smoothness property and the coated feeling in hair rinsing in application of the surfactant composition of the present invention to a hair wash composition, preferred are at least one selected from cationic galactomannans, cationized hydroxyalkyl celluloses, and cationic synthetic polymers produced through radical polymerization, more preferred are at least one selected from cationized guar gum, cationized cassia gum, cationized locust bean gum, cationized hydroxyethyl cellulose, cationized hydroxypropyl cellulose, and diallyl quaternary ammonium salt-acrylamide copolymers, and even more preferred are cationized guar gum and cationized locust bean gum.

One alone or two or more different types of such other cationic polymers than CCE may be used here either singly or as combined.

The content of the other cationic polymer than CCE in the surfactant composition of the present invention is, from the viewpoint of the foam softness, the finger-combability and the softness of hair in hair washing, and the smoothness property, the softness, the long-lastinf smoothness property and the coated feeling in hair rinsing in application of the surfactant composition of the present invention to a hair wash composition, and from the viewpoint of the moist feeling after skin washing in application of the composition to a skin cleanser composition, preferably at least 0.01% by mass in the surfactant composition, more preferably at least 0.02% by mass, even more preferably at least 0.05% by mass, and is preferably at most 5% by mass, more preferably at most 2% by mass, even more preferably at most 0.5% by mass.

According from the above-mentioned viewpoints, the content of the other cationic polymer than CCE in the surfactant composition of the present invention is preferably from 0.01 to 5% by mass, more preferably from 0.02 to 2% b mass, even more preferably from 0.05 to 0.5% by mass.

The ratio by mass of CCE to the other cationic polymer than CCE [CCE/other cationic polymer than CCE] in the surfactant composition of the present invention is, from the viewpoint of the foam softness, the finger-combability and the softness of hair in hair washing, and the smoothness property, the softness, the long-lasting smoothness property and the coated feeling in hair rinsing in application of the surfactant composition of the present invention to a hair wash composition, and from the viewpoint of the moist feeling after skin washing in application of the composition to a skin cleanser composition, preferably at least 0.05, more preferably at least 0.1, even more preferably at least 0.5, still more preferably at least 1, and is preferably at most 20, more preferably at most 10, even more preferably at most 8, still more preferably at most 5. Accordingly from the above-mentioned viewpoints, the ratio by mass of the content of CCE to the content of the other cationic polymer than CCE in the surfactant composition is preferably from 0.05 to 20, more preferably from 0.1 to 10, even more preferably from 0.5 to 8, still more preferably from 1 to 5.

<Oily Agent>

Within a range not detracting from the effects of the present invention, the surfactant composition of the present invention may contain an oily agent.

The oily agent is an oily component generally used in drugs, quasi-drugs, cosmetics, toiletry goods, sundries and the like, and usable here is any and every hardly water-soluble or water-insoluble oily agent of which the amount of dissolution in 100 g of water at 20° C. is from 0 g to 1 g. The oily agent is, from the viewpoint of providing the effects of the present invention, especially providing an excellent moist feeling, good uniformity and excellent moisturizing feeling after drying in use of the surfactant composition of the present invention, preferably such that the amount of dissolution thereof in 100 g of water at 20° C. is at most 0.5 g, more preferably at most 0.1 g.

From the above-mentioned viewpoints, the oily agent for use herein is preferably at least one selected from (i) ester oils, (ii) silicone oils, (iii) ether oils, (iv) hydrocarbon oils, (v) higher alcohols, and (vi) carboxylic acids having a hydrocarbon group optionally substituted with a hydroxyl group and having from 17 to 23 carbon atoms.

((i) Ester Oil)

As the ester oil, from the viewpoint of providing the effects of the present invention, especially providing an excellent moist feeling, good uniformity and excellent moisturizing feeling after drying in use of the surfactant composition of the present invention, preferred are ester oils represented by the following general formula (16), (17) or (19), hydrophobic carboxylate esters of dipentaerythritol, and dialkyl carbonate compounds represented by the following general formula (20).

[Ester Oil Represented by General Formula (16)]

$$R^{25}\text{—COO—}R^{26} \tag{16}$$

(In the formula, $R^{25}$ represents a linear or branched alkyl group having from 8 to 22 carbon atoms, $R^{26}$ represents a linear or branched alkyl or alkenyl group having from 1 to 22 carbon atoms.)

The carbon number of $R^{25}$ in the general formula (16) is, from the viewpoint of the excellent most feeling, uniformity and moisturizing feeling after drying in use of the surfactant composition of the present invention, preferably at least 10, more preferably at least 12, and preferably at most 20, more preferably at most 18. Accordingly from the viewpoint mentioned above, the carbon number of $R^{25}$ is preferably from 10 to 20, more preferably from 12 to 18.

The carbon number of $R^{26}$ is, from the above-mentioned viewpoint, preferably at least 1 and preferably at most 20, more preferably at most 18. Accordingly from the above-mentioned viewpoint, the carbon number of $R^{26}$ is preferably from 1 to 20, more preferably from 1 to 18. More preferably, $R^{26}$ is a linear or branched alkyl or alkenyl group having from 1 to 18 carbon atoms and optionally interrupted by a phenyl group.

Specific examples of the ester oils represented by the general formula (16) include bees wax, lanolin, lanolin, hydrogenated, lanolin fatty acid octyl dodecyl ester, caprylyl eicosenoate, myristyl 2-ethylhexanoate, cetyl 2-ethylhexanoate, stearyl 2-ethylhexanoate, octyl octanoate, lauryl octanoate, myristyl octanoate, isocetyl octanoate, octyl propylheptanoate, cetostearyl isononanoate, isononyl isononanoate, isotridecyl isononanoate, methyl laurate, hexyl laurate, octyl laurate, isopropyl myristate, octyl myristate, myristyl myristate, octyldodecyl myristate, isopropyl palmitate, 2-ethylhexyl palmitate, octyl palmitate, cetyl palmitate, methyl oleate, oleyl oleate, decyl oleate, isobutyl oleate, methyl stearate, 2-ethylhexyl stearate, octyl stearate, isocetyl stearate, stearyl stearate, butyl stearate, isotridecyl stearate, isopropyl isostearate, isocetyl isostearate, isostearyl isostearate, 2-ethylhexyl hydroxystearate, oleyl erucate, etc.

Of the ester oils represented by the general formula (16), more preferred from the viewpoint of the excellent moist feeling, the uniformity and the moisturizing feeling after drying in use of the surfactant composition of the present invention, are octyl laurate, octyl myristate, octyldodecyl myristate, isopropylmyristate, myristyl myristate, isopropyl palmitate, 2-ethylhexyl palmitate, octyl palmitate, cetyl palmitate, methyl stearate, 2-ethylhexyl stearate, octyl stearate, isocetyl stearate, stearyl stearate, butyl stearate and isotridecyl stearate, and even more preferred are at least one selected from octyl laurate, octyl myristate, myristyl myristate, isopropyl palmitate, octyl palmitate, cetyl palmitate, octyl stearate, isocetyl stearate, stearyl stearate, isostearyl stearate, and isostearyl isostearate.

[Ester Oil Represented by General Formula (17)]

[Chem. 8]

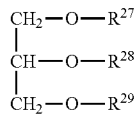

(17)

(In the formula, $R^{27}$, $R^{28}$ and $R^{29}$ each independently represent a hydrogen atom, or a group represented by the following general formula (18), and all of these are not hydrogens at the same time.)

$$\text{—CO—}R^{30} \tag{18}$$

(In the formula, $R^{30}$ represents a linear or branched alkyl or alkenyl group having from 8 to 22 carbon atoms, optionally substituted with a hydroxyl group and optionally interrupted by a carboxylate ester group.)

In the general formula (18), the carbon number of $R^{30}$ is, from the viewpoint of the excellent moist feeling, the uniformity and the moisturizing feeling after drying in use of the surfactant composition of the present invention, preferably from 8 to 20, more preferably from 8 to 18.

Specific examples of the ester oils represented by the general formula (17) include castor oil, cacao oil, mink oil, avocado oil, olive oil, sunflower oil, camellia oil, apricot kernel oil, almond oil, wheat germ oil, *Theobroma grandiflorum* seed butter, grape seed oil, babassu oil, jojoba oil, macadamia nut oil, *Camellia* Oleifera seed oil, shea butter, *Camellia reticulata* seed oil, meadowfoam oil, glyceryl tribehanate, triisostearin, etc.

Among the ester oils represented by the general formula (17), from the viewpoint of the excellent moist feeling, the uniformity and the moisturizing feeling after drying in use of the surfactant composition of the present invention, preferred are sunflower oil, avocado oil, camellia oil, macadamia nut oil and shea butter, and more preferred are at least one selected from sunflower oil, avocado oil, camellia oil, macadamia nut oil and shea butter.

[Ester Oil Represented by General Formula (19)]

$$R^{31}\text{O-(AO)}m\text{-COR}^{32} \tag{19}$$

(In the formula, $R^{31}$ represents a substituted or unsubstituted hydrocarbon group containing at least one aromatic group and having from 6 to 20 carbon atoms, $R^{32}$ represents a linear or branched alkyl or alkenyl group having from 1 to 25 carbon atoms. AO represents an oxyalkylene group having from 2 to 4 carbon atoms, m indicates a number of from 1 to 50. When m is 2 or more, m's AO groups may be the same or different.)

$R^{31}$ in the general formula (19) is, from the viewpoint of the most feeling, the uniformity and the moisturizing feeling after drying in use of the surfactant composition of the present invention, preferably an aromatic hydrocarbon having from 6 to 12 carbon atoms, more preferably an aromatic hydrocarbon group having from 6 to 10 carbon atoms, even more preferably a benzyl group.

$R^{32}$ is, from the above-mentioned viewpoint, preferably an alkyl group having at least 7 carbon atoms, more preferably an alkyl group having at least 11 carbon atoms, and is preferably an alkyl group having at most 21 carbon atoms, more preferably at most 15 carbon atoms. $R^{32}$ is preferably an alkyl group having from 7 to 21 carbon atoms, more preferably an alkyl group having from 11 to 15 carbon atoms.

The AO group is, from the above-mentioned viewpoint, preferably a propyleneoxy group, and m is preferably from 1 to 10, more preferably from 1 to 5.

Preferred examples of the ester oils represented by the general formula (19) include an ester of myristic acid with benzyl alcohol propylene oxide (3 mols) adduct (Croda's trade name, Crodamol STS), an ester of 2-ethylhexyl acid with benzyl alcohol propylene oxide (3 mols) adduct (Croda's trade name, Crodamol SFX), etc.

[Hydrophobic Carboxylate of Dipentaerythritol]

The hydrophobic carboxylate of dipentaerythritol is a compound produced through dehydrating condensation of dipentaerythritol and one or more hydrophobic carboxylic acids, in which the hydrophobic carboxylic acid is a carboxylic acid that has a hydrocarbon group having from 15 to 23 carbon atoms and optionally having a hydroxyl group. Specific examples of the hydrophobic carboxylic acid include palmitic acid, stearic acid, oleic acid, isostearic acid, hydroxystearic acid, rosin acid, etc.

From the viewpoint of availability, preferred is an ester of a mixed acid of hydroxystearic acid, stearic acid and rosin acid with pentaerythritol.

[Dialkyl Carbonate Compound Represented by General Formula (20)]

$$R^{33}-O-(CH_2CH_2O)v-CO-(OCH_2CH_2)w-OR^{34} \quad (20)$$

(In the formula, $R^{33}$ and $R^{34}$ each represent a linear or branched alkyl group and/or alkenyl group each having from 6 to 22 carbon atoms, v and w each indicate 0 or a number of from 1 to 50.)

$R^{33}$ and $R^{34}$ in the general formula (20) is, from the viewpoint of the most feeling, the uniformity and the moisturizing feeling after drying in use of the surfactant composition of the present invention, preferably an alkyl group having at least 8 carbon atoms, more preferably an alkyl group having at most 18 carbon atoms, even more preferably an alkyl group having at most 12 carbon atoms. From the above-mentioned viewpoint, preferably, $R^{33}$ and $R^{34}$ each are an alkyl group having from 6 to 18 carbon atoms, more preferably an alkyl group having from 8 to 12 carbon atoms.

Also from the above-mentioned viewpoint, preferably, v and w each indicate 0 or a number of from 1 to 5, more preferably 0.

Preferred examples of the dialkyl carbonate compounds represented by the general formula (20) include dioctyl carbonate (Cognis' Cetiol CC), etc.

The other ester oils than the above include, for example, an ester of a polycarboxylic acid with an alcohol, an ester of a polyalcohol except glycerin, dipentaerythritol and saccharides with a fatty acid, an ester of a saccharide and a fatty acid, etc. Their specific examples include diisopropyl dimer acid ester, propanediol dicaprate, diisopropyl adipate, dimethoxyethyl succinate, 2-ethylhexyl succinate, poly-soybean fatty acid sucrose, polysucrose behenate, sucrose tetraisostearate, hydroxyalkyl. (C16-18) hydroxydimer dilinoleyl ether, pentaerythrityl tetrastearate, glycol distearate, etc.

((ii) Silicone Oil)

As the silicone oil, from the viewpoint of the excellent moist feeling, the uniformity and the moisturizing feeling after drying in use of the surfactant composition of the present invention, preferred are at least one selected from dimethylpolysiloxane, dimethiconol (dimethylpolysiloxane having a hydroxyl group at the terminal thereof), and amino-modified silicone (dimethylpolysiloxane having an amino group in the molecule), polyether-modified silicone, glyceryl-modified silicone, amino derivative silicone, silicone wax and silicone elastomer.

The viscosity of the silicone oil (at 25° C.) is preferably from 10 mm²/sec to 15,000,000 mm²/sec from the above-mentioned viewpoint and from the viewpoint of the dispersibility in preparing the surfactant composition.

((iii) Ether Oil)

As the ether oil, from the viewpoint of the excellent moist feeling, the uniformity and the moisturizing feeling after drying in use of the surfactant composition of the present invention, preferred are dialkyl ether compounds represented by the following general formula (21) or polyoxyalkylene alkyl ether compounds represented by the following general formula (22).

[Dialkyl Ether Compound Represented by General Formula (21)]

$$R^{35}-O-R^{36} \quad (21)$$

(In the formula, $R^{35}$ and $R^{36}$ each represent a linear or branched alkyl and/or alkenyl group each having from 6 to 22 carbon atoms.)

$R^{35}$ and $R^{36}$ in the general formula (21) each are, from the viewpoint of the moist feeling, the uniformity and the moisturizing feeling after drying in use of the surfactant composition of the present invention, preferably an alkyl group having at least 8 carbon atoms, and is preferably an alkyl group having at most 18 carbon atoms, more preferably an alkyl group having at most 12 carbon atoms. Accordingly from the same viewpoint as above, $R^{35}$ and $R^{36}$ each are preferably an alkyl group having from 6 to 18 carbon atoms, more preferably an alkyl group having from 8 to 12 carbon atoms.

Preferred examples of the dialkyl ether compounds represented by the general formula (21) include dioctyl ether (Cognis' CETIOL OE), etc.

[Polyoxyalkylene Alkyl Ether Compound Represented by General Formula (22)]

$$R^{37}-O-(PO)_r(EO)_s-H \quad (22)$$

(In the formula, $R^{37}$ represents a linear or branched alkyl or alkenyl group having from 6 to 22 carbon atoms. PO represents an oxypropylene group, and EO represents an oxyethylene group. The mean addition molar number of PO, r is a number of from 0.1 to 15, and the mean addition molar number of EO, s is a number of from 0 to 10. When s is not 0, the addition mode of PO and EO may be in a random mode or a block mode, and the addition sequence of PO and EO is not specifically defined.)

In the general formula (22), from the viewpoint of the excellent moist feeling, the uniformity and the moisturizing feeling after drying in use of the surfactant composition of the invention, the carbon number of $R^{37}$ is preferably at least 8. Also preferably the carbon number of $R^{37}$ is at most 20, more preferably at most 18, even more preferably at most 12. Accordingly from the above-mentioned viewpoint, the carbon number of $R^{37}$ is preferably from 6 to 20, more preferably from 6 to 18, even more preferably from 8 to 12.

The mean addition molar number r is, from the above-mentioned viewpoint, preferably at least 1, more preferably at least 2, even more preferably at least 3. The mean addition molar number r is preferably at most 13, more preferably at most 10.

The mean addition molar number s is, from the above-mentioned viewpoint, preferably at most 5, more preferably at most 1, even more preferably 0.

Specific examples of the polyoxyalkylene alkyl ether compounds represented by the general formula (22) include polyoxypropylene hexyl ether, polyoxypropylene octyl ether, polyoxypropylene 2-ethylhexyl ether, polyoxypropylene decyl ether, polyoxypropylene isodecyl ether, polyoxypropylene laurylether, polyoxypropylene myristyl ether, polyoxypropylene palmityl ether, polyoxypropylene cetyl ether, polyoxypropylene stearyl ether, polyoxypropylene isostearyl ether, polyoxypropylene octyldecyl ether, polyoxypropylene eicosyl ether and polyoxypropylene behenyl ether, in which the mean addition molar number r of polyoxypropylene groups is from 1 to 15.

Of those, from the above-mentioned viewpoint, preferred are at least one selected from polyoxypropylene octyl ether, polyoxypropylene decyl ether and polyoxypropylene lauryl ether in which the mean addition molar number r of polyoxypropylene groups is from 3 to 10.

((iv) Hydrocarbon Oil)

The hydrocarbon oil is, from the viewpoint of the excellent moist feeling, the uniformity and the moisturizing feeling after drying in use of the surfactant composition of the present invention, preferably a saturated or unsaturated hydrocarbon having at least 20 carbon atoms.

Specific examples of the hydrocarbon oil include squalene, squalane, liquid paraffin, liquid isoparaffin, heavy liquid isoparaffin, α-olefin oligomer, cycloparaffin, polybutene, vaseline, paraffin wax, microcrystalline wax, polyethylene wax, and ceresin. From the viewpoint of hair manageability, preferred are from squalane, squalene, liquid paraffini vaseline and paraffin wax; and more preferred are at least one selected from squalane, liquid paraffin, vaseline and paraffin wax.

((v) Higher Alcohol)

The higher alcohol is, from the viewpoint of the excellent moist feeling, the uniformity and the moisturizing feeling after drying in use of the surfactant composition of the present invention, preferably an alcohol having a linear or branched alkyl or alkenyl group having from 6 to 22 carbon atoms. Preferably, the carbon number of the alkyl or alkenyl group is at least 8, more preferably at least 12, and is preferably at most 20, more preferably at most 18. From the above-mentioned viewpoint, the carbon number of the alkyl or alkenyl group is preferably from 8 to 20, more preferably from 12 to 18.

Specific examples of the higher alcohols include hexyl alcohol, 2-ethylhexyl alcohol, octyl alcohol, decyl alcohol, isodecyl alcohol, lauryl alcohol, myristyl alcohol, palmityl alcohol, cetyl alcohol, stearyl alcohol, isostearyl alcohol, 2-octyldodecanol, eicosyl alcohol, behenyl alcohol.

Of those, from the above-mentioned viewpoint, preferred are at least one selected from lauryl alcohol, myristyl alcohol, cetyl alcohol, stearyl alcohol, behenyl alcohol and 2-octyldodecanol.

((vi) Carboxylic Acid Having Hydrocarbon Group with from 17 to 23 Carbon Atoms Optionally Substituted with Hydroxyl Group)

The hydrocarbon group in the carboxylic acid having a hydrocarbon group with from 17 to 23 carbon atoms optionally substituted with a hydroxyl group is, from the viewpoint of the excellent moist feeling, the uniformity and the moisturizing feeling after drying in use of the surfactant composition of the present invention, preferably a linear or branched alkyl group having from 17 to 23 carbon atoms.

Specific examples of the carboxylic acid having a hydrocarbon group with from 17 to 23 carbon atoms optionally substituted with a hydroxyl group include stearic acid, oleic acid, isostearic acid, hydroxystearic acid, behenic acid, rosin acid, etc. Of those, from the above-mentioned viewpoint, preferred are at least one selected from stearic acid, oleic acid, isostearic acid, hydroxystearic acid, and behenic acid, and more preferred are at least one selected from stearic acid, oleic acid and isostearic acid.

One or more of the above-mentioned oily agents may be used here either singly or as combined.

The oily agent is, especially from the viewpoint of the excellent moist feeling, the uniformity and the moisturizing feeling after drying in use of the surfactant composition of the present invention, preferably an ester oil represented by the general formula (17), dimethylpolysiloxane, a polyoxyalkylene alkyl ether represented by the general formula (22), a higher alcohol having from 12 to 18, or a saturated or unsaturated hydrocarbon having at most 20 carbon atoms.

(Content of Oily Agent)

The content of the oily agent in the surfactant composition of the present invention is, from the viewpoint of the effects of the invention, especially from the viewpoint of the excellent moist feeling, the uniformity and the moisturizing feeling after drying in use of the surfactant composition of the present invention, preferably at least 0.01% by mass, more preferably at least 0.05% by mass, even more preferably at least 0.1% by mass. From the viewpoint of preventing the sticky feeling after use of the surfactant of the present invention, the content of the oily agent in the surfactant composition is preferably at most 30% by mass, more preferably at most 20% by mass, even more preferably at most 15% by mass. Accordingly from the above-mentioned viewpoint, the content of the oily agent in the surfactant of the present invention is preferably from 0.01 to 30% by mass, more preferably from 0.05 to 20% by mass, even more preferably from 0.1 to 15% by mass.

(Ratio by Mass of CCE to Oily Agent)

The ratio by mass of CCE to the oily agent in the surfactant composition [CCE/oily agent] is, from the viewpoint of the effects of the present invention, especially from the viewpoint of the excellent moist feeling, the uniformity and the moisturizing feeling after drying in use of the surfactant composition of the present invention, preferably at least 0.001, more preferably at least 0.005, even more preferably at least 0.01, and is preferably at most 5, more preferably at most 1, even more preferably at most 0.6. Accordingly from the above-mentioned viewpoint, the ratio by mass of CCE to the oily agent in the surfactant composition of the present invention is preferably from 0.001 to 5, more preferably from 0.005 to 1, even more preferably from 0.01 to 0.6.

<Other Components>

Further, if desired, glycerin, moisturizers, polysaccharides, polypeptides, pearly agents, solvents, dyes, fragrances, propellants, chelating agents such as edates, citrates and the like, pH regulators, preservatives, anti-dandruff agents such as zinc pyrithione, piroctone olamine and the like, hair-coloring dyes, oxidizing agents, alkali agents, keratin reducing agents and others that may be generally incorporated in hair wash compositions, skin cleanser compositions, hair conditioner compositions or hair treatment compositions may be suitably incorporated in the surfactant composition of the present invention.

<Method for Producing Surfactant Composition>

The method for producing the surfactant composition of the present invention is not specifically defined, and the composition may be produced in any ordinary method. Concretely, for example, water and a surfactant are mixed under heat, then the dissolution thereof is confirmed, and thereafter CCE is added and mixed therein. The addition sequence of CCE and surfactant may be reversed.

If desired, CCE may be previously dispersed or dissolved and then added to the system.

If desired, moisturizers such as oils, cationic polymers, glycerin and the like, as well as pearly agents, pH regulators, fragrances, dyes and other components may be added to the mixture, but the addition time thereof is no specifically defined. They may be added before or after mixing of the surfactant and CCE, or may be added simultaneously with the mixing.

The forms of the surfactant composition of the present invention are not specifically defined. The composition may be in any form of liquid, foam, paste, cream, solid, powder, etc. Preferred is liquid, paste or cream, and more preferred is liquid. In case where the composition is formed as a liquid, preferably used is water as well as polyethylene glycol, ethanol and the like as a liquid medium.

The surfactant composition of the present invention can be used as hair wash compositions, skin cleanser compositions, hair conditioner compositions and hair treatment compositions, exhibiting excellent effects therein.

[Hair Wash Composition]

The surfactant of the present invention can be used as a hair wash composition.

The hair wash composition of the present invention contains CCE of the present invention, a surfactant and water.

<CCE>

The preferred range of the content of CCE in the hair wash composition of the present invention is the same as the preferred range of the content of CCE in the above-mentioned surfactant composition.

From the viewpoint of giving an excellent smoothness feeling and its sustained feeling as well as a coated feeling in hair rinsing, CCE in the hair wash composition of the present invention preferably has MS(N+) of from 0.05 to 0.30, MS(Gly) of from 0.6 to 2.4 and MS(HC) of from 0.001 to 0.06, more preferably has MS(N+) of from 0.16 to 0.28, MS(Gly) of from 1.8 to 2.3 and MS(HC) of from 0.002 to 0.05, and even more preferably has MS(N+) of from 0.20 to 0.25, MS(Gly) of from 2.0 to 2.2 and MS(HC) of from 0.01 to 0.03.

In case where the hair wash composition contains an oily agent, CCE therein preferably has, from the viewpoint of the excellent finger-combing feeling in hair washing, the excellent smoothness feeling and its sustained feeling in hair rinsing, and the most feeling and the uniformity after drying, MS(N+) of from 0.05 to 0.7, MS(Gly) of from 1.8 to 2.4 and MS(HC) of from 0.001 to 0.06, more preferably MS(N+) of from 0.11 to 0.35, MS(Gly) of from 1.8 to 2.2 and MS(HC) of from 0.002 to 0.05, even more preferably MS(N+) of from 0.18 to 0.32, MS(Gly) of from 2.0 to 2.2 and MS(HC) of from 0.005 to 0.04.

In case where the hair wash composition contains any other cationic polymer than CCE, then CCE preferably has, from the viewpoint of the excellent finger-combing feeling in hair washing, the softness of hair, the softness of foam, the excellent smoothness feeling and its sustained feeling, and the coated feeling in rinsing, MS(N+) of from 0.05 to 0.7, MS(Gly) of from 1.6 to 2.4 and MS(HC) of from 0.005 to 0.05, more preferably MS(N+) of from 0.05 to 0.28, MS(Gly) of from 1.8 to 2.3 and MS(HC) of from 0.005 to 0.03, even more preferably MS(N+) of from 0.20 to 0.25, MS(Gly) of from 2.0 to 2.2 and MS(HC) of from 0.01 to 0.03.

<Surfactant>

The surfactant to be in the hair wash composition of the present invention may be any and every surfactant capable of being generally used in drugs, quasi-drugs, cosmetics, toiletry goods, sundries, etc. Their preferred embodiments are the same as the preferred embodiments of the surfactant described in the section of the surfactant composition mentioned above. From the viewpoint of the excellent finger-combability of hair and hair softness in hair washing, the softness of foam, the excellent smoothness feeling and its sustained feeling as well as the softness and the coated feeling in rinsing, and the moist feeling and the uniformity after drying in use of the hair wash composition of the present invention, preferred are at least one selected from the anionic surfactants, the nonionic surfactants and the ampholytic surfactants described in the section of the surfactant composition mentioned above. The preferred embodiments of the anionic surfactants, the nonionic surfactants and the ampholytic surfactants are the same as those described in the section of the surfactant composition. Further, preferred are at least one selected from polyoxyethylene alkyl ether sulfates such as sodium polyoxyethylene lauryl ether sulfate, etc.; fatty acid monoalkanolamides such as coconut oil fatty acid monoethanolamide, coconut oil fatty acid N-methylmonoethanolamide, etc.; fatty acid amide propylbetaines such as coconut oil fatty acid amide propylbetaine, etc.; and alkyldimethylaminoacetate betaines such as lauryldimethylaminoacetate betaine, etc.

(Content of Surfactant)

The preferred embodiment of the content of the surfactant in the hair wash composition of the present invention is the same as that of the content of the surfactant described in the section of the surfactant composition mentioned above. From the viewpoint of the smooth finger-combability of hair, the hair softness and the foam softness in hair washing, the excellent smoothness feeling and its sustained feeling as well as the excellent softness and the coated feeling in rinsing, and the excellent moist feeling and uniformity in drying in use of the hair wash composition of the present invention, the surfactant content is preferably at most 30% by mass, more preferably at most 25% by mass, and from the same viewpoint, the surfactant content is preferably at least 5% by mass, more preferably at least 10% by mass. Accordingly from the above-mentioned viewpoint, the surfactant content is preferably from 5 to 30% by mass, more preferably from 10 to 25% by mass.

(Ratio by Mass of CCE to Surfactant)

In the hair wash composition of the present invention, the preferred embodiment of the ratio by mass of CCE to the surfactant [CCE/surfactant] is the same as the preferred embodiment of the ratio by mass of CCE to the surfactant in the section of the surfactant composition mentioned above. From the viewpoint of the smooth finger-combability of hair, the hair softness and the foam softness in hair washing, the excellent smoothness feeling and its sustained feeling as well as the excellent softness and the coated feeling in rinsing, and the excellent moist feeling and uniformity in drying in use of the hair wash composition of the present invention, the ratio is preferably at least 0.01 and at most 0.3, and more preferably at most 0.05. Accordingly from the above-mentioned viewpoint, the ratio is more preferably from 0.005 to 0.3, even more preferably from 0.01 to 0.05.

<Water>

The preferred embodiment of the water content in the hair wash composition of the present invention is the same as the preferred embodiment thereof described in the section of the surfactant composition mentioned above. From the viewpoint of the smooth finger-combability of hair, the hair softness and the foam softness in hair washing, the excellent smoothness feeling and its sustained feeling as well as the excellent softness and the coated feeling in rinsing, and the excellent moist feeling and uniformity in drying in use of the hair wash composition of the present invention, the water content is at least 60% by mass, more preferably at least 70% by mass, and is preferably at most 95% by mass, more preferably at most 90% by mass. Accordingly from the above-mentioned viewpoint, the water content is preferably from 60 to 95% by mass, more preferably from 70 to 90% by mass.

<Cationic Polymer Except CCE>

From the viewpoint of the foam softness, the smooth finger-combability of hair and the hair softness in hair washing, the excellent smoothness feeling and its sustained feeling as well as the excellent softness and the coated feeling in rinsing, and from the viewpoint of further improving the rinsing performance and giving excellent hair softness in rinsing and towel-drying in application to hair wash compositions, the hair wash composition of the present invention may contain any other cationic polymer than CCE. Specific examples and the preferred embodiment of the other cationic polymer than CCE are the same as the specific examples and the preferred embodiment of the other cationic polymer than CCE described in the section of the surfactant composition mentioned above. One alone or two or more different types of such other cationic polymers than CCE may be used here either singly or as combined.

The content of the other cationic polymer than CCE in the hair wash composition of the present invention, the ratio by mass of CCE to the other cationic polymer than CCE therein [CCE/other cationic polymer than CCE] and their preferred embodiments are the same as those described in the section of the surfactant composition mentioned above.

<Oily Agent>

From the viewpoint of giving a smooth finger-combability of hair in hair washing, an excellent smoothness feeling and its sustained feeling in rinsing, and an excellent moist feeling, uniformity and a moisturizing performance after drying, the hair wash composition of the invention may contain an oily agent added thereto. The uniformity as referred to herein means that the feeling from the hair root to the hair tip of hair tresses is uniform.

Specific examples and the preferred embodiments of the oily agent are the same as the specific examples and the preferred embodiments thereof described in the section of the surfactant composition mentioned above. From the viewpoint of giving a moist feeling, uniformly and a moisturizing feeling to hair after washed, the oily agent is preferably at least one selected from silicone oils and ether oils, and more preferably at least one selected from dimethylpolysiloxane, amino-modified dimethylpolysiloxane, and polyoxyalkylene alkyl ethers represented by the above-mentioned general formula (22).

(Content of Oily Agent)

The preferred embodiment of the content of the oily agent in the hair wash composition of the present invention is the same as the preferred embodiment of the content of the oily agent in the surfactant composition mentioned above. From the viewpoint of giving a moist feeling, uniformity and a moisturizing feeling to hair after washing, the content of the oily agent is preferably at least 0.5% by mass, more preferably at least 1% by mass, and is preferably at most 10% by mass, more preferably at most 5% by mass.

(Ratio by Mass of CCE to Oily Agent)

In the hair wash composition of the present invention, the preferred embodiment of the ratio by mass of CCE to the oily agent [CCE/oily agent] is the same as that of the ratio by mass of CCE to the oily agent in the surfactant composition.

<Other Components>

Further, if desired, glycerin, moisturizers, polysaccharides, polypeptides, pearly agents, solvents, dyes, fragrances, chelating agents such as edates, citrates and the like, pH regulators, preservatives, anti-dandruff agents such as zinc pyrithione, piroctone olamine and the like that may be generally incorporated in hair wash compositions may be suitably incorporated in the hair wash composition of the present invention.

The pH of the hair wash composition of the present invention is preferably from pH 2 to 12, more preferably from pH 3 to 10, from the viewpoint of providing the effects of the present invention.

The forms of the hair wash composition of the present invention are not specifically defined. The composition may be in any form of liquid, foam, paste, cream, solid, powder, etc. Preferred is liquid, paste or cream, and more preferred is liquid.

[Hair Washing Method]

The present invention also provides a hair washing method that comprises washing hair with the hair wash composition of the present invention, then rinsing and drying the hair.

The hair washing method is not specifically defined, to which any known method is applicable here.

[Skin Cleanser Composition]

The surfactant composition of the present invention is usable as a skin cleanser composition.

The skin cleanser composition of the present invention contains CCE of the present invention, a surfactant and water.

<CCE>

The preferred range of the content of CCE in the skin cleanser composition of the present invention is the same as the preferred range of the content of CCE in the above-mentioned surfactant composition.

From the viewpoint of giving an excellent moisturizing feeling after drying, CCE in the skin cleanser composition of the present invention preferably has MS(N+) of from 0.05 to 0.30, MS(Gly) of from 0.5 to 2.4 and MS(HC) of from 0.002 to 0.03, more preferably has MS(N+) of from 0.05 to 0.25, MS (Gly) of from 0.5 to 2.2 and MS(HC) of from 0.002 to 0.02.

<Surfactant>

The surfactant to be in the skin cleanser composition of the present invention may be any and every surfactant capable of being generally used in drugs, quasi-drugs, cosmetics, toiletry goods, sundries, etc. Their preferred embodiments are the same as the preferred embodiments of the surfactant described in the section of the surfactant composition mentioned above. From the viewpoint of giving an excellent moisturizing feeling after drying in use of the skin cleanser composition of the present invention, preferred are at least one selected from the anionic surfactants, the nonionic surfactants and the ampholytic surfactants described in the section of the surfactant composition mentioned above. The preferred embodiments of the anionic surfactants, the nonionic surfactants and the ampholytic surfactants are the same as those described in the section of the surfactant composition. Further, preferred are at least one selected from polyoxyethylene alkyl ether sulfates; higher fatty acids or their salts having from 8 to 16 carbon atoms; hydrophobic site-having sulfonate salts such as acyl isethionate, acylmethyl taurate, etc.; hydrophobic site-having amino acid salts such as cocoyl glycinate, lauroyl sarcosinate, etc.; fatty acid monoalkanolamides such as coconut oil fatty acid monoethanolamide, coconut oil fatty acid N-methylmonoethanolamide, etc.; fatty acid amide propylbetaines such as coconut oil fatty acid amide propylbetaine, etc.; imidazoline-type betaines such as Laurylcarboxymethylhydroxyimidazolium betaine, etc.

(Content of Surfactant)

The preferred embodiment of the content of the surfactant in the skin cleanser composition of the present invention is the same as that of the content of the surfactant described in the section of the surfactant composition mentioned above. From the viewpoint of giving an excellent moisturizing feeling after drying in use of the skin cleanser composition of the present invention, the surfactant content is preferably at least 5% by mass, more preferably at most 10% by mass. Also from the viewpoint of giving an excellent moisturizing feeling after drying in use of the skin cleanser composition of the present invention, the surfactant content is preferably from 5 to 36% by mass, even more preferably from 10 to 36% by mass.

(Ratio by Mass of CCE to Surfactant)

In the skin cleanser composition of the present invention, the preferred embodiment of the ratio by mass of CCE to the surfactant [CCE/surfactant] is the same as the preferred embodiment of the ratio by mass of CCE to the surfactant in the section of the surfactant composition mentioned above. From the viewpoint of the moisturizing feeling after skin washing with the skin cleanser composition of the present invention, the ratio is preferably at most 0.3, more preferably at most 0.05. Also from the viewpoint of the moisturizing feeling after skin washing with the skin cleanser composition of the present invention, the ratio is preferably from 0.005 to 0.3, more preferably from 0.005 to 0.05.

<Water>

The preferred embodiment of the water content in the skin cleanser composition of the present invention is the same as the preferred embodiment thereof described in the section of the surfactant composition mentioned above. From the viewpoint of giving a moisturizing feeling after skin washing with the skin cleanser composition of the present invention, the water content is preferably at most 95% by mass, more preferably at most 90% by mass. Also from the viewpoint of giving a moisturizing feeling after skin washing with the skin cleanser composition of the present invention, the water content is preferably from 40 to 95% by mass, more preferably from 40 to 90% by mass.

<Cationic Polymer Except CCE>

From the viewpoint of further improving the moisturizing feeling after washing with the skin cleanser composition of the present invention and drying, the skin cleanser composition of the present invention may contain any other cationic polymer than CCE. Specific examples and the preferred embodiment of the other cationic polymer than CCE are the same as the specific examples and the preferred embodiment of the other cationic polymer than CCE described in the section of the surfactant composition mentioned above. One alone or two or more different types of such other cationic polymers than CCE may be used here either singly or as combined. As the other cationic polymer than CCE, preferred are cationized guar gum and cationized hydroxyethyl cellulose.

The content of the other cationic polymer than CCE in the skin cleanser composition of the present invention, the ratio by mass of CCE to the other cationic polymer than CCE therein [CCE/other cationic polymer than CCE] and their preferred embodiments are the same as those described in the section of the surfactant composition mentioned above.

<Oily Agent>

From the viewpoint of giving a moist feeling and a moisturizing feeling after washing, the skin cleanser composition of the invention may contain an oily agent. Specific examples and the preferred embodiments of the oily agent are the same as the specific examples and the preferred embodiments thereof described in the section of the surfactant composition mentioned above. From the viewpoint of giving a moist feeling and a moisturizing performance after washing with the skin cleanser composition of the present invention, the oily agent is preferably at least one selected from ester oils, hydrocarbon oils, and carboxylic acids having a hydrocarbon group having from 17 to 23 carbon atoms and optionally substituted with a hydroxyl group; and more preferred are at least one selected from sunflower oil and vaseline.

(Content of Oily Agent)

The preferred embodiment of the content of the oily agent in the skin cleanser composition of the present invention is the same as the preferred embodiment of the content of the oily agent in the surfactant composition mentioned above. From the viewpoint of the excellent moist feeling and moisturizing performance after drying, the content of the oily agent is preferably at least 0.5% by mass, more preferably at least 2% by mass, even more preferably at least 4% by mass. Also from the viewpoint of giving an excellent moist feeling and an excellent moisturizing performance after drying, the content of the oily agent is preferably from 0.5 to 15% by mass, more preferably from 2 to 15% by mass, even more preferably from 4 to 15% by mass.

(Ratio by Mass of CCE to Oily Agent)

In the skin cleanser composition of the present invention, the preferred embodiment of the ratio by mass of CCE to the oily agent [CCE/oily agent] is the same as that of the ratio by mass of CCE to the oily agent in the surfactant composition. From the viewpoint of the excellent moist feeling and moisturizing performance after drying, the ratio by mass of CCE to the oily agent is preferably at most 0.3, more preferably at most 0.1, and is preferably from 0.01 to 0.3, more preferably from 0.01 to 0.1.

<Other Components>

Further, if desired, glycerin, moisturizers, polysaccharides, polypeptides, pearly agents, solvents, dyes, fragrances, chelating agents such as edates, citrates and the like, pH regulators, preservatives and others that may be generally incorporated in skin cleanser compositions may be suitably incorporated in the skin cleanser composition of the present invention.

The pH of the skin cleanser composition of the present invention is preferably from pH 2 to 12, more preferably from pH 3 to 10, from the viewpoint of providing the effects of the present invention.

The forms of the skin cleanser composition of the present invention are not specifically defined. The composition may be in any form of liquid, foam, paste, cream, solid, powder, etc. Preferred is liquid, paste or cream, and more preferred is liquid.

[Skin Washing Method]

The present invention also provides a skin washing method that comprises washing skin with the skin cleanser composition of the present invention, then rinsing and drying the skin.

The skin washing method is not specifically defined, to which any known method is applicable here.

Specific examples of the skin cleanser composition of the present invention include body shampoo, hand wash, face wash, and makeup remover. In consideration of the effects of the present invention, the composition is preferably used as body shampoo, hand wash or face wash.

[Hair Conditioner Composition]

The surfactant composition of the present invention is usable as a hair conditioner composition.

The hair conditioner composition of the present invention contains CCE of the present invention, a surfactant, an oily agent and water.

<CCE>

The preferred range of the content of CCE in the hair conditioner composition of the present invention is the same as the preferred range of the content of CCE in the above-mentioned surfactant composition.

From the viewpoint of giving a good presence in application of the composition to hair, giving an excellent smoothness feeling and its sustained feeling as well as softness in rinsing, and giving an excellent coated feeling after drying, CCE in the hair conditioner composition of the present invention preferably has MS(N+) of from 0.05 to 0.5, MS(Gly) of from 0.5 to 2.5 and MS(HC) of from 0.005 to 0.05, more preferably has MS(N+) of from 0.05 to 0.28, MS(Gly) of from 1.8 to 2.4 and MS(HC) of from 0.01 to 0.03, and even more preferably has MS(N+) of from 0.20 to 0.25, MS(Gly) of from 2.0 to 2.2 and MS(HC) of from 0.01 to 0.03.

In the present invention, the coated feeling means a feeling of the surface of hair likely coated with a filmy substance.

<Surfactant>

The surfactant to be in the hair conditioner composition of the present invention may be any and every surfactant capable of being generally used in drugs, quasi-drugs, cosmetics, toiletry goods, sundries, etc. Their preferred embodiments are the same as the preferred embodiments of the surfactant described in the section of the surfactant composition mentioned above. From the viewpoint of the good presence in application of the hair conditioner composition of the present invention to hair, the excellent smoothness feeling and its sustained feeling as well as softness in rinsing, and the excellent coated feeling after drying, preferred are the cationic surfactants described in the section of the surfactant composition mentioned above. The preferred embodiments of the nonionic surfactants are the same as those described in the section of the surfactant composition. Further, preferred are at least one selected from behenyltrimethylammonium salts and cetyltrimetylammonium salts.

(Content of Surfactant)

The preferred embodiment of the content of the surfactant in the hair conditioner composition of the present invention is the same as that of the content of the surfactant described in the section of the surfactant composition mentioned above. From the viewpoint of the good presence in application of the hair conditioner composition of the present invention to hair, the excellent smoothness feeling and smoothness sustainment, and the softness in rinsing, and the excellent coated feeling after drying, the content is preferably at most 20% by mass, more preferably at most 10% by mass. From the above-mentioned viewpoint, the surfactant content is preferably from 0.1 to 20% by mass, more preferably from 0.1 to 10% by mass.

(Ratio by Mass of CCE to Surfactant)

In the hair conditioner composition of the present invention, the preferred embodiment of the ratio by mass of CCE to the surfactant [CCE/surfactant] is the same as the preferred embodiment of the ratio by mass of CCE to the surfactant in the section of the surfactant composition mentioned above. From the viewpoint of the good presence in application of the hair conditioner composition of the present invention to hair, the excellent smoothness feeling and its sustained feeling as well as softness in rinsing, and the excellent coated feeling after drying, the ratio is preferably at least 0.05 and at most 1, and more preferably at most 0.5. Accordingly from the above-mentioned viewpoint, the ratio is more preferably from 0.05 to 1, even more preferably from 0.05 to 0.5.

<Water>

The preferred embodiment of the water content in the hair conditioner composition of the present invention is the same as the preferred embodiment thereof described in the section of the surfactant composition mentioned above. From the viewpoint of the good presence in application of the hair conditioner composition of the present invention to hair, the excellent smoothness feeling and its sustained feeling as well as softness in rinsing, and the excellent coat feeling after drying, the water content is at least 70% by mass, more preferably at least 80% by mass. Also from the viewpoint of the good presence in application of the hair conditioner composition of the present invention to hair, the excellent smoothness feeling and its sustained feeling as well as softness in rinsing, the water content is preferably from 70 to 99.5% by mass, more preferably from 80 to 99.5% by mass.

<Oily Agent>

From the viewpoint of giving a moist feeling, uniformity and a moisturizing performance to hair after drying, the hair conditioner composition of the present invention contains an oily agent. Specific examples and the preferred embodiments of the oily agent are the same as the specific examples and the preferred embodiments thereof described in the section of the surfactant composition mentioned above. From the viewpoint of giving a moist feeling and a moisturizing performance to hair after drying, the oily agent is preferably at least one selected from silicone oils and higher alcohols, and more preferably at least one selected from dimethylpolysiloxane, cetyl alcohol and stearyl alcohol.

(Content of Oily Agent)

The preferred embodiment of the content of the oily agent in the hair conditioner composition of the present invention is the same as the preferred embodiment of the content of the oily agent in the surfactant composition mentioned above. From the viewpoint of giving a moist feeling, uniformity and a moisturizing feeling to hair after drying, the content of the oily agent is preferably at most 10% by mass, more preferably at most 8% by mass, and is preferably from 0.1 to 10% by mass, more preferably from 0.1 to 8% by mass.

(Ratio by Mass of CCE to Oily Agent)

In the hair conditioner composition of the present invention, the preferred embodiment of the ratio by mass of CCE to the oily agent [CCE/oily agent] is the same as that of the ratio by mass of CCE to the oily agent in the surfactant composition.

<Other Components>

Further, if desired, glycerin, moisturizers, polysaccharides, polypeptides, pearly agents, solvents, dyes, fragrances, chelating agents such as edates, citrates and the like, pH regulators, preservatives and others that may be generally incorporated in hair conditioner compositions may be suitably incorporated in the hair conditioner composition of the present invention.

<pH>

From the viewpoint of the presence in application of the composition to hair, the smoothness feeling and its sustained feeling in rinsing, and the coat feeling after drying, the pH of the hair conditioner composition of the present invention is preferably at least pH 1, more preferably at least pH 2, even more preferably at least pH 3, and is preferably at most pH 10, more preferably at most pH 8, and even more preferably at most pH 6. Accordingly from the above-mentioned viewpoint, the pH is preferably from 1 to 10, more preferably from 2 to 8, even more preferably from 3 to 6.

The forms of the hair conditioner composition of the present invention are not specifically defined. The composition may be in any form of liquid, foam, paste, cream, solid, powder, etc. Preferred is liquid, paste or cream, and more preferred is liquid.

[Hair Conditioning Method]

The hair conditioning method with the hair conditioner composition of the present invention is not specifically defined, to which any known method is applicable here. For example, hair is washed with a detergent, and then the conditioner composition of the present invention may be applied to the washed hair. As the detergent, usable is any known hair wash as well as the hair wash composition of the present invention.

Specific examples of the hair conditioner composition of the present invention include hair rinse, treatment, hair conditioner, leave-in hair conditioner, hair cream, conditioner gel, conditioner foam, etc.

[Hair Treatment Composition]

The hair treatment composition of the present invention is meant to indicate a treatment composition in the broad sense of the term, including a hair color composition, a hair bleach composition, a perm wave composition, a straight perm composition, a sustainable hair styling composition, a hair relaxer composition, etc.

The hair treatment composition of the present invention contains CCE, as well as at least one treatment agent selected from hair-coloring dyes, oxidizing agents, alkali agents and keratin-reducing agents.

Containing CCE, the hair treatment composition of the present invention gives a smoothness property, a good coat feeling and softness to hair in rinsing.

Typical embodiments of the hair treatment composition of the present invention include a hair color composition and a perm composition. "Hair color composition" is a concept including both a colorant-containing hair color composition and a colorant-free hair breach composition, further including a composition that bleaches and colors hair. "Perm composition" is a concept including a perm wave composition, a straight perm composition and a hair relaxer composition.

<CCE>

CCE in the hair treatment composition of the present invention preferably has, from the viewpoint of giving a smoothness property, a good coat feeling and softness to hair in rinsing after treatment when the treatment agent is used as a hair color composition, MS(N+) of from 0.05 to 0.32, MS(Gly) of from 0.6 to 2.3 and MS(HC) of from 0.001 to 0.05, more preferably has MS(N+) of from 0.11 to 0.32, MS(Gly) of from 0.7 to 2.0 and MS(HC) of from 0.002 to 0.03.

The CCE content in the hair treatment composition of the present invention is, from the viewpoint of giving a smoothness property, a good coat feeling and softness to hair in rinsing after treatment, for example, when the treatment composition is sued as a hair color composition, preferably at least 0.01% by mass, more preferably at least 0.05% by mass, and from the viewpoint of the handleability of the hair treatment composition, the CCE content is preferably at most 10% by mass, more preferably at most 2% by mass, even more preferably at most 1% by mass. Accordingly from the above-mentioned viewpoint, the CCE content in the hair treatment composition of the present invention is preferably from 0.01 to 10% by mass, more preferably from 0.05 to 2% by mass, even more preferably from 0.05 to 1% by mass.

In case where the hair treatment composition is a multi-pack composition in which two or more packs are mixed before use, it is desirable that CCE is incorporated in the first pack from the viewpoint of giving a smootheness property, a good coat feeling and softness to hair in rinsing after treatment.

From the viewpoint of giving a smootheness property, a good coat feeling and softness to hair in rinsing after treated with the hair treatment composition of the present invention, the ratio by mass of CCE to the treatment agent [CCE/treatment agent] in the hair treatment composition of the present invention is preferably at least 0.0002, more preferably at least 0.002, and is preferably at most 5, more preferably at most 3 even more preferably at most 1, still more preferably at most 0.1.

<Hair-Coloring Dye>

A hair-coloring dye may be incorporated in the hair treatment composition such as a hair color composition, etc.

The hair-coloring dye includes a direct dye and an oxidation dye intermediate.

Not specifically defined, the direct dye for use herein may be any and every one generally used in cosmetics and the like, including nitro dyes, anthraquinone dyes, acidic dyes, oil-soluble dyes, basic dyes, etc.

Specific examples of those dyes are described in WO2011/040632. One or more those direct dyes may be used here either singly or as combined.

The content of the direct dye in the hair treatment composition is, from the viewpoint of the dye stainability on hair, preferably at least 0.005% by mass in the hair treatment composition, more preferably at least 0.01% by mass, and is preferably at most 10% by mass, more preferably at most 5% by mass. Accordingly, the content of the direct dye in the hair treatment composition is, from the viewpoint of the dye stainability on hair, preferably from 0.005 to 10% by mass, more preferably from 0.01 to 5% by mass.

As the oxidation dye intermediate, usable here are known precursors and couplers generally used in hair colors.

Specific examples of precursors and couplers are described in WO2011/040632. One alone or two or more different types of those oxidation dye intermediates may be used here either singly or as combined.

The content of the oxidation dye intermediate is, from the viewpoint of the dye stainability on hair, preferably at least 0.01% by mass in the hair treatment composition, more preferably at least 0.1% by mass, and is preferably at most 10% by mass, more preferably at most 5% by mass.

<Oxidizing Agent>

An oxidizing agent may be incorporated in the hair treatment composition such as a hair color composition, a perm composition, etc.

The oxidizing agent includes hydrogen peroxide, as well as a generator to generate hydrogen peroxide or oxygen, such as urea peroxide, melamine peroxide, sodium perborate, potassium perborate, sodium percarbonate, potassium carbonate or the like percarbonate, and potassium bromate, sodium bromate or the like bromate salt.

One alone or two or more different types of the above agents may be used here either singly or as combined.

The content of the oxidizing agent in the hair treatment composition is, from the viewpoint of the hair-coloring performance and the hair-bleaching performance when used in a hair color composition and from the viewpoint of the capability of efficiently recombining the broken disulfide bonds in the hair keratin when used in a perm composition, preferably at least 0.1% by mass, more preferably at least 0.5% by mass. On the other hand, from the viewpoint of reducing hair damage and scalp irritation, the content of the oxidizing agent is preferably at most 20% by mass, more preferably at most 12% by mass.

<Alkali Agent>

An alkali agent may be incorporated in the hair treatment composition such as a hair color composition, a perm composition, etc.

The alkali agent includes sodium hydroxide, ammonia and its salts; alkanolamines and their salts such as monoethanolamine, isopropanolamine, 2-amino-2-methylpropanol, 2-aminobutanol, etc.; alkanediamines and their salts such as 1,3-propanediamine, etc.; carbonates such as guanidine carbonate, sodium carbonate, potassium carbonate, sodium hydrogencarbonate, potassium hydrogencarbonate, etc. From the viewpoint of the hair-coloring performance and the hair-bleaching performance when the hair treatment composition is used as a hair color composition, and from the viewpoint the improved keratin-reducing performance when used as a perm composition, the alkali agent is preferably at least one selected from ammonia and its salts, alkanolamines and their salts and sodium hydrogencarbonate.

From the viewpoint of the hair-coloring performance and the hair-bleaching performance when the hair treatment composition is used as a hair color composition, from the viewpoint the improved keratin-reducing performance when used as a perm composition, from the viewpoint of the curling sustainability after treatment and from the viewpoint of reducing hair damage and scalp irritation, the content of the alkali agent is preferably from 0.1% by mass to 10% by mass.

<Keratin-Reducing Agent>

A keratin-reducing agent may be incorporated in the hair treatment composition such as a perm composition, etc. The keratin-reducing agent can cleave the disulfide bonds in keratin that constitute hair. The hair treatment composition that contains the keratin-reducing agent of the type is preferably used as the first perm wave agent in the perm composition.

The keratin-reducing agent includes thioglycolic acid and its derivatives, thiolactic acid and its derivatives, cysteine and its derivatives, as well as their salts, and thioglyceryl alkyl ethers of the following formula (23), mercaptoalkyl-amides of the following formula (24), and their salts.

$$R^{38}OCH_2CH(OH)CH_2SH \quad (23)$$

(In the formula, $R^{38}$ represents a hydrogen atom, a lower alkyl group or a lower alkoxy-lower alkyl group.)

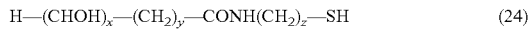

$$H-(CHOH)_x-(CH_2)_y-CONH(CH_2)_z-SH \quad (24)$$

(In the formula, x indicates a number of from 0 to 5, y indicates a number of from 0 to 3, z indicates a number of from 2 to 5; however, y and z are not 0 at the same time.)

Specific examples of the keratin-reducing agent include thioglycolic acid, ammonium thioglycolate, glycerin thioglycolate ester, L-cysteine, D-cysteine, N-acetylcysteine, ammonium salts of those cysteines; ethanolamine salts such as monoethanolamine salt, diethanolamine salt, triethanolamine salt or the like of those cysteines; thioglyceryl alkyl ethers such as ethoxyhydroxypropanethiol, methoxyethoxyhydroxypropanethiol, isopropoxyethoxyhydroxypropanethiol, etc.; mercaptoethylpropanamide, mercaptoethylgluconamide, etc.

One alone or two or more different types of those keratin-reducing agents may be used here either singly or as combined.

From the viewpoint of cleaning the disulfide bonds in hair-constituting keratin and from the viewpoint of securing good perming performance in finish, the content of the keratin-reducing agent is preferably at least 0.1% by mass in the hair treatment composition, more preferably at least 1% by mass. Also from the same viewpoint as above, the content of the keratin-reducing agent is preferably at most 20% by mass in the hair treatment composition, more preferably at most 15% by mass, even more preferably at most 10% by mass.

<Water>

The hair treatment composition of the present invention contains CCE and preferably water as the solvent or the dispersant for the treatment agent therein. Preferably the water content in the hair treatment composition is from 10% by mass to 99.5% by mass.

<Surfactant>

The hair treatment composition of the present invention may contain a surfactant for the purpose of improving the smoothness property, the coat feeling and the softness of hair in rinsing after treatment. The concrete type of the surfactant, the content of the surfactant and the preferred embodiments thereof are the same as those described in the section of the surfactant composition given hereinabove. From the viewpoint of the smoothness property, the coat feeling and the softness of hair in rinsing after treatment, the content of the surfactant in the hair treatment composition of the present invention is preferably at least 1% by mass and is preferably at most 20% by mass, more preferably at most 10% by mass, even more preferably at most 5% by mass.

<Oily Agent>

The hair treatment composition of the present invention may contain an oily agent for the purpose of improving the smoothness property, the coat feeling and the softness of hair in rinsing after treatment. The concrete type of the oily agent, the content of the oily agent and the preferred embodiments thereof are the same as those described in the section of the surfactant composition given hereinabove.

In case where the hair treatment composition is a multi-pack composition in which two or more packs are mixed before use, the preferred content of CCE, the treatment agent, the surfactant or the oily agent therein means the preferred content of CCE, the treatment agent, the surfactant or the oily agent relative to the total amount of each agent in all packs constituting the composition.

<Other Components>

Further, if desired, glycerin, moisturizers, polysaccharides, polypeptides, pearly agents, solvents, dyes, fragrances, chelating agents such as edates, citrates and the like, pH regulators, preservatives, anti-dandruff agents such as zinc pyrithione, piroctone olamine and the like that may be generally incorporated in hair treatment compositions may be suitably incorporated in the hair treatment composition of the present invention.

<Method for Producing Hair Treatment Composition>

The method for producing the hair treatment composition of the present invention is not specifically defined, and the composition may be produced according to an ordinary method. Concretely, for example, water, CCE and treatment agents except oxidizing agent and alkali agent, and other components are mixed and uniformly dissolved under heat. After the dissolution has been confirmed, oxidizing agent and alkali agents are added and further mixed.

If desired, CCE may be previously dispersed or dissolved in water before added to the composition. Further if desired, a pearly agent, a pH regulator, a fragrance, a dye and the like may be added to the composition.

The forms of the hair treatment composition of the present invention are not specifically defined. The composition may be in any form of liquid, foam, paste, cream, solid, powder, etc. Preferred is liquid, paste or cream, and more preferred is liquid.

[Hair Treatment Method]

The hair treatment method with the hair treatment composition of the present invention is not specifically defined, to which any known method is applicable here. For example, the hair treatment composition of the present invention may be brought into contact with hair to treat the hair, and then the hair may be rinsed and dried for the intended treatment.

<Hair Color Composition>

In case where the hair treatment composition of the present invention is a hair color composition, the hair color composition contains CCE, and at least one or more treatment agents selected from a hair-coloring dye, an oxidizing agent and an alkali agent. Embodiments of the hair treatment composition of the present invention as a hair color composition are described below.

The hair color composition includes, for example, a one-pack hair color composition of the following (a) and (b), and a multi-pack hair color composition of the following (c) and (d).

(a) One-pack hair color composition containing a hair-coloring dye and optionally an oxidizing agent.

(b) One-pack hair color composition not containing a hair-coloring dye but containing an oxidizing agent.

(c) Two-pack hair color composition composed of a first pack containing an alkali agent and/or a hair-coloring dye, and a second pack containing an oxidizing agent.

(d) Three-pack hair color composition composed of a first pack containing an alkali agent and/or a hair-coloring dye, a second pack containing an oxidizing agent, and a third pack containing an oxidation promoter.

In the above two-pack hair color composition (c), the content ratio (by mass) of the first pack to the second [first pack/second pack] is preferably from 2/8 to 6/4, more preferably from 3/7 to 5/5, even more preferably from 3.5/6.5 to 4.5/5.5.

The hair color composition may be applicable to any form of one to be used at room temperature or one to be used under heat.

(CCE)

In case where the hair treatment composition of the present invention is a hair color composition, the preferred range of the content of CCE is the same as the preferred range of the content of CCE for use in the above-mentioned hair treatment composition.

In case where the hair treatment composition is a hair color composition, the ratio by mass of CCE to the treatment agent [CCE/treatment agent] is the same as the ratio by mass of CCE to the treatment agent in the above-mentioned hair treatment agent. From the viewpoint of securing the smootheness property, coat feeling and softness in rinsing after treatment with the hair treatment agent of the present invention, the ratio by mass of CCE to the treatment agent [CCE/treatment agent] is preferably at most 1, more preferably at most 0.1.

(Hair-Coloring Dye)

Specific examples, the content and their preferred ranges of the hair-coloring dye for use in the hair color composition of the present invention are the same as the specific examples, the content and their preferred ranges of the hair-coloring dye for use in the above-mentioned hair treatment composition.

In case where the hair color composition is for bleaching hair, the hair color composition may not contain a hair-coloring dye.

(Oxidizing Agent)

Specific examples, the content and their preferred ranges of the oxidizing agent for use in the hair color composition of the present invention are the same as the specific examples, the content and their preferred ranges of the oxidizing agent for use in the above-mentioned hair treatment composition. From the viewpoint of the dye stainability on hair, the oxidizing agent is preferably hydrogen peroxide, or a hydrogen peroxide or oxygen generator of urea peroxide, melamine peroxide, sodium perborate, potassium perborate, sodium percarbonate or potassium percarbonate, and more preferably hydrogen peroxide. One alone or two or more different types of those oxidizing agents may be used here either singly or as combined.

The preferred range of the oxidizing agent content in the hair color composition is the same as the preferred range of the oxidizing agent content in the above-mentioned hair treatment composition. From the viewpoint of reducing hair damage and scalp irritation, the content of the oxidizing agent is preferably at most 9% by mass, and from the viewpoint of the dye stainability on hair, the oxidizing agent content is preferably at least 2% by mass.

(Alkali Agent)

Specific examples and their preferred ranges of the alkali agent for use in the hair color composition of the present invention are the same as the specific examples and their preferred ranges of the alkali agent for use in the above-mentioned hair treatment composition. From the viewpoint of the dye stainability on hair and the bleaching performance, the alkali agent is preferably ammonia, alkanolamines and their salts. One alone or two or more different types of these agents may be used here either singly or as combined.

The preferred range of the alkali agent content in the hair color composition is the same as the preferred range of the alkali agent content in the above-mentioned hair treatment composition.

(Water)

In case where the hair treatment composition of the present invention is a hair color composition, it is also desirable that the composition contains water. The preferred range of the water content is the same as the preferred range of the water content in the above-mentioned hair treatment composition.

(Surfactant)

The hair color composition of the present invention may contain a surfactant for the purpose of improving the smootheness property, the coat feeling and the softness of hair in rinsing after treatment. The concrete type of the surfactant and the preferred embodiments thereof are the same as those described in the section of the hair treatment composition given hereinabove. From the viewpoint of the improved smootheness property, coat feeling and softness of hair in rinsing, the surfactant is preferably an anionic surfactant or a nonionic surfactant, and is more preferably a polyoxyethylene alkyl ether sulfate such as sodium polyoxyethylene lauryl ether sulfate (sodium laureth-2 sulfate), etc., or a polyoxyethylene alkyl ether such as polyoxyethylene lauryl ether, polyoxyethylene cetostearyl ether or the like.

In case where the hair color composition contains a surfactant, the preferred range of the surfactant therein is the same as the preferred range of the content of the surfactant in the above-mentioned, surfactant-containing hair treatment composition.

(Oily Agent)

The hair color composition of the present invention may contain an oily agent for the purpose of improving the smoothness property, the coat feeling and the softness of hair in rinsing after treatment. The concrete type of the oily agent and its preferred embodiments are the same as those described in the section of the above-mentioned hair treatment composition. From the viewpoint of improving the smoothness property, the coat feeling and the softness of hair in rinsing after treatment, the oily agent is preferably a higher alcohol and is more preferably at least one selected from lauryl alcohol, myristyl alcohol, cetyl alcohol, stearyl alcohol, behenyl alcohol and 2-octyldodecanol.

In case where the hair color composition contains an oily agent, the preferred range of the content of the oily agent therein is the same as the preferred range of the oily agent in the above-mentioned, oily agent-containing hair treatment composition. From the viewpoint of improving the smoothness property, the coat feeling and the softness of hair in rinsing after treatment, the content of the oily agent is preferably at least 1% by mass and at most 10% by mass, and is more preferably at most 5% by mass.

(pH)

The pH of the hair color composition of the invention is, when the composition is a one-pack composition, preferably from pH 3 to 9 for the purpose of preventing skin and hair damage. In case where the composition is a two-pack hair color composition, the pH of the first pack is preferably from pH 8 to 13, and the pH of the second pack is preferably from pH 2 to 5. In case where the composition is a three-pack hair color composition, the pH of the first pack is preferably from pH 8 to 13, and the pH of the second pack is preferably from pH 2 to 5. The pH control may be attained by the use of a known pH regulator.

(Other Components)

The hair color composition may contain any other component as described in the section of the other components for the above-mentioned hair treatment composition.

<Perm Composition>

In case where the hair treatment composition of the present invention is a perm composition, the perm composition contains CCE and contains a keratin-reducing agent, an oxidizing agent and an alkali agent as treatment agents. Embodiments of the hair treatment composition of the present invention as a perm composition are described below.

The perm composition is a two-pack composition composed of a first pack that contains a keratin-reducing agent, and a second pack that contains an oxidizing agent.

In the perm composition, the ratio (by mass) to be used of the first pack to the second pack [first pack/second pack] is preferably from 3/7 to 7/3, more preferably from 4/6 to 6/4, even more preferably from 4.5/5.5 to 5.5/4.5.

The perm composition is applicable to any form of one to be used at room temperature, one to be used under heat, one to be used for wave formation, one to be used for hair relaxation, etc.

(CCE)

The preferred range of the content of CCE in the perm composition is the same as the preferred range of the content of CCE to be used in the above-mentioned hair treatment composition.

From the viewpoint of imparting a smoothness property, a coat feeling and softness to hair in rinsing after treatment, CCE is preferably incorporated in the first pack.

(Keratin-Reducing Agent)

Specific examples of the type of the keratin-reducing agent in the perm composition and the preferred range thereof, and the preferred range of the content of the keratin-reducing agent in the composition are the same as those in the above-mentioned hair treatment composition.

(Oxidizing Agent)

In the perm composition, the oxidizing agent is incorporated in the second pack. Specific examples and their preferred ranges of the oxidizing agent for use in the perm composition are the same as the specific examples and their preferred ranges of the oxidizing agent for use in the above-mentioned hair treatment composition.

From the viewpoint of sufficiently recombining the broken disulfide bonds in the hair keratin, the oxidizing agent is preferably at least one selected from potassium bromate, sodium bromate, sodium perborate and hydrogen peroxide, and is more preferably at least one selected from potassium bromate, sodium bromate and hydrogen peroxide. One alone or two or more different types of oxidizing agents may be used here either singly or as combined.

The preferred range of the content of the oxidizing agent in the perm composition is the same as the preferred range of the oxidizing agent for use in the above-mentioned hair treatment composition. From the viewpoint of sufficiently recombining the broken disulfide bonds in the hair keratin, and from the viewpoint of reducing hair damage and scalp irritation, the content of the oxidizing agent in the perm composition is preferably at least 1% by mass, more preferably at least 2% by mass and is preferably at most 10% by mass, more preferably at most 5% by mass.

(Alkali Agent)

Specific examples and their preferred ranges of the alkali agent for use in the perm composition are the same as the specific examples and their preferred ranges of the alkali agent for use in the above-mentioned hair treatment composition.

The preferred range of the alkali agent content in the perm composition is the same as the preferred range of the alkali agent content in the above-mentioned hair treatment composition. From the viewpoint of reducing hair damage and scalp irritation, the content is more preferably at most 5% by mass.

(pH)

For reducing skin and hair damage, the pH of the first pack of the perm composition is preferably from pH 6 to 12, and the pH of the second pack thereof is preferably from pH 3 to 9. The pH control may be attained by the use of a known pH regulator.

(Water)

In case where the hair treatment composition of the present invention is a perm composition, it is also desirable that the composition contains water. The preferred range of the water content is the same as the preferred range of the water content in the above-mentioned hair treatment composition.

(Surfactant)

The perm composition may contain a surfactant for the purpose of improving the smoothness property, the coat feeling and the softness of hair in rinsing after treatment. Concrete types and their preferred embodiments of the surfactant are the same as those described in the section of the above-mentioned hair treatment composition. From the viewpoint of improving the smoothness property, the coat feeling and the softness of hair in rinsing, the surfactant is preferably an anionic surfactant or a nonionic surfactant, and more preferably a polyoxyethylene alkyl ether sulfate such as sodium polyoxyethylene lauryl ether sulfate (sodium laureth-2 sulfate), etc., or a polyoxyethylene alkyl ether such as polyoxyethylene lauryl ether, polyoxyethylene cetostearyl ether or the like.

In case where the perm composition contains a surfactant, the preferred range of the surfactant therein is the same as the preferred range of the content of the surfactant in the above-mentioned, surfactant-containing hair treatment composition.

(Other Components)

The perm composition may contain, in addition to the oily agent therein, any other component such as those described in the section of the other components for the above-mentioned hair treatment composition.

Relating to the above-mentioned embodiments thereof, the present invention discloses a cationic group-containing cellulose ether, and a surfactant composition, a hair wash composition, a hair cleanser composition, a hair conditioner composition and a hair treatment composition containing the cellulose ether, which are described below.

<1> A cationic group-containing cellulose ether, which has a main chain derived from an anhydroglucose represented by the following general formula (1), and in which the degree of substitution with a cationized oxyalkylene group per the anhydroglucose unit is from 0.01 to 1.0, the degree of substitution with a glycerol group is from 0.5 to 5.0, and the degree of substitution with a group that contains a branched hydrocarbon group having from 8 to 18 carbon atoms, preferably from 8 to 16 carbon atoms, more preferably from 8 to 14 carbon atoms and even more preferably from 8 to 12 carbon atoms, and is represented by any of the following general formulae (6) to (8) is from 0.001 to 0.2:

[Chem. 9]

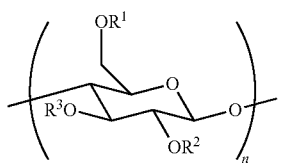
(1)

(In the formula, $R^1$, $R^2$ and $R^3$ each independently represent a substituent comprising at least one structural unit selected from the following formulae (2) to (8), or a hydrogen atom. n indicates a mean degree of polymerization of the anhydroglucose-derived main chain, and is a number of from 100 to 12000.)

[Chem. 10]

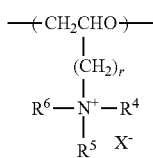
(2)

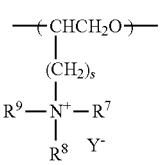
(3)

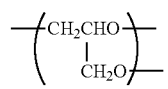
(4)

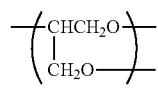
(5)

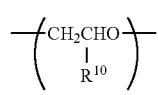
(6)

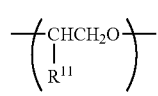
(7)

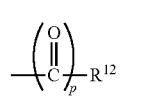
(8)

(In these formulae, the structural unit represented by the formula (2) or (3) is a cationized oxyalkylene group; the structural unit represented by the formula (4) or (5) is a glycerol group; and the structural unit represented by any of the formulae (6) to (8) is a group that contains a branched hydrocarbon group having from 8 to 18 carbon atoms, preferably from 8 to 16 carbon atoms, more preferably from 8 to 14 carbon atoms, even more preferably from 8 to 12 carbon atoms. $R^4$ to $R^9$ each independently represent a linear or branched alkyl group having from 1 to 3 carbon atoms; $X^-$ and $Y^-$ each represent an anion; and r and s each indicate an integer of from 0 to 3. $R^{10}$ and $R^{11}$ each independently represent a branched hydrocarbon group having from 6 to 16 carbon atoms. $R^{12}$ represents a branched hydrocarbon group having from 8 to 18 carbon atoms; and p indicates an integer of 0 or 1. In the structural unit represented by any of the formulae (2) to (7), the oxygen atom bonds to a hydrogen atom or to the carbon atom of the above-mentioned structural unit.)

<2> The cationic group-containing cellulose ether according to the above <1>, of which the cation charge density is preferably at least 0.05 mmol/g, more preferably at least 0.15 mmol/g, even more preferably at least 0.2 mmol/g, still more preferably at least 0.3 mmol/g, and is preferably at most 2.0 mmol/g, more preferably at most 1.7 mmol/g, even more preferably at most 1.5 mmol/g, still more preferably at most 1.2 mmol/g, further more preferably at most 1.0 mmol/g, even further more preferably at most 0.9 mmol/g.

<3> The cationic group-containing cellulose ether according to the above <1> or <2>, wherein the degree of substitution with a cationized oxyalkylene group per the anhydroglucose unit (MS(N+)) is preferably at least 0.05, more preferably at least 0.08, even more preferably at least 0.11, still more preferably at least 0.16, further more preferably at least 0.18, still further preferably at least 0.20, and is preferably at most 0.9, more preferably at most 0.7, even more preferably at most 0.5, still more preferably at most 0.35, further more preferably at most 0.32, even further preferably at most 0.28, still further preferably at most 0.25.

<4> The cationic group-containing cellulose ether according to any of the above <1> to <3>, wherein the degree of substitution with a glycerol group per the anhydroglucose unit (MS(Gly)) is preferably at least 0.6, more preferably at least 0.7, even more preferably at least 1.2, still more preferably at least 1.6, further more preferably at least 1.8, still further more preferably at least 2.0, and is preferably at most 4.0, more preferably at most 3.5, even more preferably at most 3.0, still more preferably at most 2.5, furthermore preferably at most 2.4, still further more preferably at most 2.3, even further more preferably at most 2.2.

<5> The cationic group-containing cellulose ether according to any of the above <1> to <4>, wherein the degree of substitution with a group containing a branched hydrocarbon group with from 8 to 18 carbon atoms per the anhydroglucose unit (MS(HC)) is preferably at least 0.002, more preferably at least 0.005, even more preferably at least 0.01, and is preferably at most 0.15, more preferably at most 0.10, even more preferably at most 0.08, still more preferably at most 0.06, further more preferably at most 0.05, still further preferably at most 0.04, even further more preferably at most 0.03.

<6> The cationic group-containing cellulose ether according to any of the above <1> to <5>, of which the mean degree of polymerization, n is preferably at least 200, more preferably at least 500, even more preferably at least 1000, and is preferably at most 10000, more preferably at most 5000, even more preferably at most 2500.

<7> The cationic group-containing cellulose ether according to any of the above <1> to <6>, wherein in the formulae (2) and (3), preferably, $R^4$ to $R^9$ each are a methyl group, an ethyl group, an n-propyl group or an isopropyl group, more preferably a methyl group or an ethyl group, even more preferably a methyl group.

<8> The cationic group-containing cellulose ether according to any of the above <1> to <7>, wherein in the formulae (2) and (3), preferably, $X^-$ and $Y^-$ each are at least one selected from an alkyl sulfate ion having from 1 to 3 carbon atoms, a sulfate ion, a phosphate ion, a fatty acid ion having from 1 to 3 carbon atoms, and a halide ion, more preferably at least one selected from an alkyl sulfate ion having from 1 to 3 carbon atoms, a sulfate ion and a halide ion, even more preferably a halide ion, still more preferably at least one selected from a chloride ion and a bromide ion, further more preferably a chloride ion.

<9> The cationic group-containing cellulose ether according to any of the above <1> to <8>, wherein the branched hydrocarbon group having from 8 to 18 carbon atoms is preferably a structural unit represented by the above-mentioned general formula (8), more preferably p is 0.

<10> The cationic group-containing cellulose ether according to any of the above <1> to <9>, wherein in the formula (8), preferably, $R^{12}$ is a branched alkyl or alkenyl group having from 8 to 18 carbon atoms, more preferably a branched alkyl or alkenyl group having from 8 to 16 carbon atoms, even more preferably a branched alkyl or alkenyl group having form 8 to 14 carbon atoms, still more preferably a branched alkyl group having from 8 to 12 carbon atoms, further more preferably a 2-ethylhexyl group or an isodecyl group.

<11> The cationic group-containing cellulose ether according to any of the above <1> to <8>, wherein in the formulae (6) and (7), preferably, $R^{10}$ and $R^{11}$ each are a branched alkyl or alkenyl group having from 6 to 16 carbon atoms, more preferably a branched alkyl or alkenyl group having from 6 to 14 carbon atoms, even more preferably a branched alkyl or alkenyl group having from 6 to 12 carbon atoms, still more preferably a branched alkyl group having from 6 to 12 carbon atoms.

<12> The cationic group-containing cellulose ether according to any of the above <1> to <10>, wherein the group having a branched hydrocarbon group with from 8 to 18 carbon atoms is preferably a branched alkyl or alkenyl group having from 8 to 14 carbon atoms, more preferably a branched alkyl or alkenyl group having from 8 to 12 carbon atoms, even more preferably a branched alkyl group having from 8 to 12 carbon atoms, still more preferably a 2-ethylhexyl group or an isodecyl group, further more preferably a 2-ethylhexyl group.

<13> The cationic group-containing cellulose ether according to any of the above <1> to <12>, of which the viscosity of the 1 mass % aqueous solution at 25° C. is preferably at least 10 mPa·s, more preferably at least 20 mPa·s, even more preferably at least 50 mPa·s, still more preferably at least 100 mPa·s, and is preferably at most 10000 mPa·s, more preferably at most 5000 mPa·s, even more preferably at most 3000 mPa·s, still more preferably at most 2000 mPa·s.

<14> A method for producing a cationic group-containing cellulose ether of any of the above <1> to <13>, which includes reacting a starting cellulose with a cationizing agent, a glycerolating agent, and a reagent for introducing a group that contains a branched hydrocarbon group having from 8 to 18 carbon atoms, and in which, preferably, the glycerolation reaction is first and followed by the cationization reaction and the reaction of introducing the group that contains a branched hydrocarbon group having from 8 to 18 carbon atoms in that order.

<15> The method for producing a cationic group-containing cellulose ether according to the above <14>, which is any of the following methods (i) to (iii):

Method (i): A method in which a starting cellulose is mixed with a large amount of water and with a large excessive amount of an alkali metal hydroxide to give an alkali cellulose, and thereafter this is reacted with a glycerolating agent, a cationizing agent, and a reagent for introducing a group that contains a branched hydrocarbon group having from 8 to 18 carbon atoms.

Method (ii): A method in which a starting cellulose is dissolved in a solvent capable of dissolving cellulose and selected from tetrabutylammonium fluoride-containing dimethyl sulfoxide, paraformaldehyde-containing dimethyl sulfoxide, and lithium chloride-containing dimethylacetamide or the like, and thereafter the starting cellulose is reacted with a glycerolating agent, a cationizing agent and a reagent for introducing a group that contains a branched hydrocarbon group having from 8 to 18 carbon atoms.

Method (iii): A methodnot using any excess alkali or specific solvent capable of dissolving cellulose, in which a powdery or floc-like starting cellulose is reacted with a glycerolating agent, a cationizing agent and a reagent for introducing a group that contains a branched hydrocarbon group having from 8 to 18 carbon atoms, in the presence of an alkali.

<16> The method for producing a cationic group-containing cellulose ether according to the above <14> or <15>, wherein the glycerolating agent is at least one selected from glycidol, 3-halo-1,2-propanediol, glycerin and glycerin carbonate, preferably glycidol.

<17> The method for producing a cationic group-containing cellulose ether according to any of the above <14> to <16>, wherein the amount of the glycerolating agent to be used is preferably at least 0.2 mols relative to one mol of the anhydroglucose unit in the starting cellulose, more preferably at least 1 mol, even more preferably at least 3 mols, still more preferably at least 4 mols, and is preferably at most 60 mols, more preferably at most 50 mols, even more preferably at most 45 mols, still more preferably at most 40 mols.

<18> The method for producing a cationic group-containing cellulose ether according to any of the above <14> to <17>, wherein the cationizing agent is preferably a compound represented by the above-mentioned general formula (9) or (10), more preferably at least one selected from glycidyltrimethylammonium, glycidyltriethylammonium and glycidyltripropylammonium chlorides, bromides and iodides, 3-chloro-2-hydroxypropyltrimethylammonium, 3-chloro-2-hydroxypropyltriethylammonium and 3-chloro-2-hydroxytripropylammonium chlorides, 3-bromo-2-hydroxypropyltrimethylammonium, 3-bromo-2-hydroxypropyltriethylammonium and 3-bromo-2-hydroxypropyltripropylammonium bromides, 3-iodo-2-hydroxypropyltrimethylammonium, 3-iodo-2-hydroxypropyltriethylammonium and 3-iodo-2-hydroxypropyltripropylammonium iodides, even more preferably at least one selected from glycidyltrimethylammonium and glycidyltriethylammonium chlorides and bromides, 3-chloro-2-hydroxypropyltrimethylammonium and 3-chloro-2-hydroxypropyltriethylammonium chlorides, and 3-bromo-2-hydroxypropyltrimethylammonium and 3-bromo-2-hydroxypropyltriethylammonium bromides, still more preferably at least one selected from glycidyltrimethylammonium chloride and 3-chloro-2-hydroxypropyltrimethylammonium chloride, further more preferably glycidyltrimethylammonium chloride.

<19> The method for producing a cationic group-containing cellulose ether according to any of the above <14> to <18>, wherein the amount of the cationizing agent to be used is preferably at least 0.01 mols relative to 1 mol of AGU in the starting cellulose, more preferably at least 0.03 mols, even more preferably at least 0.05 mols, still more preferably at least 0.1 mols, and is preferably at most 30 mols, more preferably at most 25 mols, even more preferably at most 10 mols.

<20> The method for producing a cationic group-containing cellulose ether according to any of the above <14> to <19>, wherein the reagent for introducing a group that contains a branched hydrocarbon group having from 8 to 18 carbon atoms is preferably a compound represented by any of the above-mentioned general formulae (11) and (12), more preferably a compound represented by the general formula (11)

<21> The method for producing a cationic group-containing cellulose ether according to any of the above <14> to <19>, wherein the reagent for introducing a group that contains a branched hydrocarbon group having from 8 to 18 carbon atoms is preferably a compound represented by any of the above-mentioned general formulae (13), (14) and (15), more preferably a compound represented by the general formula (14), even more preferably a glycidyl ether having a branched alkyl group with from 8 to 18 carbon atoms, still more preferably a glycidyl ether having a branched alkyl group with from 8 to 14 carbon atoms, further more preferably a glycidyl ether having a branched alkyl group with from 8 to 12 carbon atoms, still more preferably at least one selected from 2-ethylhexyl glycidyl ether and isodecyl glycidyl ether, still further more preferably 2-ethylhexyl glycidyl ether.

<22> The method for producing a cationic group-containing cellulose ether according to any of the above <14> to <21>, wherein the amount of the reagent for introducing a group that contains a branched hydrocarbon group having from 8 to 18 carbon atoms is preferably at least 0.01 mols relative to 1 mol of AGU in the starting cellulose, more preferably at least 0.03 mols, and is preferably at most 5 mols, more preferably at most 3 mols, even more preferably at most 1 mol, still more preferably at most 0.5 mols, further more preferably at most 0.2 mols.

<23> A surfactant composition containing the cationic group-containing cellulose ether of any of the above <1> to <13>, a surfactant and water.

<24> The surfactant composition according to the above <23>, wherein the content of the cationic group-containing cellulose ether is preferably at least 0.01% by mass, more preferably at least 0.05% by mass, and is preferably at most 10% by mass, more preferably at most 5% by mass, even more preferably at most 1% by mass.

<25> The surfactant composition according to the above <23> or <24>, wherein the cationic group-containing cellulose ether is preferably a cationic group-containing cellulose ether having MS(N+) of from 0.03 to 0.9, MS(Gly) of from 0.5 to 3.0 and MS(HC) of from 0.001 to 0.1, more preferably a cationic group-containing cellulose ether having MS(N+) of from 0.05 to 0.7, MS(Gly) of from 0.5 to 2.5 and MS(HC) of from 0.001 to 0.06.

<26> The surfactant composition according to any of the above <23> to <25>, wherein the surfactant is preferably alone or in a combination of two or more kinds selected from anionic surfactants, nonionic surfactants, cationic surfactants and ampholytic surfactants.

<27> The surfactant composition according to the above <26>, wherein the anionic surfactant is preferably at least one selected from alkylsulfate salts, polyoxyalkylene alkyl ether sulfate salts, higher fatty acid salts having from 8 to 16 carbon atoms, alkyl ether acetate salts represented by the following general formula (I), alkyl sulfosuccinate salts, acylglutamate salts, acylisethionates, acylmethyltaurates and internal olefinsulfonate salts having from 12 to 24 carbon atoms, more preferably at least one selected from polyoxyethylene alkyl ether sulfate salts, alkylsulfate salts and internal olefin sulfonate salts having from 12 to 24 carbon atoms.

$$R-O-(CH_2CH_2O)_a-CH_2-COOM \quad (I)$$

(In the formula, R represents an alkyl group having from 4 to 22 carbon atoms, a indicates a number of from 4 to 16, M represents a hydrogen atom, an alkali metal, an alkaline earth metal (1/2 atom), an ammonium or an organic ammonium.)

<28> The surfactant composition according to the above <26>, wherein the nonionic surfactant is preferably at least one selected from polyethylene glycol-type nonionic surfactants, polyalcohol-type nonionic surfactants and fatty acid alkanolamides, more preferably at least one selected from polyoxyalkylene alkyl ethers, polyoxyethylene hardened castor oil, fatty acid alkanolamides, and alkyl glycosides, even more preferably at least one selected from polyoxyalkylene alkyl ethers and fatty acid alkanolamides, still more preferably at least one selected from polyoxyethylene alkyl ethers and fatty acid monoalkanolamides.

<29> The surfactant composition according to the above <26>, wherein the ampholytic surfactant is preferably at least one selected from betaine-type surfactants and amine oxide-type surfactants, more preferably at least one selected from imidazoline-type betaines, alkyldimethylamine acetate betaines, fatty acid amide propylbetaines, and alkylhydroxysulfobetaines, even more preferably at least one selected from coconut oil fatty acid amide propylbetaine, Laurylcarboxymethylhydroxyimidazolium betaine, lauryldimethylaminoacetate betaine and laurylhydroxysulfobetaine.

<30> The surfactant composition according to the above <26>, wherein the cationic surfactant is preferably at least one selected from quaternary ammonium salts having a hydrocarbon group having from 12 to 28 carbon atoms and optionally interrupted by an amide group, an ester group or an ether group, pyridinium salts, and tertiary amine salts with mineral acids or organic acids, more preferably at least one selected from mono-long chain alkyltrimethylammonium salts, di-long chain alkyldimethylammonium salts, mono-long chain alkyldimethylamine salts, even more preferably a mono-long chain alkyltrimethylammonium salt.

<31> The surfactant composition according to any of the above <23> to <30>, wherein the content of the surfactant is preferably at least 0.01% by mass, more preferably at least 0.1% by mass, and is preferably at most 80% by mass, more preferably at most 50% by mass, even more preferably at most 36% by mass.

<32> The surfactant composition according to any of the above <23> to <31>, wherein the ratio by mass of the cationic group-containing cellulose ether to the surfactant is preferably at least 0.0002, more preferably at least 0.005, and is preferably at most 10, more preferably at most 5, even more preferably at most 3.

<33> The surfactant composition according to any of the above <23> to <32>, wherein the water content is preferably at least 10% by mass, more preferably at least 40% by mass, and is preferably at most 99.5% by mass.

<34> The surfactant composition according to any of the above <23> to <33>, which further contains any other cationic polymer than the cationic group-containing cellulose ether.

<35> The surfactant composition according to the above <34>, wherein the other cationic polymer than the cationic group-containing cellulose ether is preferably at least one selected from cationic galactomannan, cationized hydroxyalkyl cellulose, cationized starch, and cationic synthetic polymer produced through radical polymerization, more preferably at least one selected from cationic galactomannan, cationized hydroxyalkyl cellulose, and cationic synthetic polymer produced through radical polymerization, even more preferably at least one selected from cationized guar gum, cationized cassia gum, cationized locust bean gum, cationized hydroxyethyl cellulose, cationized hydroxypropyl cellulose and diallyl quaternary ammonium salt-acrylamide copolymer.

<36> The surfactant composition according to the above <34> or <35>, wherein the content of the other cationic polymer than the cationic group-containing cellulose ether is preferably at least 0.01% by mass, more preferably at least 0.02% by mass, even more preferably at least 0.05% by mass, and is preferably at most 5% by mass, more preferably at most 2% by mass, even more preferably at most 0.5% by mass.

<37> The surfactant composition according to any of the above <33> to <36>, wherein the ratio by mass of the cationic group-containing cellulose ether to the other cationic polymer than the cationic group-containing cellulose ether [cationic group-containing cellulose ether/cationic polymer except cationic group-containing cellulose ether] is preferably at least 0.05, more preferably at least 0.1, even more preferably at least 0.5, still more preferably at least 1, and is preferably at most 20, more preferably at most 10, even more preferably at most 8, still more preferably at most 5.

<38> The surfactant composition according to any of the above <23> to <37>, which further contains an oily agent.

<39> The surfactant composition according to the above <38>, wherein the amount of dissolution of the oily agent in 100 g of water at 20° C. is at least 0 g and at most 1 g, but preferably at most 0.5 g, more preferably at most 0.1 g.

<40> The surfactant composition according to the above <38> or <39>, wherein the oily agent is preferably at least one selected from (i) ester oils, (ii) silicone oils, (iii) ether oils, (iv) hydrocarbon oils, (v) higher alcohols and (vi) carboxylic acids having a hydrocarbon group having from 17 to 23 carbon atoms and optionally substituted with a hydroxyl group, more preferably an ester oil represented by the general formula (17), dimethylpolysiloxane, a polyoxyalkylene alkyl ether represented by the general formula (22), a higher alcohol having from 12 to 18 carbon atoms, or a saturated or unsaturated hydrocarbon having at most 20 carbon atoms.

<41> The surfactant composition according to any of the above <38> to <40>, wherein the content of the oily agent is preferably at least 0.01% by mass, more preferably at least 0.05% by mass, even more preferably at least 0.1% by mass, and is preferably at most 30% by mass, more preferably at most 20% by mass, even more preferably at most 15% by mass.

<42> The surfactant composition according to any of the above <38> to <41>, wherein the ratio by mass of the cationic group-containing cellulose ether to the oily agent [cationic group-containing cellulose ether/oily agent] is preferably at least 0.001, more preferably at least 0.005, even more preferably at least 0.01, and is preferably at most 5, more preferably at most 1, even more preferably at most 0.6.

<43> The surfactant composition according to any of the above <23> to <42>, which is used as a hair wash composition, a skin cleanser composition, a hair conditioner composition or a hair treatment composition.

<44> A hair wash composition containing the cationic group-containing cellulose ether of any of the above <1> to <13>, a surfactant and water.

<45> The hair wash composition according to the above <44>, wherein the cationic group-containing cellulose ether is preferably a cationic group-containing cellulose ether having MS(N+) of from 0.05 to 0.30, MS(Gly) of from 0.6 to 2.4 and MS(HC) of from 0.001 to 0.06, more preferably a cationic group-containing cellulose ether having MS(N+) of from 0.16 to 0.28, MS(Gly) of from 1.8 to 2.3 and MS(HC) of from 0.002 to 0.05, even more preferably a cationic group-containing cellulose ether having MS(N+) of from 0.20 to 0.25, MS(Gly) of from 2.0 to 2.2 and MS(HC) of from 0.01 to 0.03.

<46> The hair wash composition according to the above <44> or <45>, wherein the content of the cationic group-containing cellulose ether is preferably at least 0.01% by mass, more preferably at least 0.05% by mass, and is preferably at most 10% by mass, more preferably at most 5% by mass, even more preferably at most 1% by mass.

<47> The hair wash composition according to any of the above <44> to <46>, wherein the surfactant is preferably at least one selected from anionic surfactants, nonionic surfactants and ampholytic surfactants, more preferably at least one selected from polyoxyethylene alkyl ether sulfate salts, aliphatic monoalkanolamides, fatty acid amide propylbetaines and alkyldimethylamine acetate betaines.

<48> The hair wash composition according to any of the above <44> to <47>, wherein the content of the surfactant is preferably at least 0.01% by mass, more preferably at least 0.1% by mass, even more preferably at least 5% by mass, still more preferably at least 10% by mass, and is preferably at most 80% by mass, more preferably at most 50% by mass, even more preferably at most 36% by mass, still more preferably at most 30% by mass, further more preferably at most 25% by mass.

<49> The hair wash composition according to any of the above <44> to <48>, wherein the ratio by mass of the cationic group-containing cellulose ether to the surfactant [cationic group-containing cellulose ether/surfactant] is preferably at least 0.0002, more preferably at least 0.005, even more preferably at least 0.01, and is preferably at most 10, more preferably at most 5, even more preferably at most 3, still more preferably at most 0.3, further more preferably at most 0.05.

<50> The hair wash composition according to any of the above <44> to <49>, wherein the water content is preferably at least 10% by mass, more preferably at least 40% by mass, even more preferably at least 60% by mass, still more preferably at least 70% by mass, and is preferably at most 99.5% by mass, more preferably at most 95% by mass, even more preferably at most 90% by mass.

<51> The hair wash composition according to any of the above <44> to <50>, which further contains any other cationic polymer than the cationic group-containing cellulose ether.

<52> The hair wash composition according to the above <51>, wherein the other cationic polymer than the cationic group-containing cellulose ether is preferably at least one selected from cationic galactomannan, cationized hydroxyalkyl cellulose, cationized starch, and cationic synthetic polymer produced through radical polymerization, more preferably at least one selected from cationic galactomannan, cationized hydroxyalkyl cellulose, and cationic synthetic polymer produced through radical polymerization, even more preferably at least one selected from cationized guar gum, cationized cassia gum, cationized locust bean gum, cationized hydroxyethyl cellulose, cationized hydroxypropyl cellulose and diallyl quaternary ammonium salt-acrylamide copolymer.

<53> The hair wash composition according to the above <51> or <52>, wherein the cationic group-containing cellulose ether is preferably a cationic group-containing cellulose ether having MS(N+) of from 0.05 to 0.7, MS(Gly) of from 1.6 to 2.4 and MS(HC) of from 0.005 to 0.05, more preferably a cationic group-containing cellulose ether having MS(N+) of from 0.05 to 0.28, MS(Gly) of from 1.8 to 2.3 and MS(HC) of from 0.005 to 0.03, even more preferably a cationic group-containing cellulose ether having MS(N+) of from 0.20 to 0.25, MS(Gly) of from 2.0 to 2.2 and MS(HC) of from 0.01 to 0.03.

<54> The hair wash composition according to any of the above <44> to <53>, which further contains an oily agent.

<55> The hair wash composition according to the above <54>, wherein the amount of dissolution of the oily agent in 100 g of water at 20° C. is at least 0 g and at most 1 g, but preferably at most 0.5 g, more preferably at most 0.1 g.

<56> The hair wash composition according to the above <54> or <55>, wherein the oily agent is preferably at least one selected from (i) ester oils, (ii) silicone oils, (iii) ether oils, (iv) hydrocarbon oils, (v) higher alcohols and (vi) carboxylic acids having a hydrocarbon group having from 17 to 23 carbon atoms and optionally substituted with a hydroxyl group, more preferably at least one selected from silicone oils and ether oils, even more preferably at least one selected from dimethylpolysiloxane, amino-modified dimethylpolysiloxane, and polyoxyalkylene alkyl ethers represented by the above-mentioned general formula (22).

<57> The hair wash composition according to any of the above <54> to <56>, wherein the content of the oily agent is preferably at least 0.01% by mass, more preferably at least 0.05% by mass, even more preferably at least 0.1% by mass, still more preferably at least 0.5% by mass, further more preferably at least 1% by mass, and is preferably at most 30% by mass, more preferably at most 20% by mass, even more preferably at most 15% by mass, still more preferably at most 10% by mass, further more preferably at most 5% by mass.

<58> The hair wash composition according to any of the above <54> to <57>, wherein the ratio by mass of the cationic group-containing cellulose ether to the oily agent [cationic group-containing cellulose ether/oily agent] is preferably at least 0.001, more preferably at least 0.005, even more preferably at least 0.01, and is preferably at most 5, more preferably at most 1, even more preferably at most 0.6.

<59> The hair wash composition according to any of the above <54> to <58>, wherein the cationic group-containing cellulose ether is preferably a cationic group-containing cellulose ether having MS(N+) of from 0.05 to 0.7, MS(Gly) of from 1.8 to 2.4 and MS(HC) of from 0.001 to 0.06, more preferably a cationic group-containing cellulose ether having MS(N+) of from 0.11 to 0.35, MS(Gly) of from 1.8 to 2.2 and MS(HC) of from 0.002 to 0.05, even more preferably a cationic group-containing cellulose ether having MS(N+) of from 0.18 to 0.32, MS(Gly) of from 2.0 to 2.2 and MS(HC) of from 0.005 to 0.04.

<60> A skin cleanser composition containing the cationic group-containing cellulose ether of any of the above <1> to <13>, a surfactant and water.

<61> The skin cleanser composition according to the above <60>, wherein the cationic group-containing cellulose ether is preferably a cationic group-containing cellulose ether having MS(N+) of from 0.05 to 0.30, MS(Gly) of from 0.5 to 2.4 and MS(HC) of from 0.002 to 0.03, more preferably a cationic group-containing cellulose ether having MS(N+) of from 0.05 to 0.25, MS(Gly) of from 0.5 to 2.2 and MS(HC) of from 0.002 to 0.02.

<62> The skin cleanser composition according to the above <60> or <61>, wherein the content of the cationic group-containing cellulose ether is preferably at least 0.01% by mass, more preferably at least 0.05% by mass, and is preferably at most 10% by mass, more preferably at most 5% by mass, even more preferably at most 1% by mass.

<63> The skin cleanser composition according to any of the above <60> to <62>, wherein the surfactant is preferably at least one selected from anionic surfactants, nonionic surfactants and ampholytic surfactants, more preferably at least one selected from polyoxyethylene alkyl ether sulfate salts, alkyl sulfate salts, higher fatty acids having from 8 to 16 carbon atoms or their salts, acylisethionates, hydrophobic site-having sulfonate salts, hydrophobic site-having amino acid salts, fatty acid monoalkanolamides, fatty acid amide propylbetaines and imidazoline-type betaines.

<64> The skin cleanser composition according to any of the above <60> to <63>, wherein the content of the surfactant is preferably at least 0.01% by mass, more preferably at least 0.1% by mass, even more preferably at least 5% by mass, still more preferably at least 10% by mass, and is preferably at most 80% by mass, more preferably at most 50% by mass, even more preferably at most 36% by mass.

<65> The skin cleanser composition according to any of the above <60> to <64>, wherein the ratio by mass of the cationic group-containing cellulose ether to the surfactant [cationic group-containing cellulose ether/surfactant] is preferably at least 0.0002, more preferably at least 0.005, and is preferably at most 10, more preferably at most 5, even more preferably at most 3, still more preferably at most 0.3, further more preferably at most 0.05.

<66> The skin cleanser composition according to any of the above <60> to <65>, wherein the water content is preferably at least 10% by mass, more preferably at least 40% by mass, and is preferably at most 99.5% by mass, more preferably at most 95% by mass, even more preferably at most 90% by mass.

<67> The skin cleanser composition according to any of the above <60> to <66>, which further contains any other cationic polymer than the cationic group-containing cellulose ether, and contains at least one selected from cationized guar bum and cationized hydroxyethyl cellulose.

<68> The skin cleanser composition according to any of the above <60> to <67>, which further contains an oily agent.

<69> The skin cleanser composition according to the above <68>, wherein the amount of dissolution of the oily agent in 100 g of water at 20° C. is at least 0 g and at most 1 g, but preferably at most 0.5 g, more preferably at most 0.1 g.

<70> The skin cleanser composition according to the above <68> or <69>, wherein the oily agent is preferably at least one selected from (i) ester oils, (ii) silicone oils, (iii) ether oils, (iv) hydrocarbon oils, (v) higher alcohols and (vi) carboxylic acids having a hydrocarbon group having from 17 to 23 carbon atoms and optionally substituted with a hydroxyl group, more preferably at least one selected from ester oils, hydrocarbon oils and carboxylic acids having a hydrocarbon group having from 17 to 23 carbon atoms and optionally substituted with a hydroxyl group, even more preferably at least one selected from sunflower oil and vaseline.

<71> The skin cleanser composition according to any of the above <68> to <70>, wherein the content of the oily agent is preferably at least 0.01% by mass, more preferably at least 0.05% by mass, even more preferably at least 0.1% by mass, still more preferably at least 0.5% by mass, further more preferably at least 2% by mass, even further more preferably at least 4% by mass, and is preferably at most 30% by mass, more preferably at most 20% by mass, even more preferably at most 15% by mass.

<72> The skin cleanser composition according to any of the above <68> to <71>, wherein the ratio by mass of the cationic group-containing cellulose ether to the oily agent [cationic group-containing cellulose ether/oily agent] is preferably at least 0.001, more preferably at least 0.005, even more preferably at least 0.01, and is preferably at most 5, more preferably at most 1, even more preferably at most 0.6, still more preferably at most 0.3, further more preferably at most 0.1.

<73> The skin cleanser composition according to any of the above <60> to <72>, which is at least one selected from body shampoo, hand wash, face wash and makeup remover, preferably at least one selected from body shampoo, hand wash and face wash.

<74> A hair conditioner composition containing the cationic group-containing cellulose ether of any of the above <1> to <13>, a surfactant, an oily agent and water.

<75> The hair conditioner composition according to the above <74>, wherein the cationic group-containing cellulose ether is preferably a cationic group-containing cellulose ether having MS(N+) of from 0.05 to 0.5, MS(Gly) of from 0.5 to 2.5 and MS(HC) of from 0.005 to 0.05, more preferably a cationic group-containing cellulose ether having MS(N+) of from 0.05 to 0.28, MS(Gly) of from 1.8 to 2.4 and MS(HC) of from 0.01 to 0.03, even more preferably a cationic group-containing cellulose ether having MS(N+) of from 0.20 to 0.25, MS(Gly) of from 2.0 to 2.2 and MS(HC) of from 0.01 to 0.03.

<76> The hair conditioner composition according to the above <74> or <75>, wherein the content of the cationic group-containing cellulose ether is preferably at least 0.01% by mass, more preferably at least 0.05% by mass, and is preferably at most 10% by mass, more preferably at most 5% by mass, even more preferably at most 1% by mass.

<77> The hair conditioner composition according to any of the above <74> to <76>, wherein the surfactant is preferably a cationic surfactant, more preferably at least one selected from quaternary ammonium salts having a hydrocarbon group having from 12 to 28 carbon atoms and optionally interrupted by an amide group, an ester group or an ether group, pyridinium salts, and tertiary amine salts with mineral acids or organic acids, even more preferably at least one selected from mono-long chain alkyltrimethylammonium salts, di-long chain alkyldimethylammonium salts, mono-long chain alkyldimethylamine salts, further more preferably mono-long chain alkyltrimethylammonium salts, still further more preferably at least one selected from behenyltrimethylammonium salts and cetyltrimethylammonium salts.

<78> The hair conditioner composition according to any of the above <74> to <77>, wherein the content of the surfactant is preferably at least 0.01% by mass, more preferably at least 0.1% by mass, and is preferably at most 80% by mass, more preferably at most 50% by mass, even more preferably at most 36% by mass, still more preferably at most 20% by mass, further more preferably at most 10.% by mass.

<79> The hair conditioner composition according to any of the above <74> to <78>, wherein the ratio by mass of the cationic group-containing cellulose ether to the surfactant is preferably at least 0.0002, more preferably at least 0.005, even more preferably at least 0.05, and is preferably at most 10, more preferably at most 5, even more preferably at most 3, still more preferably at most 1, further more preferably at most 0.5.

<80> The hair conditioner composition according to any of the above <74> to <79>, wherein the water content is preferably at least 10% by mass, more preferably at least 40% by mass, even more preferably at least 70% by mass, further more preferably at least 80% by mass, and is preferably at most 99.5% by mass.

<81> The hair conditioner composition according to any of the above <74> to <80>, wherein the amount of dissolution of the oily agent in 100 g of water at 20° C. is at least 0 g and at most 1 g, but preferably at most 0.5 g, more preferably at most 0.1 g.

<82> The hair conditioner composition according to any of the above <74> to <81>, wherein the oily agent is preferably at least one selected from (i) ester oils, (ii) silicone oils, (iii) ether oils, (iv) hydrocarbon oils, (v) higher alcohols and (vi) carboxylic acids having a hydrocarbon group having from 17 to 23 carbon atoms and optionally substituted with a hydroxyl group, more preferably at least one selected from silicone oils and higher alcohols, even more preferably at least one selected from dimethylpolysiloxane, cetyl alcohol and stearyl alcohol.

<83> The hair conditioner composition according to any of the above <74> to <82>, wherein the content of the oily agent is preferably at least 0.01% by mass, more preferably at least 0.05% by mass, even more preferably at least 0.1% by mass, and is preferably at most 30% by mass, more preferably at most 20% by mass, even more preferably at most 15% by mass, still more preferably at most 10% by mass, further more preferably at most 8% by mass.

<84> The hair conditioner composition according to any of the above <74> to <83>, wherein the ratio by mass of the cationic group-containing cellulose ether to the oily agent [cationic group-containing cellulose ether/oily agent] is preferably at least 0.001, more preferably at least 0.005, even more preferably at least 0.01, and is preferably at most 5, more preferably at most 1, even more preferably at most 0.6.

<85> The hair conditioner composition according to any of the above <74> to <84>, of which the pH is preferably at least 1, more preferably at least 2, even more preferably at least 3, and is preferably at most 10, more preferably at most 8, even more preferably at most 6.

<86> The hair conditioner composition according to any of the above <74> to <85>, which is hair rinse, treatment, hair conditioner, leave-in hair conditioner, hair cream, conditioner gel, or conditioner foam.

<87> A hair treatment composition containing the cationic group-containing cellulose ether of any of the above <1> to <13>, and containing at least one treatment agent selected from a hair-coloring dye, an oxidizing agent, an alkali agent and a keratin-reducing agent.

<88> The hair treatment composition according to the above <87>, wherein the cationic group-containing cellulose ether is preferably a cationic group-containing cellulose ether having MS(N+) of from 0.05 to 0.32, MS(Gly) of from 0.6 to 2.3 and MS(HC) of from 0.001 to 0.05, more preferably a cationic group-containing cellulose ether having MS(N+) of from 0.11 to 0.32, MS(Gly) of from 0.7 to 2.0 and MS(HC) of from 0.002 to 0.03.

<89> The hair treatment composition according to the above <87> or <88>, wherein the content of the cationic group-containing cellulose ether is preferably at least 0.01% by mass, more preferably at least 0.05% by mass, and is preferably at most 10% by mass, more preferably at most 2% by mass, even more preferably at most 1% by mass.

<90> The hair treatment composition according to any of the above <87> to <89>, which is a multi-pack composition to be used by mixing two packs or more and in which the cationic group-containing cellulose ether is incorporated in the first pack.

<91> The hair treatment composition according to any of the above <87> to <90>, wherein the ratio by mass of the cationic group-containing cellulose ether to the treatment agent (cationic group-containing cellulose ether/treatment agent] is preferably at least 0.0002, more preferably at least 0.002, and is preferably at most 5, more preferably at most 3, even more preferably at most 1, still more preferably at most 0.1.

<92> The hair treatment composition according to any of the above <87> to <91>, wherein the hair-coloring dye is at least one selected from direct dyes and oxidation dye intermediates.

<93> The hair treatment composition according to the above <92>, wherein the direct dye is at least one selected from nitro dyes, anthraquinone dyes, acidic dyes, oil-soluble dyes and basic dyes.

<94> The hair treatment composition according to the above <92> or <93>, wherein the content of the direct dye is at least 0.005% by mass, more preferably at least 0.01% by mass, and is preferably at most 10% by mass, more preferably at most 5% by mass.

<95> The hair treatment composition according to any of the above <92> to <94>, wherein the oxidation dye intermediate is at least one selected from precursors and couplers.

<96> The hair treatment composition according to any of the above <92> to <95>, wherein the content of the oxidation dye intermediate is preferably at least 0.01% by mass, more preferably at least 0.1% by mass, and is preferably at most 10% by mass, more preferably at most 5% by mass.

<97> The hair treatment composition according to any of the above <87> to <96>, wherein the oxidizing agent is preferably at least one selected from hydrogen peroxide, urea peroxide, melamine peroxide, sodium perborate, potassium perborate, percarbonates and bromates.

<98> The hair treatment composition according to any of the above <87> to <97>, wherein the content of the oxidizing agent is preferably at least 0.1% by mass, more preferably at least 0.5% by mass, and is preferably at most 20% by mass, more preferably at most 12% by mass.

<99> The hair treatment composition according to any of the above <87> to <98>, wherein the alkali agent is preferably at least one selected from sodium hydroxide, ammonia and its salts, alkanolamine and its salts, alkanediamine and its salt, as well as carbonates, more preferably selected from ammonia and its salts, alkanolamine and its salts, and sodium hydrogencarbonate.

<100> The hair treatment composition according to any of the above <87> to <99>, wherein the content of the alkali agent is preferably at least 0.1% by mass and is at most 10% by mass.

<101> The hair treatment composition according to any of the above <87> to <100>, wherein the keratin-reducing agent is preferably at least one selected from thioglycolic acid and its derivatives, thiolactic acid and its derivatives, cysteine and its derivatives, and their salts, thioglyceryl alkyl ethers represented by the above-mentioned formula (23) and their salts, and mercaptoalkylamides represented by the above-mentioned formula (24) and their salts, and is more preferably at least one selected from thioglycolic acid, ammonium thioglycolate, glycerin thioglycolate, L-cysteine, D-cysteine, N-acetylcysteine, ammonium salts and ethanolamine salts of those cysteines, thioglyceryl alkyl ethers, mercaptoethylpropanamide, and mercaptoethylgluconamide.

<102> The hair treatment composition according to any of the above <87> to <101>, wherein the content of the keratin-reducing agent is preferably at least 0.1% by mass, more preferably at least 1% by mass, and is preferably at most 20% by mass, more preferably at most 15% by mass, even more preferably at most 10% by mass.

<103> The hair treatment composition according to any of the above <87> to <102>, which further contains water and in which the content of water is preferably at least 10% by mass and at most 99.5% by mass.

<104> The hair treatment composition according to any of the above <87> to <103>, which further contains a surfactant and in which the content of the surfactant is preferably at least 0.01% by mass, more preferably at least 0.1% by mass, even more preferably at least 1% by mass, and is preferably at most 80% by mass, more preferably at most 50% by mass, even more preferably at most 36% by mass, still more preferably at most 20% by mass, further more preferably at most 10% by mass, still further more preferably at most 5% by mass.

<105> The hair treatment composition according to any of the above <87> to <104>, which further contains an oily agent.

<106> The hair treatment composition according to the above <105>, wherein the oily agent is preferably at least one selected from (i) ester oils, (ii) silicone oils, (iii) ether oils, (iv) hydrocarbon oils, (v) higher alcohols and (vi) carboxylic acids having a hydrocarbon group having from 17 to 23 carbon atoms and optionally substituted with a hydroxyl group.

<107> The hair treatment composition according to the above <105> or <106>, wherein the content of the oily agent is preferably at least 0.01% by mass, more preferably at least 0.05% by mass, even more preferably at least 0.1% by mass, and is preferably at most 30% by mass, more preferably at most 20% by mass, even more preferably at most 15% by mass.

<108> The hair treatment composition according to any of the above <105> to <107>, wherein the ratio by mass of the cationic group-containing cellulose ether to the oily agent [cationic group-containing cellulose ether/oily agent] is preferably at least 0.001, more preferably at least 0.005, even more preferably at least 0.01, and is preferably at most 5, more preferably at most 1, even more preferably at most 0.6.

<109> The hair treatment composition according to any of the above <87> to <108>, which is at least one selected from a hair color composition and a perm composition.

<110> The hair treatment composition according to the above <109>, which is a hair color composition, preferably at least one selected from a color composition and a hair bleach composition.

<111> The hair treatment composition according to the above <110>, wherein the hair color composition contains the cationic group-containing cellulose ether, and at least one treatment agent selected from a hair-coloring dye, an oxidizing agent and an alkali agent.

<112> The hair treatment composition according to the above <110> or <111>, wherein the hair color composition is preferably at least one selected from one-pack hair color compositions (a) and (b) mentioned below, and multi-pack hair color composition of (c) and (d) mentioned below.

(a) One-pack hair color composition containing a hair-coloring dye and optionally an oxidizing agent.

(b) One-pack hair color composition not containing a hair-coloring dye but containing an oxidizing agent.

(c) Two-pack hair color composition composed of a first pack containing an alkali agent and/or a hair-coloring dye, and a second pack containing an oxidizing agent.

(d) Three-pack hair color composition composed of a first pack containing an alkali agent and/or a hair-coloring dye, a second pack containing an oxidizing agent, and a third pack containing an oxidation promoter.

<113> The hair treatment composition according to the above <112>, wherein the content ratio (by mass) of the first pack to the second pack [first pack/second pack] in the above two-pack hair color composition (c) is preferably from 2/8 to 6/4, more preferably from 3/7 to 5/5, even more preferably from 3.5/6.5 to 4.5/5.5.

<114> The hair treatment composition according to any of the above <110> to <113>, wherein the content of the cationic group-containing cellulose ether in the hair color composition is preferably at least 0.01% by mass, more preferably at least 0.05% by mass, and is preferably at most 10% by mass, more preferably at most 2% by mass, even more preferably at most 1% by mass.

<115> The hair treatment composition according to any of the above <111> to <114>, wherein the hair-coloring dye in the hair color composition is preferably at least one selected from a direct dye and an oxidation dye intermediate.

<116> The hair treatment composition according to any of the above <111> to <115>, wherein the oxidizing agent in the hair color composition is preferably at least one selected from hydrogen peroxide, urea peroxide, melamine peroxide, sodium perborate, potassium perborate, percarbonates and bromates, more preferably at least one selected from hydrogen peroxide, urea peroxide, melamine peroxide, sodium perborate, potassium perborate, sodium percarbonate and potassium percarbonate, even more preferably hydrogen peroxide.

<117> The hair treatment composition according to any of the above <111> to <116>, wherein the content of the oxidizing agent in the hair color composition is preferably at least 0.1% by mass, more preferably at least 0.5% by mass, even more preferably at least 2% by mass, and is preferably at most 20% by mass, more preferably at most 12% by mass, even more preferably at most 9% by mass.

<118> The hair treatment composition according to any of the above <111> to <117>, wherein the alkali agent in the hair color composition is preferably at least one selected from sodium hydroxide, ammonia and its salts, alkanolamine and its salts, alkanediamine and its salt, as well as carbonates, more preferably at least one selected from ammonia, alkanolamine and their salts, and sodium hydrogencarbonate, even more preferably at least one selected from ammonia, alkanolamine and their salts.

<119> The hair treatment composition according to any of the above <111> to <118>, wherein the content of the alkali agent in the hair color composition is preferably at least 0.1% by mass and is at most 10% by mass.

<120> The hair treatment composition according to any of the above <111> to <119>, wherein the hair color composition further contains water and the water content therein is preferably at least 10% by mass and at most 99.5% by mass.

<121> The hair treatment composition according to any of the above <111> to <120>, wherein the hair color composition further contains a surfactant.

<122> The hair treatment composition according to the above <121>, wherein the surfactant in the hair color composition is preferably at least one selected from anionic surfactants and nonionic surfactants, more preferably at least one selected from hydrophobic site-having sulfate ester salts and polyoxyethylene glycol-type nonionic surfactants, even more preferably at least one selected from polyoxyethylene alkyl ether sulfate salts and polyoxyethylene alkyl ethers.

<123> The hair treatment composition according to the above <121> or <122>, wherein the content of the surfactant in the hair color composition is preferably at least 0.01% by mass, more preferably at least 0.1% by mass, even more preferably at least 1% by mass, and is preferably at most 80% by mass, more preferably at most 50% by mass, even more preferably at most 36% by mass, still more preferably at most 30% by mass, further more preferably at most 20% by mass, still further more preferably at most 10% by mass.

<124> The hair treatment composition according to any of the above <111> to <123>, wherein the hair color composition further contains an oily agent.

<125> The hair treatment composition according to the above <124>, wherein the oily agent is preferably at least one selected from (i) ester oils, (ii) silicone oils, (iii) ether oils, (iv) hydrocarbon oils, (v) higher alcohols and (vi) carboxylic acids having a hydrocarbon group having from 17 to 23 carbon atoms and optionally substituted with a hydroxyl group, more preferably a higher alcohol, even more preferably at least one selected from lauryl alcohol, myristyl alcohol, cetyl alcohol, stearyl alcohol, behenyl alcohol and 2-octyldodecanol.

<126> The hair treatment composition according to the above <124> or <125>, wherein the content of the oily agent in the hair color composition is preferably at least 0.01% by mass, more preferably at least 0.05% by mass, even more preferably at least 0.1% by mass, still more preferably at least 0.5% by mass, further more preferably at least 1% by mass, and is preferably at most 30% by mass, more preferably at most 20% by mass, even more preferably at most 15% by mass, further more preferably at most 10% by mass, still more preferably at most 5% by mass.

<127> The hair treatment composition according to the above <109>, which is a perm composition, and is preferably at least one selected from a permanent wave composition, straight perm composition, a sustainable hair-styling composition and a hair relaxer composition.

<128> The hair treatment composition according to the above <127>, wherein the perm composition contains the cationic group-containing cellulose ether and, as treatment agents, a keratin-reducing agent, an oxidizing agent and an alkali agent.

<129> The hair treatment composition according to the above <127> or <128>, wherein the perm composition is a two-pack composition composed of a first pack that contains a keratin-reducing agent and a second pack that contains an oxidizing agent, and the usage ratio (by mass) of the first pack to the second pack [first pack/second pack] is preferably from 3/7 to 7/3, more preferably from 4/6 to 6/4, even more preferably from 4.5/5.5 to 5.5/4.5.

<130> The hair treatment composition according to the above <128> or <129>, wherein the content of the cationic group-containing cellulose ether in the perm composition is preferably at least 0.01% by mass, more preferably at least 0.05% by mass, and is preferably at most 10% by mass, more preferably at most 2% by mass, even more preferably at most 1% by mass.

<131> The hair treatment composition according to any of the above <128> to <130>, wherein the keratin-reducing agent in the perm composition is preferably at least one selected from thioglycolic acid and its derivatives, thiolactic acid and its derivatives, cysteine and its derivatives, as well as their salts, and thioglyceryl alkyl ethers of the above-mentioned formula (23) and their salts, and mercaptoalkylamides of the above-mentioned formula (24) and their salts, more preferably at least one selected from thioglycolic acid, ammonium thioglycolate, glycerin thioglycolate, L-cysteine, D-cysteine, N-acetylcysteine, ammonium salts and ethanolamine salts of those cysteines, thioglyceryl alkyl ethers, mercaptoethylpropanamide, and mercaptoethylgluconamide.

<132> The hair treatment composition according to any of the above <128> to <131>, wherein the content of the keratin-reducing agent in the perm composition is preferably at least 0.1% by mass, more preferably at least 1% by mass, and is preferably at most 20% by mass, more preferably at most 15% by mass, even more preferably at most 10% by mass.

<133> The hair treatment composition according to any of the above <128> to <132>, wherein the oxidizing agent in the perm composition is preferably at least one selected from hydrogen peroxide, urea peroxide, melamine peroxide, sodium perborate, potassium perborate, percarbonates and bromates, more preferably at least one selected from potassium bromate, sodium bromate, sodium percarbonate and hydrogen peroxide, even more preferably at least one selected from potassium bromate, sodium bromate and hydrogen peroxide.

<134> The hair treatment composition according to any of the above <128> to <133>, wherein the content of the oxidizing agent in the perm composition is preferably at least 0.1% by mass, more preferably at least 0.5% by mass, even more preferably at least 1% by mass, still more preferably at least 2% by mass, and is preferably at most 20% by mass, more preferably at most 12% by mass, even more preferably at most 10% by mass, still more preferably at most 9% by mass, further more preferably at most 5% by mass.

<135> The hair treatment composition according to any of the above <128> to <134>, wherein the alkali agent in the perm composition is preferably at least one selected from sodium hydroxide, ammonia and its salts, alkanolamine and its salts, alkanediamine and its salt, as well as carbonates, more preferably at least one selected from ammonia and its salts, alkanolamine and its salts, and sodium hydrogencarbonate.

<136> The hair treatment composition according to any of the above <128> to <135>, wherein the content of the alkali agent in the perm composition is preferably at least 0.1% by mass and preferably at most 10% by mass, more preferably at most 5% by mass.

<137> A hair washing, including washing hair with the hair wash composition of any of the above <44> to <59>, then rinsing and drying the hair.

<138> A skin cleaning method, including washing a skin with the skin cleanser composition of any of the above <60> to <73>, then rinsing and drying the skin.

<139> A hair conditioning method, including washing hair with a detergent, and then applying the hair conditioner composition of any of the above <74> to <86> to the hair.

<140> A hair treating method, including treating hair with the hair treatment composition of any of the above <87> to <136>, then rinsing and drying the hair.

<141> Use of a composition that contains the cationic group-containing cellulose ether of any of the above <1> to <13>, a surfactant and water as a hair wash.

<142> Use of as a hair wash according to the above <141>, wherein the composition further contains an oily agent.

<143> Use of as a hair wash according to the above <141> or <142>, wherein the composition further contains any other cationic polymer than the cationic group-containing cellulose ether.

<144> Use of a composition that contains the cationic group-containing cellulose ether of any of the above <1> to <13>, a surfactant and water as a skin cleanser.

<145> Use of a composition that contains the cationic group-containing cellulose ether of any of the above <1> to <13>, a surfactant, an oily agent and water as a hair conditioner.

<146> Use of a composition that contains the cationic group-containing cellulose ether of any of the above <1> to <13>, as well as at least one treatment agent selected from a hair-coloring dye, an oxidizing agent, an alkali agent and a keratin-reducing agent, as a hair treatment.

EXAMPLES

In the following Production Examples, Examples and Comparative Examples, "%" means "% by mass". Physical properties and others were measured according to the methods mentioned below.

(1) Measurement of Viscosity-Average Degree of Polymerization of Cellulose (Cuprammonium Process)

(i) Preparation of Solution for Measurement 0.5 g of cuprous chloride, and 20 to 30 mL of 25% aqueous ammonia were added to a measuring flask (100 mL) and completely dissolved therein, and then 1.0 g of cupric hydroxide and 25% aqueous ammonium were added thereto up to the gauge line of the flask, and then this was stirred for 3 hours until complete dissolution.

(ii) Sample Preparation 25 mg of the sample for measurement was added to a measuring flask (25 mL), and the solution prepared in the above was added thereto until the meniscus thereof could be the same as the gauge line of the flask. This was stirred for 6 hours until complete dissolution.

(iii) Measurement of Viscosity-Average Degree of Polymerization

The obtained aqueous cuprammonium solution was put into an Ubbelohde viscometer and statically left in a constant-temperature bath (20±0.1° C.) for 1 minute, and thereafter the liquid flow speed was measured. From the flow time (t (sec)) of the cuprammonium solution having a different sample concentration (g/L) and the flow time ($t_0$ (sec)) of the aqueous cuprammonium solution with no sample, the relative viscosity $\eta_r$ was calculated according to the following formula:

$$\eta_r = t/t_0$$

Next, the reduced viscosity ($\eta_{sp}/c$) at each concentration was calculated according to the following formula:

$$\eta_{sp}/c = (\eta_r - 1)/c$$

(c: sample concentration (g/dL))

Further, by extrapolating the reduced viscosity with c=0, the intrinsic viscosity [η] was calculated, and the viscosity-average degree of polymerization (n) was calculated according to the following formula:

$$n = 2000 \times [\eta]$$

In Examples, the mean degree of polymerization of CCE and the mean degree of polymerization of cationized hydroxypropyl cellulose (C-HPC) were considered to be the same as the mean degree of polymerization of the starting cellulose used in production (2) Calculation of Degree of Substitution with Substituent, MS in CCE The degree of substitution with a glycerol group (MS (Gly)), the degree of substitution with a cationized oxyalkylene group (MS(N+)) and the degree of substitution with a hydrocarbon group-containing group (MS(HC)) in CCE were calculated according to a system of equations of the following math formulae (1) to (3):

$$-a \times (\text{content of glycerol group (\%)}) \times MS(HC) + (74.1 - 74.1 \times (\text{content of glycerol group (\%)})) \times MS(Gly) - b \times (\text{content of glycerol group (\%)}) \times MS(N+) = 162.1 \times (\text{content of glycerol group (\%)}) \quad (1)$$

$$-a \times (\text{nitrogen content (\%)}) \times MS(HC) - 74.1 \times (\text{nitrogen content (\%)}) \times MS(Gly) + (b - b \times \text{nitrogen content (mass \%)}) \times MS(N+) = 162.1 \times (\text{nitrogen content (\%)}) \quad (2)$$

$$(a - a \times (\text{content of hydrocarbon group-containing group (\%)})) \times MS(HC) - 74.1 \times (\text{content of hydrocarbon group-containing group (\%)}) \times MS(Gly) - b \times (\text{content of hydrocarbon group-containing group (\%)}) \times MS(N+) = 162.1 \times (\text{content of hydrocarbon group-containing group (\%)}) \quad (3)$$

(In the formulae, a indicates the molecular weight of the hydrocarbon group-containing group, b indicates the molecular weight of the cationized oxyalkylene group.)

In the above-mentioned system of equations, the content of the glycerol group, the nitrogen content and the content of the hydrocarbon group-containing group each are in terms of % by mass of the glycerol group, the nitrogen that constitutes the cationized oxyalkylene group and the hydrocarbon group-containing group, and were calculated according to the methods mentioned below.

[Measurement of Content of Glycerol Group and Hydrocarbon Group-Containing Group (% by Mass)]

The content % (by mass) of the glycerol group contained in CCE was calculated according to the Zeisel method that is known as a method of determining the mean addition molar number of the alkoxy group in a cellulose ether as described in Analytical Chemistry Vol. 51, No. 13, 2172 (1979), "15th Revised Japanese Pharmacopoeia (section of analysis method for hydroxypropyl cellulose)", etc. The procedure is shown below.

(i) One ml of n-tetradecane was added to a 25-mL measuring flask, then o-xylene was added thereto until the lower face of the liquid meniscus thereof could reach the upper edge of the gauge line of the measuring flask, and stirred to prepare an internal standard solution.

(ii) 65 mg of purified and dried CCE, and 65 mg of adipic acid were accurately metered in a 10-mL vial container, and 2 mL of the internal standard solution prepared in (i) and 2 mL of hydroiodic acid solution were added thereto and sealed up.

(iii) While stirred with a stirrer chip, the mixture in the vial container was heated with a block heater at 150° C. for 1 hour.

(iv) The upper layer (o-xylene layer) of the mixture that had been separated in two phases in the vial container was analyzed through gas chromatography to thereby quantitatively determine the glycerol group-derived isopropyl iodide, and the hydrocarbon group-containing group-derived iodide of the hydrocarbon group (for example, in case where the hydrocarbon group-containing group is a 2-ethylhexyl group, 2-ethylhexyl iodide); and from the found data, the content of the glycerol group (% by mass) and the content of the hydrocarbon group-containing group (% by mass) were calculated.

The conditions for analysis were as follows:
Column: Agilent's HP-1 (length: 30 m, inner diameter: 0.32 mm, membrane thickness: 0.25 mm, fixed phase: 100% methyl-siloxane)
Column temperature: 40° C. (5 min)→10° C./min→230° C. (5 min)
Injector temperature: 210° C.
Detector: hydrogen flame ion detector (FID)
Detector temperature: 230° C.
Amount of implantation: 1 μL
Carrier gas flow rate: helium 3.0 mL/min

[Measurement of Nitrogen Content (% by Mass)](Kjeldahl Method)]

100 mg of purified and dried CCE was accurately metered, to which added were 10 mL of sulfuric acid and one tablet of a decomposition promoter "KJELTABS" (by Nakayama Rika Seisakusho); and using a Kjeldahl decomposition apparatus "K-432" (by "BUCHI"), this was completely dissolved by heating at 250° C. for 30 minutes, at 300° C. for 30 minutes and at 420° C. for 80 minutes in that order. After the decomposition reaction, 30 mL of ion-exchanged water was added to the sample; and using an automatic Kjeldahl distillation/titration apparatus "K-370" (by BUCHI), this was alkalized with 40 mL of aqueous 30% sodium hydroxide solution added thereto, and then ammonia that had been liberated through distillation was collected in an aqueous 1% boric acid solution, which was then titered with 0.01 N sulfuric acid (by Wako Pure Chemicals, for quantitative analysis) to thereby determine the nitrogen content (% by mass) in CCE.

(3) Calculation of Degree of Substitution, MS in C-HPC

The degree of substitution with a propyleneoxy group and the degree of substitution with a cationized oxymethylene group in C-HPC were calculated according to the methods mentioned below.

C-HPC obtained in Production Example was purified through a dialytic membrane (molecular weight cutoff: 1000), and then the aqueous solution was freeze-dried to give a purified C-HPC. The chlorine content (%) in the thus-obtained pure C-HPC was determined through elementary analysis. The number of the cationized oxymethylene groups in C-HPC was approximated to be the same as the number of the chloride ions that are the counter ions to the groups, and according to the following math formula (4), the amount of the cationized ethyleneoxy groups (a (mol/g)) in the unit mass of C-HPC was calculated.

$$a \text{ (mol/g)} = \text{(chlorine content (\%) obtained through elementary analysis)}/(35.5 \times 100) \quad (4)$$

According to the "Analysis Method for Hydroxypropyl Cellulose" described in Japanese Pharmacopoeia but except that the subject to be analyzed is pure C-HPC and not hydroxypropyl cellulose, the hydroxypropoxy group content (%) was determined. According to the following math formula (5), the hydroxypropoxy group content [formula weight $(OC_3H_6OH)=75.09$](b (mol/g)) was obtained.

$$b \text{ (mol/g)} = \text{(hydroxypropoxy group content (\%) obtained through gas chromatography)}/(75.09 \times 100) \quad (5)$$

From the thus-obtained a and b and according to the math formulae (6) and (7) mentioned below, the degree of substitution with cationized ethyleneoxy group (k) and the degree of substitution with propyleneoxy group (m) were calculated.

$$a = k/(162 + k \times K + m \times 58) \quad (6)$$

$$b = m/(162 + k \times K + m \times 58) \quad (7)$$

[In the formulae, k and K each indicate the degree of substitution with cationized ethyleneoxy group and the weight formula of the group; and m indicates the degree of substitution with propyleneoxy group.]

(4) Evaluation of Solubility in Water 0.5 g of a different polymer, such as purified and dried CCE or the like and 49.5 g of ion-exchanged water were put into a 50-mL columnar vial having a diameter of 32 mm, and stirred for 6 hours to give an aqueous 1% solution or 1% dispersion. The obtained aqueous 1% solution or 1% dispersion was visually evaluated for the solubility.
A: High solubility (transparent)
B: Low solubility (slightly cloudy)
C: Insoluble (gel)

(5) Measurement of Viscosity of Aqueous Solution 0.5 g of a different polymer, such as purified and dried CCE or the like and 49.5 g of ion-exchanged water were put into a 50-mL columnar vial having a diameter of 32 mm, and stirred for 6 hours to give an aqueous 1 mass % solution or 1 mass % dispersion of the polymer such as CCE.

Thus obtained, the aqueous 1 mass % solution or 1 mass % dispersion was conditioned at 25° C. in a thermostat bath, then using a B-type viscometer "TVB-10M" (by Toki Sangyo), the viscosity of the sample was measured at a temperature of 25° C. and at a rotation sped of 30 rpm with Rotor No. 1, 2, 3 or 4.

The rotor to be used was so selected that the measurement results could fall within a range of from 20 to 90% of the upper limit of the viscosity detection range with the rotor used.

(6) Measurement of Water Content

The water content of pulp, floc cellulose and powdery cellulose was measured at a measurement temperature of 120° C., using an electronic moisture meter "MOC-120H" (by Shimadzu). About 1 g of the sample to be analyzed was analyzed with the tester, and the point at which the weight change in 30 seconds could be at most 0.1% was read as the end point of the measurement.

(7) Determination of Double Bond Position in Starting Internal Olefin

The position of the double bond in the starting internal olefin was determined through gas chromatography (hereinafter referred to as "GC"). Concretely, the internal olefin was reacted with dimethyl disulfide to provide a dithioated derivative, and then separated into the constitutive components through GC. From each peak area, the position of the double bond in the internal olefin was determined.

The apparatus and the condition for analysis were as follows:
GC apparatus: "HP6890" (by Hewlett Packard)
Column: "Ultra-Alloy-1HT Capillary Column" 30 m×250 µm×0.15 µm (by Frontier Labo)
Detector: hydrogen flame ion detector (FID)
Injection temperature: 300° C.
Detector temperature: 350° C.
He flow rate: 4.6 mL/min (8) Measurement of Mass Ratio of Hydroxy Form/Olefin Form of Internal Olefinsulfonate Salt The ratio by mass of the hydroxy form/olefin form of internal olefinsulfonate salt was measured through HPLC-MS. Concretely, the internal olefinsulfonate salt to be analyzed was separated into the hydroxy form and the olefin form though HPLC, and each form was identified through MS. From the HPLC-MS peak area of each component, the proportion of each component was determined.

The apparatus and the condition for analysis were as follows:
HPLC apparatus: "Agilent Technology 1100" (by Agilent Technology)
Column: "L-Column ODS" 4.6×150 mm (by Chemicals Evaluation and Research Institute, Japan)
Sample preparation: 1/1000 dilution with methanol
Eluent A: 10 mM ammonium acetate-added water
Eluent B: 10 mM ammonium acetate-added methanol
Gradient: 0 min (A/B=30/70%)→10 min (30/70%)→55 min (0/100%)→65 min (0/100%)→66 min (30/70%)→75 min (30/70%) MS apparatus: "Agilent Technology 1100MS SL(G1946D)"
MS Detector: anion detector m/z 60-1600, UV 240 nm (9) Measurement of Content of Starting Internal Olefin in Internal Olefinsulfonate Salt The content of the starting internal olefin in internal olefinsulfonate salt was measured through GC. Concretely, ethanol and petroleum ether were added to an aqueous solution of the internal olefinsulfonate salt to be analyzed, and then extracted to separate the starting internal olefin in the petroleum ether phase. From the GC peak area thereof, the olefin amount was quantified.

The apparatus and the condition for analysis were as follows:
GC apparatus: "Agilent Technology 6850" (by Agilent Technology)
Column: "Ultra-Alloy-1HT Capillary Column" 15 m×250 µm×0.15 µm (by Frontier Labo)
Detector: hydrogen flame ion detector (FID)
Injection temperature: 300° C.
Detector temperature: 350° C.
He flow rate: 3.8 mL/min

(10) Measurement of Content of Inorganic Compound in Internal Olefinsulfonate Salt The content of the inorganic compound in internal olefinsulfonate salt was measured through potentiometric titration and neutralization titration. The content of $Na_2SO_4$ was quantified through potentiometric titration for the sulfate radical ($SO_4^{2-}$). The content of NaOH was quantified through neutralization titration with diluted hydrochloric acid.

(11) Measurement of Content of Internal Olefinsulfonate Salt with Sulfonate Group at 2-Position The bonding position of the sulfonate group in internal olefinsulfonate salt was determined through GC. Concretely, the obtained internal olefinsulfonate was reacted with trimethylsilyldiazomethane to give a methyl-esterified derivative, which was then separated into the constitutive components through GC. Based on the peak area ratio by mass of each component, the content of the internal olefinsulfonate salt with the sulfonate group positioned at the 2-position was calculated.

The apparatus and the condition for analysis were as follows:
GC apparatus: "Agilent Technology 6850" (by Agilent Technology)
Column: "HP-1 Capillary Column" 30 m×320 m×0.25 μm (by Agilent Technology)
Detector: hydrogen flame ion detector (FID)
Injection temperature: 300° C.
Detector temperature: 300° C.
He flow rate: 1.0 mL/min
Oven: 60° C. (0 min)→10° C./min→300° C. (10 min)

Production Example 1 (Production of CCE (1))

(1) Step of Cutting Treatment, Drying Treatment and Grinding Treatment of Cellulose As a starting cellulose, a sheet-like wood pulp (Tembec's Biofloc HV+, mean degree of polymerization, 1550) was used, and this was shredded into chips with a shredder "MSX2000-IVP440F" (by Meiko Shokai). Subsequently, this was dried at 80° C. for 12 hours to give a chip-like dry pulp having a water content of 0.18%.

Next, 920 g of the obtained, chip-like dry pulp was put into a batch-type shaking mill "FV-10" (by Chuo Kakohki: container total volume 33 L, 63 SUS304 rods of 30 mm and length 510 mm each having a circular cross section, packing ratio 70 vol %). At a frequency of 20 Hz, a total amplitude of 8 mm and a temperature of from 10 to 40° C., this was ground for 10 minutes to give 890 g of a cellulose powder (mean degree of polymerization 1233).

(2) Glycerolation Step 162.0 g of dimethyl sulfoxide (by Wako Pure Chemicals) and 33.2 g of tetra(n-butyl)ammonium fluoride trihydrate (TBAF, by Kanto Chemical) were put into a three-neck round-bottomed flask, and uniformly dissolved. To this, added was 3.0 g of the powdery cellulose obtained in the above, and stirred at room temperature for 1 hour and dissolved. Further, 1.0 g of finely-powdered potassium hydroxide (1.0 mol/AGU 1 mol) was added thereto and well dispersed. After this was heated up to 70° C. and while the reaction liquid was kept stirred in a nitrogen stream atmosphere, a solution previously prepared by mixing 6.1 g of glycidol (4.4 mol/AGU 1 mol) and 6.1 g of dimethyl sulfoxide was added thereto, taking 5 hours. After the addition, this was further kept stirred for 1 hour at 70° C., and the reaction was then stopped. After the reaction, 1.2 g of acetic acid (1.1 equivalents relative to KOH added before the reaction) was added for neutralization, then the reaction solution was cooled down to room temperature, and centrifuged, and then the resulting supernatant was put into a mixed solvent of ion-exchanged water/acetone/methanol=2/4/4 (by volume) (3 L, 25° C.). The precipitated polymer was collected through filtration, then washed with 1 L of the above-mentioned ion-exchanged water/acetone/methanol mixed solvent, and thereafter dried under reduced pressure (80° C., 0.03 kPa, 12 hours) to give 3.5 g of a glycerolated cellulose as a white solid.

(3) Step of Cationization, and Hydrocarbon Group-Containing Group Addition Reaction 67.0 g of an aqueous 70% dimethyl sulfoxide solution was put into a three-neck round-bottomed flask, and 1.0 g of the glycerolated cellulose obtained in the above was added thereto, stirred at room temperature and dissolved uniformly. Subsequently, 0.07 g of an aqueous 48% sodium hydroxide solution (0.2 mol/AGU 1 mol) was added thereto and stirred at room temperature. Subsequently, 0.43 g (0.5 mol/AGU 1 mol) of glycidyltrimethylammonium chloride (by Sakamoto Chemical Industry, water content 20% by mass, purity 80%) serving as a cationizing agent and 0.04 g (0.05 mol/AGU 1 mol) of 2-ethylhexyl glycidyl ether serving as a hydrocarbon group-containing group-introducing agent were added to the glycerolated cellulose solution with stirring, then heated up to 50° C. and reacted for 5 hours. Subsequently, the reaction liquid was neutralized with acetic acid in an amount of 1.1 equivalents relative to NaOH added before the reaction, then put into 500 mL of ethanol/isopropanol (7/3 by volume), and the precipitated polymer was collected through filtration, washed with 500 mL of the above-mentioned ethanol/isopropanol mixed solvent, and dried under reduced pressure (80° C., 0.03 kPa, 12 hours) to give 0.9 g of CCE (1) as a white solid.

The amount added of the glycerolating agent, that of the cationizing agent, and that of the hydrocarbon group-containing group-introducing agent, as well as the evaluation results of the degree of substitution of the obtained CCE (1), the viscosity of aqueous 1% solution thereof and the solubility in water thereof are shown in Table 1.

Production Example 2 (Production of CCE (2))

CCE (2) was obtained in the same manner as in Production Example 1, except that the amount added of the glycerolating agent, that of the cationizing agent and that of the hydrocarbon group-containing group-introducing agent were changed as in Table 1. The evaluation results are shown in Table 1.

Production Example 3 (Production of CCE (3))

(1) Step of Cutting Treatment, Drying Treatment and Grinding Treatment of Cellulose This is the same as the step of cutting treatment, drying treatment and grinding treatment of cellulose as in (1) in Example 1.

(2) Step of Glycerolation and Hydrocarbon Group-Containing Group Addition Reaction 111.0 g of dimethyl sulfoxide (by Wako Pure Chemicals) and 22.1 g of tetra(n-butyl)ammonium fluoride trihydrate "TBAF" (by Kanto Chemical) were put into a three-neck round-bottomed flask, and uniformly dissolved. To this, added was 2.0 g of the powdery cellulose obtained in the above, and stirred at room temperature for 1 hour and dissolved. Further, 0.69 g of finely-powdered potassium hydroxide (1.0 mol/AGU 1 mol) was added thereto and well dispersed. After this was heated up to 70° C. and while the reaction liquid was kept stirred in a nitrogen stream atmosphere, a solution previously prepared by dissolving 7.0 g of glycidol (7.7 mol/AGU 1 mol) and 0.09 g of 2-ethylhexyl glycidyl ether (by Tokyo Chemical) (0.04 mol/AGU 1 mol) in 7.09 g of dimethyl sulfoxide was added thereto, taking 5 hours. After the addition, this was further kept stirred at 70° C. for 1 hour, and the reaction was then stopped. After the reaction, 0.8 g of acetic acid (1.1 equivalents relative to KOH added before the reaction) was added for neutralization, then the reaction solution was cooled down to room temperature, and centrifuged, and then the resulting supernatant was put into a mixed solvent of ion-exchanged water/acetone/methanol=2/4/4 (by volume) (10 L, 25° C.). The precipitated polymer was collected through filtration, then washed with 1 L of the above-mentioned ion-exchanged water/acetone/methanol mixed solvent, and thereafter dried under reduced pressure (80° C., 0.03 kPa, 12 hours) to give 2.1 g of a glycerolated cellulose as a white solid.

(3) Step of Cationization 67.0 g of an aqueous 70% dimethyl sulfoxide solution was put into a three-neck round-bottomed flask, and 1.0 g of the glycerolated and hydrocarbon group-containing group-introduced cellulose obtained in the above was added thereto, stirred at room temperature and dissolved uniformly. Subsequently, 0.07 g of an aqueous 48% sodium hydroxide solution (0.2 mol/AGU 1 mol) was added thereto and stirred at room temperature. Subsequently, 0.48 g (0.59 mol/AGU 1 mol) of glycidyltrimethylammonium chloride (by Sakamoto Chemical Industry, water content 20% by mass, purity 80%) serving as a cationizing agent was added to the glycerolated cellulose solution with stirring, then heated up to 50° C. and reacted for 5 hours. Subsequently, the reaction liquid was neutralized with acetic acid in an amount of 1.1 equivalents relative to NaOH added before the reaction, then put into 500 mL of ethanol/isopropanol (7/3 by volume), and the precipitated polymer was collected through filtration, washed with 500 mL of the above-mentioned ethanol/isopropanol mixed solvent, and dried under reduced pressure (80° C., 0.03 kPa, 12 hours) to give 0.9 g of CCE (3) as a white solid.

The amount added of the glycerolating agent, that of the cationizing agent, and that of the hydrocarbon group-containing group-introducing agent, as well as the evaluation results of the obtained CCE (3) are shown in Table 1.

Production Examples 4 to 7 (Production of CCE (4) to (7))

CCE (4) to CCE (7) were obtained in the same manner as in Production Example 3, except that the amount added of the glycerolating agent, that of the cationizing agent and that of the hydrocarbon group-containing group-introducing agent were changed as in Table 1. The evaluation results are shown in Table 1.

Production Example 8 (Production of CCE (8))

(1) Step of Cutting Treatment, Drying Treatment and Grinding Treatment of Cellulose A sheet-like wood pulp (Tembec's Biofloc XV18, mean degree of polymerization, 1977) was pelletized into chips with a sheet pelletizer "SGG-220" (by Horai). Subsequently, this was dried at 80° C. for 12 hours to give a chip-like dry pulp having a water content of 0.18%. The obtained chip-like cellulose was put into an extreme mill "MX-1200X™ Model" (by Waring, total volume 150 mL), and ground at a rotation speed of 24000 rpm and at 20° C. for 30 seconds to give a floc cellulose (mean degree of polymerization 1977).

(2) Glycerolation Step 584 g of dimethyl sulfoxide (by Wako Pure Chemicals) and 116.2 g of tetra(n-butyl)ammonium fluoride trihydrate (TBAF, by Kanto Chemical) were put into a three-neck round-bottomed flask, and uniformly dissolved. To this, added was 7.0 g of the floc cellulose obtained in the above, and stirred at room temperature for 1 hour and dissolved. Further, 2.4 g of finely-powdered potassium hydroxide (1.0 mol/AGU 1 mol) was added thereto and well dispersed. After this was heated up to 70° C. and while the reaction liquid was kept stirred in a nitrogen stream atmosphere, a solution previously prepared by mixing 124.1 g of glycidol (38.8 mol/AGU 1 mol) and 124.1 g of dimethyl sulfoxide was added thereto, taking 5 hours. After the addition, this was further kept stirred for 1 hour at 70° C., and the reaction was then stopped. After the reaction, 2.8 g of acetic acid (1.1 equivalents relative to KOH added before the reaction) was added for neutralization, then the reaction solution was cooled down to room temperature, and centrifuged, and then the resulting supernatant was put into a mixed solvent of ion-exchanged water/acetone/methanol=2/4/4 (by volume) (10 L, 25° C.). The precipitated polymer was collected through filtration, then washed with 1 L of the above-mentioned ion-exchanged water/acetone/methanol mixed solvent, and thereafter dried under reduced pressure (80° C., 0.03 kPa, 12 hours) to give 13.0 g of a glycerolated cellulose as a white solid.

(3) Step of Cationization, and Hydrocarbon Group-Containing Group Addition Reaction 99.0 g of an aqueous 70% dimethyl sulfoxide solution was put into a three-neck round-bottomed flask, and 1.0 g of the glycerolated cellulose obtained in the above was added thereto, stirred at room temperature and dissolved uniformly. Subsequently, 0.15 g of an aqueous 20% sodium hydroxide solution (0.25 mol/AGU 1 mol) was added thereto and stirred at room temperature. Subsequently, 1.96 g (3.51 mol/AGU 1 mol) of glycidyltrimethylammonium chloride (by Sakamoto Chemical Industry, water content 20% by mass, purity 80%) serving as a cationizing agent and 0.04 g (0.07 mol/AGU 1 mol) of 2-ethylhexyl glycidyl ether serving as a hydrocarbon group-containing group-introducing agent were added to the glycerolated cellulose solution with stirring, then heated up to 50° C. and reacted for 5 hours. Subsequently, the reaction liquid was neutralized with acetic acid in an amount of 1.1 equivalents relative to NaOH added before the reaction, then put into 500 mL of ethanol/isopropanol (7/3 by volume), and the precipitated polymer was collected through filtration, washed with 500 mL of the above-mentioned ethanol/isopropanol mixed solvent, and dried under reduced pressure (80° C., 0.03 kPa, 12 hours) to give 0.9 g of CCE (8) as a white solid. The evaluation results are shown in Table 1.

Production Examples 9 to 13 (Production of CCE (9) to (13))

CCE (9) to CCE (13) were produced in the same manner as in Production Example 8, except that the step of cutting treatment, drying treatment and grinding treatment of cellulose, sheet-like wood pulp was changed to the method as in Production Example 1 and that the amount added of the glycerolating agent, that of the cationizing agent and that of the hydrocarbon group-containing group-introducing agent were changed as in Table 1. The evaluation results are shown in Table 1.

Production Examples 14 to 17 (Production of CCE (14) to (17))

CCE (14) to CCE (17) were produced in the same manner as in Production Example 3, except that the amount added of the glycerolating agent, that of the cationizing agent and that of the hydrocarbon group-containing group-introducing agent were changed as in Table 1. The evaluation results are shown in Table 1.

Production Examples 18 to 20 (Production of CCE (18) to (20))

CCE (18) to CCE (20) were produced in the same manner as in Production Example 8, except that the amount added of the glycerolating agent, that of the cationizing agent and that of the hydrocarbon group-containing group-introducing agent were changed as in Table 1. The evaluation results are shown in Table 1.

Isodecyl glycidyl ether used in Production Example 20 was produced according to the method described in Example 1 in Japanese Patent 3544134 except that 167.4 g of isodecyl alcohol was used in place of 167.4 g of dodecyl alcohol as the starting material.

Production Example 21 (Production of CCE (21))

CCE (21) was produced in the same manner as in Production Example 3, except that n-octyl chloride (by Wako Pure Chemicals) was used as the hydrocarbon group-containing group-introducing agent, and that the amount added of the glycerolating agent, that of the cationizing agent and that of the hydrocarbon group-containing group-introducing agent were changed as in Table 1. The evaluation results are shown in Table 1.

Production Example 22 (Production of CCE (22))

CCE (22) was produced in the same manner as in Production Example 3, except that stearyl glycidyl ether (by Kao) was used as the hydrocarbon group-containing group-introducing agent, and that the amount added of the glycerolating agent, that of the cationizing agent and that of the hydrocarbon group-containing group-introducing agent were changed as in Table 1. The evaluation results are shown in Table 1.

Production Example 23 (Production of CCE (23))

CCE (23) was produced in the same manner as in Production Example 3, except that n-dodecyl chloride (by Kanto Chemical) was used as the hydrocarbon group-containing group-introducing agent, and that the amount added of the glycerolating agent, that of the cationizing agent and that of the hydrocarbon group-containing group-introducing agent were changed as in Table 1. The evaluation results are shown in Table 1.

Production Example 24 (Production of CPGC (1))

(1) Step of Cutting Treatment, Drying Treatment and Grinding Treatment of Cellulose A cellulose powder (mean degree of polymerization 1233) was obtained in the same manner as in Production Example 1.

(2) Glycerolation Step 389.2 g of dimethyl sulfoxide (by Wako Pure Chemicals) and 77.5 g of tetra(n-butyl)ammonium fluoride trihydrate (TBAF, by Kanto Chemical) were put into a three-neck round-bottomed flask, and uniformly dissolved. To this, added was 7.0 g of the cellulose powder obtained in the above, and stirred at room temperature for 1 hour and dissolved. Further, 2.42 g of finely-powdered potassium hydroxide (1.0 mol/AGU 1 mol) was added thereto and well dispersed. After this was heated up to 70° C. and while the reaction liquid was kept stirred in a nitrogen stream atmosphere, a solution previously prepared by mixing 25.6 g of glycidol (8.0 mol/AGU 1 mol) and 25.6 g of dimethyl sulfoxide was added thereto, taking 5 hours. After the addition, this was further kept stirred for 1 hour at 70° C., and the reaction was then stopped.

Subsequently, this was neutralized with acetic acid, and the reaction solution was cooled down to room temperature, then centrifuged, and the resulting supernatant was put into a mixed solvent of ion-exchanged water/acetone/methanol=2/4/4 (by volume). The precipitated polymer was collected, and then dried under reduced pressure to give 8.82 g of a glycerolated cellulose as a white solid.

(3) Step of Cationization 166.7 g of an aqueous 50% dimethyl sulfoxide solution was put into a three-neck round-bottomed flask, and 2.5 g of the glycerolated cellulose obtained in the above was added thereto, stirred at room temperature and dissolved uniformly. Subsequently, 0.4 g of an aqueous 20% sodium hydroxide solution (0.2 mol/AGU 1 mol) was added thereto and stirred at room temperature. Subsequently, 1.46 g (0.8 mol/AGU 1 mol) of glycidyltrimethylammonium chloride (by Sakamoto Chemical Industry, water content 20% by mass, purity 80%) serving as a cationizing agent was added thereto with stirring, then heated up to 50° C. and reacted for 5 hours. Subsequently, the reaction liquid was neutralized with acetic acid, then put into ethanol, and the precipitated polymer was collected, and dried under reduced pressure to give 1.9 g of CPGC (1) as a white solid. The evaluation results are shown in Table 1.

Production Example 25 (Production of CPGC (2))

CPGC (2) was produced in the same manner as in Production Example 24, except that the amount added of glycidol and that of the cationizing agent were changed as in Table 1. The evaluation results are shown in Table 1.

Production Example 26 (Production of C-HPC)

(1) Chipping Step

A sheet-like wood pulp (Tembec's Biofloc HV+, mean degree of polymerization 1770, degree of crystallization 74%, water content 7.0%) was pelletized into chips of from 3 to 5 mm square, using a sheet pelletizer "SGG-220" (by Horai).

(2) Cationization Step 100 g of the chip-like pulp obtained in the above (1) was mixed with 60.8 g (0.65 mol/AGU 1 mol) of an aqueous glycidyl trimethylammonium chloride solution (by Sakamoto Chemical Industry, water content 20%, purity 80%) in a mortar, and then put into a batch-type shaking mill "MB-1" (by Chuo Kakohki: container total volume 3.5 L, 13 SUS304 rods of φ30 mm and length 218 mm each having a circular cross section, packing ratio 57%). This was ground for 12 minutes (frequency 20 Hz, amplitude 8 mm, temperature 30 to 70° C.) to give a powdery mixture of cellulose and GMAC.

The obtained powdery mixture was further mixed with 14.8 g (0.2 mol/AGU 1 mol) of an aqueous 48% sodium hydroxide solution in a mortar, and then put into the above-mentioned batch-type shaking mill. Under the same condition as above, this was ground for 120 minutes to give 175.6 g of a cationized cellulose.

(3) Hydroxypropylation Step

A kneader containing therein 100 g of the cationized cellulose obtained after ripening (unneutralized/unpurified product) was heated up to 70° C., and 40.8 g of propylene oxide (2.0 mol/AGU 1 mol, Kanto Chemical's special grade chemical) was dropwise added thereto with stirring, and reacted for 8 hours until propylene oxide was consumed and the reflux stopped.

After the reaction, the mixture was taken out of the kneader to be 140.8 g of a pale brown, crude C-HPC powder.

10.0 g of the crude C-HPC powder was sampled and neutralized with acetic acid. For the purpose of determining the degree of substitution with propyleneoxy group and that with cationized ethyleneoxy group, the neutralized product was purified through a dialytic membrane (molecular weight cutoff: 1000), and then the aqueous solution was freeze-dried to give a purified C-HPC.

The chlorine content in the thus-obtained pure C-HPC was 3.0%, as determined through elementary analysis. The hydroxypropoxy group content, as determined according to the above-mentioned "Analysis Method for Hydroxypropyl Cellulose", was 32.5%. The degree of substitution with cationized ethyleneoxy group and that with propyleneoxy group were 0.22 and 1.10, respectively.

TABLE 1

| | | Added Amount of Glycidol (mol/AGU*1) | Added Amount of Catonizing Agent (mol/AGU*1) | Added Amount of Hydrocarbon Group-Containing Group-Introducing Agent (mol/AGU*1) | Hydrocarbon Group-Containing Group-Introducing Agent | Degree of Substitution with Glycerol Group [MS(Gly)] | Degree of Substitution with Cationized Oxyalkylene Group [MS(N+)] |
|---|---|---|---|---|---|---|---|
| Production Example 1 | CCE(1) | 4.4 | 0.50 | 0.05 | 2EH-GE *2 | 0.79 | 0.14 |
| Production Example 2 | CCE(2) | 4.4 | 0.59 | 0.03 | 2EH-GE *2 | 0.79 | 0.13 |
| Production Example 3 | CCE(3) | 7.7 | 0.59 | 0.04 | 2EH-GE *2 | 0.96 | 0.10 |
| Production Example 4 | CCE(4) | 9.0 | 0.59 | 0.12 | 2EH-GE *2 | 0.50 | 0.10 |
| Production Example 5 | CCE(5) | 7.7 | 0.59 | 0.10 | 2EH-GE *2 | 0.79 | 0.11 |
| Production Example 6 | CCE(6) | 7.7 | 0.59 | 0.06 | 2EH-GE *2 | 1.09 | 0.09 |
| Production Example 7 | CCE(7) | 7.7 | 0.59 | 0.12 | 2EH-GE *2 | 0.77 | 0.08 |
| Production Example 8 | CCE(8) | 38.8 | 3.51 | 0.07 | 2EH-GE *2 | 2.05 | 0.23 |
| Production Example 9 | CCE(9) | 31.3 | 1.25 | 0.11 | 2EH-GE *2 | 1.92 | 0.11 |
| Production Example 10 | CCE(10) | 31.3 | 3.51 | 0.07 | 2EH-GE *2 | 1.78 | 0.35 |
| Production Example 11 | CCE(11) | 35.1 | 2.67 | 0.11 | 2EH-GE *2 | 2.18 | 0.23 |
| Production Example 12 | CCE(12) | 35.1 | 6.67 | 0.11 | 2EH-GE *2 | 2.03 | 0.45 |
| Production Example 13 | CCE(13) | 35.1 | 10.0 | 0.11 | 2EH-GE *2 | 2.04 | 0.65 |
| Production Example 14 | CCE(14) | 11.8 | 0.59 | 0.12 | 2EH-GE *2 | 2.16 | 0.12 |
| Production Example 15 | CCE(15) | 7.7 | 1.77 | 0.12 | 2EH-GE *2 | 0.75 | 0.30 |
| Production Example 16 | CCE(16) | 7.7 | 1.77 | 0.12 | 2EH-GE *2 | 1.00 | 0.28 |
| Production Example 17 | CCE(17) | 11.8 | 1.77 | 0.12 | 2EH-GE *2 | 2.16 | 0.31 |
| Production Example 18 | CCE(18) | 38.8 | 25.0 | 0.07 | 2EH-GE *2 | 2.37 | 0.07 |
| Production Example 19 | CCE(19) | 31.3 | 25.0 | 0.07 | 2EH-GE *2 | 2.00 | 0.07 |
| Production Example 20 | CCE(20) | 35.1 | 2.67 | 0.11 | ID-GE*3 | 1.99 | 0.18 |
| Production Example 21 | CCE(21) | 7.7 | 0.59 | 0.12 | n-octyl chloride | 1.00 | 0.12 |
| Production Example 22 | CCE(22) | 7.7 | 0.59 | 0.12 | C18-GE *4 | 0.92 | 0.15 |
| Production Example 23 | CCE(23) | 7.7 | 0.23 | 0.59 | n-dodecyl chloride | 0.78 | 0.11 |
| Production Example 24 | CPGC(1) | 8.0 | 0.80 | — | — | 1.31 | 0.14 |
| Production Example 25 | CPGC(2) | 8.0 | 0.40 | — | — | 1.31 | 0.07 |
| Production Example 26 | C-HPC | 2.0*5 | 0.65 | — | — | 1.10*6 | 0.22 |

TABLE 1-continued

|  |  | Degree of Substitution with Hydrocarbon Group-Containing Group [MS(HC)] | Hydrocarbon Group-Containing Group | Cation Charge Density [mmol/g] | Mean Degree of Polymerization [n] | Viscosity of Aqueous 1% Solution [mPa · s] | Solubility in Water |
|---|---|---|---|---|---|---|---|
| Production Example 1 | CCE(1) | 0.002 | 2-ethylhexyl group | 0.58 | 1233 | 303 | A |
| Production Example 2 | CCE(2) | 0.002 | 2-ethylhexyl group | 0.54 | 1233 | 256 | A |
| Production Example 3 | CCE(3) | 0.010 | 2-ethylhexyl group | 0.41 | 1233 | 109 | A |
| Production Example 4 | CCE(4) | 0.010 | 2-ethylhexyl group | 0.47 | 1233 | 120 | A |
| Production Example 5 | CCE(5) | 0.020 | 2-ethylhexyl group | 0.45 | 1233 | 66 | A |
| Production Example 6 | CCE(6) | 0.030 | 2-ethylhexyl group | 0.35 | 1233 | 294 | A |
| Production Example 7 | CCE(7) | 0.040 | 2-ethylhexyl group | 0.34 | 1233 | 466 | A |
| Production Example 8 | CCE(8) | 0.013 | 2-ethylhexyl group | 0.66 | 1977 | 583 | A |
| Production Example 9 | CCE(9) | 0.016 | 2-ethylhexyl group | 0.34 | 1233 | 179 | A |
| Production Example 10 | CCE(10) | 0.008 | 2-ethylhexyl group | 1.00 | 1233 | 49 | A |
| Production Example 11 | CCE(11) | 0.025 | 2-ethylhexyl group | 0.64 | 1233 | 138 | A |
| Production Example 12 | CCE(12) | 0.026 | 2-ethylhexyl group | 1.18 | 1233 | 124 | A |
| Production Example 13 | CCE(13) | 0.020 | 2-ethylhexyl group | 1.57 | 1233 | 123 | A |
| Production Example 14 | CCE(14) | 0.040 | 2-ethylhexyl group | 0.34 | 1233 | 50 | A |
| Production Example 15 | CCE(15) | 0.030 | 2-ethylhexyl group | 1.11 | 1233 | 210 | A |
| Production Example 16 | CCE(16) | 0.020 | 2-ethylhexyl group | 0.99 | 1233 | 95 | A |
| Production Example 17 | CCE(17) | 0.040 | 2-ethylhexyl group | 0.82 | 1233 | 33 | A |
| Production Example 18 | CCE(18) | 0.022 | 2-ethylhexyl group | 0.20 | 1734 | 1977 | A |
| Production Example 19 | CCE(19) | 0.005 | 2-ethylhexyl group | 0.22 | 1233 | 49 | A |
| Production Example 20 | CCE(20) | 0.011 | isodecyl group | 0.53 | 1233 | 111 | A |
| Production Example 21 | CCE(21) | 0.040 | n-octyl group | 0.47 | 1233 | 91 | A |
| Production Example 22 | CCE(22) | 0.030 | stearyl group | 0.57 | 1233 | >20,000 | C |
| Production Example 23 | CCE(23) | 0.01 | n-dodecyl group | 0.46 | 1233 | —*7 | A |
| Production Example 24 | CPGC(1) | — | — | 0.50 | 1233 | 221 | A |
| Production Example 25 | CPGC(2) | — | — | 0.26 | 1233 | 219 | A |
| Production Example 26 | C-HPC | — | — | —*7 | 1770 | —*7 | —*7 |

*1 molar number relative to 1 mol of anhydroglucose unit
*2 2-ethylhexyl glycidyl ether
*3 isodecyl glycidyl ether
*4 stearyl glycidyl ether
*5 added amount of propylene oxide (mol/AGU)
*6 degree of substitution with oxypropylene group
*7 unmeasured Production Example A (Production of Starting Internal Olefin A)

7000 g (28.9 mol) of 1-hexadecanol (Kalcol 6098, by Kao) and 700 g (10% by mass relative to the starting alcohol) of γ-alumina (by STERM Chemicals, Inc.) serving as a solid acid catalyst were put into a flask equipped with a stirrer, and while nitrogen (7000 mL/min) was circulated inside the system at 280° C. with stirring, this was reacted for 5 hours. After the reaction, the alcohol conversion was 100%, and the C16 internal olefin purity was 99.7%. The obtained, crude internal olefin was transferred into a distillation flask and distilled therein at 136 to 160° C./4.0 mmHg to give an internal olefin having a carbon number of 16 and having an olefin purity of 100%. The double bond distribution of the thus-obtained internal olefin was: 0.5% by mass at C1, 16.5% by mass at C2, 15.4% by mass at C3, 16.4% by mass at C4, 17.2% by mass at C5, 14.2% by mass at C6, and 19.8% by mass at C7 and C8 in total.

Production Example B (Production of Starting Internal Olefin B)

7000 g (25.9 mol) of 1-octadecanol (Kalcol 8098, by Kao) and 1050 g (15% by mass relative to the starting alcohol) of γ-alumina (by STERM Chemicals, Inc.) serving as a solid acid catalyst were put into a flask equipped with a stirrer, and while nitrogen (7000 mL/min) was circulated inside the system at 285° C. with stirring, this was reacted for 13 hours. After the reaction, the alcohol conversion was 100%, and the C18 internal olefin purity was 98.5%. The obtained, crude internal olefin was transferred into a distillation flask and distilled therein at 148 to 158° C./0.5 mmHg to give an internal olefin having a carbon number of 18 and having an olefin purity of 100%. The double bond distribution of the thus-obtained internal olefin was: 0.7% by mass at C1, 16.9% by mass at C2, 15.9% by mass at C3, 16.0% by mass at C4, 14.7% by mass at C5, 11.2% by mass at C6, 10.2% by mass at C7, and 14.6% by mass at C8 and C9 in total.

Production Example C (Production of Starting Internal Olefin C)

6000 g (35.6 mol) of 1-dodecene (Linealene 12, by Idemitsu Kosan) and 180 g (3.0% by mass relative to the starting 1-dodecene) of β-zeolite (by Zeolyst) serving as a solid acid catalyst were put into a flask equipped with a stirrer, and while nitrogen (200 mL/min) was circulated inside the system at 120° C. with stirring, this was reacted for 12.5 hours. After the reaction, the internal isomerization of α-olefin was 98.4%, and the C12 internal olefin purity was 92.1%. The obtained, crude internal olefin was transferred into a distillation flask and distilled therein at 134 to 138° C./75.0 to 78.8 mmHg to give an internal olefin having a carbon number of 12 and having an olefin purity of 100%. The double bond distribution of the thus-obtained internal olefin was: 0.5% by mass at C1, 33.1% by mass at C2, 23.7% by mass at C3, 21.2% by mass at C4, 15.0% by mass at C5, and 6.8% by mass at C6.

Production Example D (Production of Starting Internal Olefin D)

7000 g (28.9 mol) of 1-hexadecanol (Kalcol 6098, by Kao) and 700 g (10% by mass relative to the starting alcohol) of γ-alumina (by STERM Chemicals, Inc.) serving as a solid acid catalyst were put into a flask equipped with a stirrer, and while nitrogen (7000 mL/min) was circulated inside the system at 280° C. with stirring, this was reacted for 3 hours. After the reaction, the alcohol conversion was 100%, and the C16 internal olefin purity was 99.6%. The obtained, crude internal olefin was transferred into a distillation flask and distilled therein at 136 to 160° C./4.0 mmHg to give an internal olefin having a carbon number of 16 and having an olefin purity of 100%. The double bond distribution of the thus-obtained internal olefin was: 1.8% by mass at C1, 30.4% by mass at C2, 23.9% by mass at C3, 16.8% by mass at C4, 12.0% by mass at C5, 7.4% by mass at C6, and 7.8% by mass at C7 and C8 in total.

Production Example E (Production of Starting Internal Olefin E)

7000 g (25.9 mol) of 1-octadecanol (Kalcol 8098, by Kao) and 700 g (10% by mass relative to the starting alcohol) of γ-alumina (by STERM Chemicals, Inc.) serving as a solid acid catalyst were put into a flask equipped with a stirrer, and while nitrogen (7000 mL/min) was circulated inside the system at 280° C. with stirring, this was reacted for 10 hours. After the reaction, the alcohol conversion was 100%, and the C18 internal olefin purity was 98.2%. The obtained, crude internal olefin was transferred into a distillation flask and distilled therein at an internal temperature of 148 to 158° C./0.5 mmHg to give an internal olefin having a carbon number of 18 and having an olefin purity of 100%. The double bond distribution of the thus-obtained internal olefin was: 0.8% by mass at C1, 31.3% by mass at C2, 22.9% by mass at C3, 15.5% by mass at C4, 10.8% by mass at C5, 7.2% by mass at C6, 5.3% by mass at C7, and 6.2% by mass at C8 and C9 in total.

Production Example 27 (Production of Internal Olefinsulfonate Salt (1))

Using a thin-film sulfonation reactor (inner diameter 14 mmφ, length 4 m), the internal olefin having a carbon number of 16 obtained in Production Example A was sulfonated with sulfur trioxide gas having an $SO_3$ concentration of 2.8% by volume, while cooling water at 20° C. was kept circulated through the outer jacket. The reaction molar ratio of $SO_3$/internal olefin was set at 1.09.

Thus obtained, the sulfonated product was added to an aqueous alkali solution to which sodium hydroxide had been added in an amount to be 1.2 molar times the theoretical acid value (AV), and neutralized therein with stirring at 30° C. for 1 hour. The neutralized product was heated for one hour in an autoclave at 160° C. for hydrolysis, thereby giving a crude product of sodium internal olefinsulfonate having a carbon number of 16.

300 g of the obtained crude product was transferred into a separating funnel, 300 mL of ethanol was added thereto, and petroleum ether was added thereto in an amount of 300 mL every time for extraction to remove the oil-soluble impurities. During this, the inorganic compound (the main component is salt cake) that had been precipitated in the oil/water interface through ethanol addition was also separated and removed from the aqueous phase through the oil/water separation operation. This operation was repeated three times. The aqueous phase was evaporated into dryness to give a sodium internal olefinsulfonate having a carbon number of 16 (internal olefinsulfonate salt (1)). The ratio by mass of hydroxy form/olefin form, and the content of the internal olefinsulfonate salt with the sulfonate radical at the 2-position are shown in Table 2. The content of the starting internal olefin was less than 100 ppm (less than the detection limit in GC) and the content of the inorganic compound was 1.3% by mass.

Production Example 28 (Production of Internal Olefinsulfonate (2))

A sodium internal olefinsulfonate having a carbon number of 18 (internal olefinsulfonate (2)) was obtained under the same condition as that in Production Example 27 except that the internal olefin having a carbon number of 18 obtained in Production Example B was used. The ratio by mass of hydroxy form/olefin form, and the content of the internal olefinsulfonate salt with the sulfonate radical at the 2-position are shown in Table 2. The content of the starting internal olefin was less than 100 ppm (less than the detection limit in GC) and the content of the inorganic compound was 1.7% by mass.

Production Example 29 (Production of Internal Olefinsulfonate (3))

A sodium internal olefinsulfonate having a carbon number of 12 (internal olefinsulfonate (3)) was obtained under the same condition as that in Production Example 27 except that the internal olefin having a carbon number of 12 obtained in Production Example C was used. The ratio by mass of hydroxy form/olefin form, and the content of the internal olefinsulfonate salt with the sulfonate radical at the 2-position are shown in Table 2. The content of the starting internal olefin was less than 100 ppm (less than the detection limit in GC) and the content of the inorganic compound was 0.2% by mass.

Production Example 30 (Production of Internal Olefinsulfonate (4))

A sodium internal olefinsulfonate having a carbon number of 16 (internal olefinsulfonate (4)) was obtained under the same condition as that in Production Example 27 except that the internal olefin having a carbon number of 16 obtained in Production Example D was used. The ratio by mass of hydroxy form/olefin form, and the content of the internal olefinsulfonate salt with the sulfonate radical at the 2-position are shown in Table 2. The content of the starting internal olefin was less than 100 ppm (less than the detection limit in GC) and the content of the inorganic compound was 1.9% by mass.

Production Example 31 (Production of Internal Olefinsulfonate (5))

A sodium internal olefinsulfonate having a carbon number of 18 (internal olefinsulfonate (5)) was obtained under the same condition as that in Production Example 27 except that the internal olefin having a carbon number of 18 obtained in Production Example E was used. The ratio by mass of hydroxy form/olefin form, and the content of the internal olefinsulfonate salt with the sulfonate radical at the 2-position are shown in Table 2. The content of the starting internal olefin was less than 100 ppm (less than the detection limit in GC) and the content of the inorganic compound was 0.9% by mass.

(Evaluation)

A composition comprising the components mentioned below was taken in a beaker, heated at 80° C., mixed, and after its uniform dissolution was confirmed, this was cooled to give a plain shampoo. Artificial hair tresses (20 g, 20 cm) were washed with the obtained plain shampoo. The washed hair tresses were well wetted with warm water at 35 to 40° C., then again washed with the hair shampoo (0.5 g) having the composition shown in Table 3, and rinsed with warm water (35 to 40° C.). Five panelists evaluated the smootheness feeling, the long-lasting smoothness feeling and the coated feeling in hair rinsing, according to the evaluation criteria and the evaluation methods mentioned below. In addition, the comprehensive evaluation of the hair shampoo as a hair wash composition was made similarly according to the following evaluation criteria.

(Composition of Plain Shampoo)

| (Components) | (%) |
|---|---|
| Sodium polyoxyethylene laurylether sulfate | 11.3 |
| (42% as Kao's "Emal E-27C" (active ingredient 27%) | |
| Coconut oil fatty acid N-methylethanolamide | 3.0 |
| (Kao's "Aminone C-11S") | |

TABLE 2

| | | Starting Internal Olefin | | | Internal Olefinsulfonate Salt | |
|---|---|---|---|---|---|---|
| | | Production Example | Carbon Number | 2-positioned double bond (%) | HAS/IOS (by mass) | Content of Internal Olefinsulfonate Salt with sulfonate radical at 2-position |
| Production Example 27 | Internal Olefinsulfonate (1) | A | 16 | 16.5 | 80/20 | 9.3 |
| Production Example 28 | Internal Olefinsulfonate (2) | B | 18 | 16.9 | 80/20 | 9.6 |
| Production Example 29 | Internal Olefinsulfonate (3) | C | 12 | 33.1 | 80/20 | 21.0 |
| Production Example 30 | Internal Olefinsulfonate (4) | D | 16 | 30.4 | 80/20 | 20.3 |
| Production Example 31 | Internal Olefinsulfonate (5) | E | 18 | 31.3 | 80/20 | 21.4 |

Examples 1 to 14 (Production and Evaluation of Hair Shampoo)

(Production)

Using any of CCE (1) to (13) and (20), and as surfactants, sodium polyoxyethylene alkylsulfate (Kao's "Emal 170J" (aqueous 70% solution, mean addition molar number of oxyethylene groups: 1, alkyl chain length: C10-16), coconut oil fatty acid amide propylcarbobetaine (Kao's "Amphitol 55AB" (aqueous 30% solution)) and coconut oil fatty acid monoethanolamide (Kawaken Fine Chemical's "Amizol CME") and according to an ordinary method, hair shampoos were prepared so that the effective content of each component therein could be as in Table 3. Concretely, CCE was dissolved in water to prepare a 2% polymer solution. Separately, the other components than the polymer were taken in a beaker, heated at 80° C., then stirred and uniformly dissolved, and the 2% polymer solution was added thereto, uniformly mixed, cooled, and finally water that had been evaporated away by heating was replenished to give a hair shampoo.

-continued

| (Components) | (%) |
|---|---|
| Citric acid | 0.2 |
| Methylparaben | 0.3 |
| Pure water | balance |
| Total | 100.0 |

(Evaluation Criteria)
Smoothness Property:

7: Excellent smoothness with no friction.

6: Good smoothness with extremely little friction as compared with the hair shampoo of Comparative Example 5.

5: Good smoothness with little friction as compared with the hair shampoo of Comparative Example 5.

4: Relatively good smoothness with relatively little friction as compared with the hair shampoo of Comparative Example 5.

3: Average (smoothness in rinsing of the hair shampoo of Comparative Example 5 to be mentioned below).

2: Poor smoothness with feeling of squeakiness as compared with the hair shampoo of Comparative Example 5.

1: No smoothness at all with feeling of serious squeakiness as compared with the hair shampoo of Comparative Example 5.

Long-Lasting Smoothness:

7: smoothness was long-lasting for 50 seconds or more.

6: smoothness was long-lasting for 30 seconds or more but less than 50 seconds.

5: smoothness was long-lasting for 20 seconds or more but less than 30 seconds.

4: smoothness was long-lasting for 10 seconds or more but less than 20 seconds.

3: smoothness was long-lasting for 5 seconds or more but less than 10 seconds.

2: smoothness was long-lasting for 1 second or more but less than 5 seconds.

1: smoothness was long-lasting for less than 1 second.

Coated Feeling in Rinsing:

7: Extremely excellent coated feeling in rinsing as compared with the hair shampoo of Comparative Example 4. the hair shampoo of Comparative Example 4.

5: Good coated feeling in rinsing as compared with the hair shampoo of Comparative Example 4.

4: Relatively good coated feeling in rinsing as compared with the hair shampoo of Comparative Example 4.

3: Average (coated feeling in rinsing in use of the hair shampoo of Comparative Example 4 to be mentioned below).

2: Poor coated feeling in rinsing as compared with the hair shampoo of Comparative Example 4.

1: No coated feeling at all in rinsing.

(Evaluation Method)

The scores of the evaluation results made by the five panelists were averaged to give the score point of each sample.

Comparative Examples 1 to 5 (Production and Evaluation of Hair Shampoo)

Using any of CCE (21) to (23) produced in Production Examples 21 to 23, CPGC (1) produced in Production Example 24, and cationized hydroxyethyl cellulose (C-HEC, Kao's "POIZ C-80M") and in the same manner as in Example 1, hair shampoos as in Table 3 were prepared and evaluated. The results are shown in Table 3.

TABLE 3

| Hair Shampoo | Type of Polymer | Polymer | Sodium Polyoxy-ethylene (1) Alkyl Ether Sulfate[1] | Coconut Oil Fatty Acid Mono-ethanol-amide[2] | Coconut Oil Fatty Acid Amide Propyl-betaine[3] | Sodium Chloride | pH Regulator | Pure Water | Smooth-ness | Long-lasting smmooth-ness | Coated Feeling |
|---|---|---|---|---|---|---|---|---|---|---|---|
| Example 1 | CCE(1) | 0.3 | 13.0 | 0.3 | 1.5 | 0.8 | adequate dose | Balance | 5.0 | 5.6 | 5.6 |
| Example 2 | CCE(2) | 0.3 | 13.0 | 0.3 | 1.5 | 0.8 | | | 5.6 | 4.8 | 4.8 |
| Example 3 | CCE(3) | 0.3 | 13.0 | 0.3 | 1.5 | 0.8 | | | 5.2 | 5.0 | 5.6 |
| Example 4 | CCE(4) | 0.3 | 13.0 | 0.3 | 1.5 | 0.8 | | | 4.6 | 5.6 | 5.0 |
| Example 5 | CCE(5) | 0.3 | 13.0 | 0.3 | 1.5 | 0.8 | | | 5.2 | 5.2 | 5.6 |
| Example 6 | CCE(6) | 0.3 | 13.0 | 0.3 | 1.5 | 0.8 | | | 5.0 | 5.0 | 5.0 |
| Example 7 | CCE(7) | 0.3 | 13.0 | 0.3 | 1.5 | 0.8 | | | 5.0 | 5.0 | 5.0 |
| Example 8 | CCE(8) | 0.3 | 13.0 | 0.3 | 1.5 | 0.8 | | | 6.4 | 6.4 | 6.4 |
| Example 9 | CCE(9) | 0.3 | 13.0 | 0.3 | 1.5 | 0.8 | | | 5.0 | 5.0 | 5.4 |
| Example 10 | CCE(10) | 0.3 | 13.0 | 0.3 | 1.5 | 0.8 | | | 4.6 | 4.6 | 5.0 |
| Example 11 | CCE(11) | 0.3 | 13.0 | 0.3 | 1.5 | 0.8 | | | 6.0 | 6.0 | 6.0 |
| Example 12 | CCE(12) | 0.3 | 13.0 | 0.3 | 1.5 | 0.8 | | | 5.6 | 4.6 | 5.0 |
| Example 13 | CCE(13) | 0.3 | 13.0 | 0.3 | 1.5 | 0.8 | | | 5.0 | 5.0 | 4.6 |
| Example 14 | CCE(20) | 0.3 | 13.0 | 0.3 | 1.5 | 0.8 | | | 4.6 | 5.0 | 5.0 |
| Comparative Example 1 | CCE(21) | 0.3 | 13.0 | 0.3 | 1.5 | 0.8 | adequate dose | balance | 5.0 | 4.6 | 3.6 |
| Comparative Example 2 | CCE(22) | 0.3 | 13.0 | 0.3 | 1.5 | 0.8 | | | 2.6 | 3.0 | 2.0 |
| Comparative Example 3 | CCE(23) | 0.3 | 13.0 | 0.3 | 1.5 | 0.8 | | | 5.0 | 4.6 | 3.6 |
| Comparative Example 4 | CPGC(1) | 0.3 | 13.0 | 0.3 | 1.5 | 0.8 | | | 4.2 | 4.4 | 3.0 |
| Comparative Example 5 | C-HEC | 0.3 | 13.0 | 0.3 | 1.5 | 0.8 | | | 3.0 | 3.0 | 2.0 |

[1] Kao's "Emal 170J" (active ingredient 70%), 18.6% added

[2] Kawaken Fine Chemical's "Amizol CME"

[3] Kao's "Amphitol 55AB" (active ingredient 30%), 5.0% added

From Table 3, it is known that the hair wash composition using any of CCE (1) to (13) and (20) of the present invention can give an excellent smoothness property and its long-lasting smoothness and a good coated feeling in rinsing.

Example 15 (Skin Cleanser; Body Shampoo)

A body shampoo having the composition mentioned below was produced according to an ordinary method.

Both hands were wetted, 0.5 mL of the produced body shampoo was applied to the both hands, bubbled, then the both hands were rinsed with running water for 10 seconds, the droplets were wiped away from the hands with a towel, and after dried, the skin touch was evaluated.

As a result, the skin washed with the body shampoo and dried had an excellent moisturizing feeling.

| (Components) | (%) |
| --- | --- |
| Sodium polyoxyethylene alkyl ether sulfate *1 | 6.2 |
| Sodium cocoylisethionate *2 | 5.8 |
| Coconut oil fatty acid amide propylbetaine *3 | 3.7 |
| Glycerin | 3.2 |
| Lauric acid | 4.0 |
| Myristic acid | 0.5 |
| Palmitic acid | 1.5 |
| Stearic acid | 1.5 |
| CCE (1) | 0.2 |
| Potassium hydroxide | adequate dose *4 |
| Fragrance, Preservative | adequate dose |
| Pure water | balance |
| Total | 100.0 |

*1: Kao's "Emal 270J" (active ingredient 70%) (In the above composition, the content is in terms of sodium polyoxyethylene alkyl ether sulfate.)
*2: NOF's "Diapon CI" (active ingredient 100%)
*3: Kao's "Amphitol 55AB" (active ingredient 30%)
*4: The pH of the body shampoo was controlled to be 7.3.

(In the above composition, the content is in terms of coconut oil fatty acid amide propylbetaine.)

Example 16 (Face Wash)

A face wash having the composition mentioned below was produced, and evaluated in the same manner as in Example 15. As a result, the skin washed with the face wash and dried had an excellent moisturizing feeling.

| (Components) | (%) |
| --- | --- |
| Sodium cocoylglycinate *1 | 9.4 |
| Sodium cocoamphoacetate *2 | 2.5 |
| Coconut oil fatty acid amide propylbetaine*3 | 1.7 |
| Lauric acid | 2.0 |
| Glycerin | 6.0 |
| CCE (1) | 0.3 |
| Fragrance, Preservative | adequate dose |
| pH regulator | adequate dose *4 |
| Pure water | balance |
| Total | 100.0 |

*1: Ajinomoto's "AMILITE GCS-11" (active ingredient 100%)
*2: Nikko Chemical's "NIKKOL AM-101" (active ingredient 40%) (In the above composition, the content is in terms of sodium cocoamphoacetate.)
*3: Kao's "Amphitol 55AB" (active ingredient 30%) (In the above composition, the content is in terms of coconut oil fatty acid amide propylbetaine.)
*4: The pH of the face wash was controlled to be 9.0, using citric acid and sodium hydroxide.

Example 17 (Face Wash)

A face wash having the composition mentioned below was produced and evaluated in the same manner as in Example 15. As a result, the skin washed with the face wash and dried had an excellent moisturizing feeling.

| (Components) | (%) |
| --- | --- |
| Sodium cocoylmethyltaurate *1 | 1.4 |
| Lauric acid | 28.2 |
| Myristic acid | 2.8 |
| Palmitic acid | 3.1 |
| PEG-32 *2 | 2.0 |
| Glycerin | 16.0 |
| CCE (1) | 0.3 |
| Fragrance, Preservative | adequate dose |
| pH regulator | adequate dose *3 |
| Pure water | balance |
| Total | 100.0 |

*1: Nikko Chemical's "NIKKOL CMT-30" (active ingredient 30%) (In the above composition, the content is in terms of sodium cocoylmethyltaurate.)
*2: NOF's "PEG#1500"
*3: The pH of the face wash was controlled to be 9.0, using citric acid and sodium hydroxide.

Examples 18 to 29, Comparative Example 6 (Production and Evaluation of Oil Agent-Containing Hair Shampoo)

Using any of CCE (2), (3), (8) to (13), (17) to (20) and CPGC (2), a hair shampoo was prepared to have the composition shown in Table 4, according to an ordinary method.

Concretely, CCE or CPGC was dissolved or uniformly dispersed in water, adequate amounts of water and surfactant were taken in a beaker, and uniformly mixed under heat at 60° C., and then cooled down to 50° C. An oily agent was added thereto, uniformly mixed, and cooled down to 40° C. A pearly agent was added thereto, stirred and emulsified for 30 minutes and cooled. Finally, water that had been evaporated away by heating was replenished, and the pH of the composition was measured. Using a pH regulator (aqueous 50% citric acid solution), the pH was controlled to be 5.

Hair tresses (20 g, 20 cm) were washed with the plain shampoo described in Example 1, then fully wetted with warm water at 35 to 40° C., 0.5 g of the shampoo of Examples 18 to 29 or Comparative Example 6 was applied thereto, and the hair tresses were thus shampooed therewith for 1 minute. Subsequently, the hair tresses were rinsed with warm water for 30 seconds, water was wiped away with a towel, the hair tresses were then combed and dried with warm air from a hair drier, and combed for final finish.

Five panelists evaluated the hair tresses in point of the finger-combability in hair washing, the smoothness and the long lasting smoothness in rinsing, and the moist feeling and the uniformity after drying, according to the evaluation criteria and the evaluation methods mentioned below. The evaluation results are shown in Table 4. The uniformity after drying means that the feeling from the hair root to the hair tip of hair tresses is uniform.

(Evaluation Criteria, Evaluation Methods)
Finger-Combability in Washing

5: Extremely good finger-Combability as compared with the hair shampoo of Comparative Example 6.

4: Good finger-Combability as compared with the hair shampoo of Comparative Example 6.

3: Average (finger-Combability in washing with the hair shampoo of Comparative Example 6).

2: Bad finger-Combability as compared with the hair shampoo of Comparative Example 6.

1: Extremely bad finger-Combability as compared with the hair shampoo of Comparative Example 6.

Smoothness in Rinsing

5: Extremely good Smoothness as compared with the hair shampoo of Comparative Example 6.

4: Good Smoothness as compared with the hair shampoo of Comparative Example 6.

3: Average (Smoothness in rinsing with the hair shampoo of Comparative Example 6).

2: Bad Smoothness as compared with the hair shampoo of Comparative Example 6.

1: Extremely bad Smoothness as compared with the hair shampoo of Comparative Example 6.

Long-Lasting Smoothness:

5: Extremely good long-lasting smoothness as compared with the hair shampoo of Comparative Example 6.

4: Good long-lasting smoothness as compared with the hair shampoo of Comparative Example 6.

3: Average (long-lasting smoothness with the hair shampoo of Comparative Example 6).

2: Bad long-lasting smoothness as compared with the hair shampoo of Comparative Example 6.

1: Extremely bad long-lasting smoothness as compared with the hair shampoo of Comparative Example 6.

Moist Feeling after Drying

5: Extremely good moist feeling as compared with the hair shampoo of Comparative Example 6.

4: Good moist feeling as compared with the hair shampoo of Comparative Example 6.

3: Average (moist feeling after drying with the hair shampoo of Comparative Example 6).

2: Bad moist feeling as compared with the hair shampoo of Comparative Example 6.

1: Extremely bad moist feeling as compared with the hair shampoo of Comparative Example 6.

Uniformity after Drying

5: Extremely good uniformity as compared with the hair shampoo of Comparative Example 6.

4: Good Uniformity as Compared with the Hair Shampoo of Comparative Example 6.

3: Average (uniformity after drying with the hair shampoo of Comparative Example 6).

2: Hair tips scattering as compared with the hair shampoo of Comparative Example 6.

1: Noticeable hair tips scattering as compared with the hair shampoo of Comparative Example 6.

TABLE 4

| Hair Wash Composition (hair shampoo) | | | Example | | | | | | | | | | | | Comparative Example |
|---|---|---|---|---|---|---|---|---|---|---|---|---|---|---|---|
| | | | 18 | 19 | 20 | 21 | 22 | 23 | 24 | 25 | 26 | 27 | 28 | 29 | 6 |
| Composition (mass %) | Polymer | CCE(2) | 0.3 | | | | | | | | | | | | |
| | | CCE(3) | | 0.3 | | | | | | | | | | | |
| | | CCE(8) | | | 0.3 | | | | | | | | | | |
| | | CCE(9) | | | | 0.3 | | | | | | | | | |
| | | CCE(10) | | | | | 0.3 | | | | | | | | |
| | | CCE(11) | | | | | | 0.3 | | | | | | | |
| | | CCE(12) | | | | | | | 0.3 | | | | | | |
| | | CCE(13) | | | | | | | | 0.3 | | | | | |
| | | CCE(17) | | | | | | | | | 0.3 | | | | |
| | | CCE(18) | | | | | | | | | | 0.3 | | | |
| | | CCE(19) | | | | | | | | | | | 0.3 | | |
| | | CCE(20) | | | | | | | | | | | | 0.3 | |
| | | CPGC(2) | | | | | | | | | | | | | 0.3 |
| | Surfactant | sodium laureth(1) sulfate*[1] | 13.0 | 13.0 | 13.0 | 13.0 | 13.0 | 13.0 | 13.0 | 13.0 | 13.0 | 13.0 | 13.0 | 13.0 | 13.0 |
| | | coconut oil fatty acid amide propylbetaine*[2] | 1.5 | 1.5 | 1.5 | 1.5 | 1.5 | 1.5 | 1.5 | 1.5 | 1.5 | 1.5 | 1.5 | 1.5 | 1.5 |
| | | coconut oil fatty acid monoethanolamide *[3] | 0.3 | 0.3 | 0.3 | 0.3 | 0.3 | 0.3 | 0.3 | 0.3 | 0.3 | 0.3 | 0.3 | 0.3 | 0.3 |
| | Oil Agent | high-polymerization dimethylpolysiloxane *[4] | 2.0 | 2.0 | 2.0 | 2.0 | 2.0 | 2.0 | 2.0 | 2.0 | 2.0 | 2.0 | 2.0 | | 2.0 |
| | | PPG-3 capryl ether | | | | | | | | | | | | 1.0 | |
| | Others | pearly agent*[5] | | | | | | | adequate dose | | | | | | |
| | | pH regulator | | | | | | | adequate dose | | | | | | |
| | | pure water | | | | | | | balance | | | | | | |
| | Finger-Combability in rinsing | | 4.0 | 4.4 | 4.2 | 4.4 | 5.0 | 4.2 | 4.0 | 4.2 | 4.6 | 4.2 | 4.4 | 4.6 | 3.0 |
| | Smoothness in rinsing | | 4.2 | 3.8 | 4.4 | 4.6 | 4.2 | 4.8 | 4.4 | 4.2 | 4.8 | 4.4 | 4.2 | 4.6 | 3.0 |
| | Long-lasting smoothness in rinsing | | 4.0 | 4.0 | 4.4 | 5.0 | 4.2 | 5.0 | 4.0 | 4.2 | 5.0 | 4.4 | 4.0 | 4.8 | 3.0 |
| | Moist Feeling after drying | | 3.4 | 4.4 | 4.4 | 5.0 | 4.2 | 4.0 | 3.8 | 4.0 | 4.6 | 4.2 | 4.6 | 4.6 | 3.0 |
| | Uniformity after drying | | 4.0 | 4.2 | 3.8 | 4.2 | 3.8 | 4.0 | 3.8 | 4.4 | 4.6 | 4.0 | 4.0 | 4.4 | 3.0 |

The details of the components used in Table 4 are shown below.

*[1] Kao's "Emal 170J" (active ingredient 70%)
*[2] Kao's "Amphitol 55AB" (active ingredient 30%)
*[3] Kawaken Fine Chemical's "Amizol CME"
*[4] Toray Dow Corning's "BY22-029" (active ingredient 50%)
*[5] Kao's "Pearl Concentrate SA-M2" (active ingredient 20%)

From Table 4, it is known that the hair shampoos of Examples 18 to 29 are excellent in the finger-combability in hair washing, the smoothness property and the long-lasting smoothness in rinsing, and the moist feeling and the uniformity after drying.

Example 30 (Body Shampoo)

A body shampoo having the composition mentioned below was produced according to an ordinary method, and evaluated in the same manner as in Example 15. As a result, the skin washed with the body shampoo and dried had an excellent moist feeling.

| (Components) | (%) |
|---|---|
| Sodium polyoxyethylene alkyl ether sulfate *1 | 6.2 |
| Sodium cocoyl isethionate *2 | 5.8 |
| Coconut oil fatty acid amide propylbetaine *3 | 3.7 |
| Glycerin | 3.2 |
| Lauric acid | 4.0 |
| Myristic acid | 0.5 |
| Palmitic acid | 1.5 |
| Stearic acid | 1.5 |
| Sunflower oil | 13.2 |
| CCE (8) | 0.2 |
| Potassium hydroxide | adequate dose *4 |
| Fragrance, Preservative | adequate dose |
| Pure water | balance |
| Total | 100.0 |

*1: Kao's "Emal 270J" (active ingredient 70%) (In the above composition, the content is in terms of sodium polyoxyethylene alkyl ether sulfate.)
*2: NOF's "Diapon CI" (active ingredient 100%)
*3: Kao's "Amphitol 55AB" (active ingredient 30%) (In the above composition, the content is in terms of coconut oil fatty acid amide propylbetaine.)
*4: The pH of the body shampoo was controlled to be 7.3.

Example 31 (Face Wash)

A face wash having the composition mentioned below was produced, and evaluated in the same manner as in Example 15. As a result, the skin washed with the face wash and dried had an excellent moisturizing feeling.

| (Components) | (%) |
|---|---|
| Sodium cocoylglycinate *1 | 9.4 |
| Sodium cocoamphoacetate *2 | 2.5 |
| Coconut oil fatty acid amide propylbetaine *3 | 1.7 |
| Lauric acid | 2.0 |
| Glycerin | 6.0 |
| Vaseline | 9.0 |
| CCE (8) | 0.3 |
| Fragrance, Preservative | adequate dose |
| pH regulator | adequate dose *4 |
| Pure water | balance |
| Total | 100.0 |

*1: Ajinomoto's "AMILITE GCS-11" (active ingredient 100%)
*2: Nikko Chemical's "NIKKOL AM-101" (active ingredient 40%) (In the above composition, the content is in terms of sodium cocoamphoacetate.)
*3: Kao's "Amphitol 55AB" (active ingredient 30%) (In the above composition, the content is in terms of coconut oil fatty acid amide propylbetaine.)
*4: The pH of the face wash was controlled to be 9.0, using citric acid and sodium hydroxide.

Example 32 (Face Wash)

A face wash having the composition mentioned below was produced and evaluated in the same manner as in Example 15. As a result, the skin washed with the face wash and dried had an excellent moisturizing feeling.

| (Components) | (%) |
|---|---|
| Sodium cocoylmethyltaurate *1 | 1.4 |
| Lauric acid | 28.2 |
| Myristic acid | 2.8 |
| Palmitic acid | 3.1 |
| PEG-32 *2 | 2.0 |
| Glycerin | 16.0 |
| Vaseline | 5.0 |
| CCE (8) | 0.3 |
| Fragrance, Preservative | adequate dose |
| pH regulator | adequate dose *3 |
| Pure water | balance |
| Total | 100.0 |

*1: Nikko Chemical's "NIKKOL CMT-30" (active ingredient 30%) (In the above composition, the content is in terms of sodium cocoylmethyltaurate.)
*2: NOF's "PEG#1500"
*3: The pH of the face wash was controlled to be 9.0, using citric acid and sodium hydroxide.

Examples 33 to 50 (Production and Evaluation of Oil Hair Shampoo Additionally Containing any Other Cationized Polymer than CCE), Comparative Example 7)

Using any of CCE (2) to (4), (8) to (13), and (17) to (19), a hair shampoo was prepared to have the composition shown in Table 5, according to an ordinary method (Examples 33 to 50). In addition, a comparative hair shampoo not containing CCE was prepared to have the composition shown in Table 5, according to an ordinary method (Comparative Example 7).

Concretely, CCE and the other cationic polymer than CCE were dissolved or uniformly dispersed in water, adequate amounts of water and surfactant were taken in a beaker, and uniformly mixed under heat at 60° C., and then cooled down to 50° C. Finally, water that had been evaporated away by heating was replenished, and the pH of the composition was measured. Using a pH regulator (aqueous 50% citric acid solution), the pH was controlled to be 5.

Hair tresses (20 g, 20 cm) were washed with the plain shampoo described in Example 1, then fully wetted with warm water at 35 to 40° C., 0.5 g of the shampoo of Examples 33 to 50 was applied thereto, and the hair tresses were thus shampooed therewith for 1 minute. Subsequently, the hair tresses were rinsed with warm water for 30 seconds, water was wiped away with a towel, the hair tresses were then combed and dried with warm air from a hair drier, and combed for final finish.

Five panelists evaluated the hair tresses in point of the foam softness, the finger-comability and the hair softness in hair washing, the smoothness, the softness, the long-lasting smoothness and the coated feeling in rinsing, according to the evaluation criteria and the evaluation methods mentioned below. The evaluation results are shown in Table 5.
(Evaluation Criteria, Evaluation Methods)
Foam Softness in Washing 5: Extremely soft as compared with the hair shampoo of Comparative Example 7.

4: Soft as compared with the hair shampoo of Comparative Example 7.

3: Average (foam softness in washing with the hair shampoo of Comparative Example 7).

2: Hard as compared with the hair shampoo of Comparative Example 7.

1: Extremely hard as compared with the hair shampoo of Comparative Example 7.

Finger-Combability in Washing
   5: Extremely good finger-Combability as compared with the hair shampoo of Comparative Example 7.
   4: Good finger-Combability as compared with the hair shampoo of Comparative Example 7.
   3: Average (finger-Combability in washing with the hair shampoo of Comparative Example 7).
   2: Bad finger-Combability as compared with the hair shampoo of Comparative Example 7.
   1: Extremely bad finger-Combability as compared with the hair shampoo of Comparative Example 7.
Hair Softness in Washing
   5: Extremely soft as compared with the hair shampoo of Comparative Example 7.
   4: Soft as compared with the hair shampoo of Comparative Example 7.
   3: Average (hair softness in washing with the hair shampoo of Comparative Example 7).
   2: Hard as compared with the hair shampoo of Comparative Example 7.
   1: Extremely hard as compared with the hair shampoo of Comparative Example 7.
Smoothness in Rinsing
   5: Extremely good smoothness as compared with the hair shampoo of Comparative Example 7.
   4: Good smoothness as compared with the hair shampoo of Comparative Example 7.
   3: Average (smoothness in rinsing with the hair shampoo of Comparative Example 7).
   2: Bad smoothness as compared with the hair shampoo of Comparative Example 7.
   1: Extremely bad smoothness as compared with the hair shampoo of Comparative Example 7.

Hair Softness in Rinsing
   5: Extremely soft as compared with the hair shampoo of Comparative Example 7.
   4: Soft as compared with the hair shampoo of Comparative Example 7.
   3: Average (hair softness in rinsing with the hair shampoo of Comparative Example 7)
   2: Hard as compared with the hair shampoo of Comparative Example 7.
   1: Extremely hard as compared with the hair shampoo of Comparative Example 7.
Long-Lasting Smoothness:
   5: Extremely good long-lasting smoothness as compared with the hair shampoo of Comparative Example 7.
   4: Good long-lasting smoothness as compared with the hair shampoo of Comparative Example 7.
   3: Average (long-lasting smoothness in rinsing with the hair shampoo of Comparative Example 7).
   2: Bad long-lasting smoothness as compared with the hair shampoo of Comparative Example 7.
   1: Extremely bad long-lasting smoothness as compared with the hair shampoo of Comparative Example 7.
Coated Feeling in Rinsing
   5: Extremely good coated feeling as compared with the hair shampoo of Comparative Example 7.
   4: Good coated feeling as compared with the hair shampoo of Comparative Example 7.
   3: Average (coated feeling in rinsing with the hair shampoo of Comparative Example 7).
   2: Bad coated feeling as compared with the hair shampoo of Comparative Example 7.
   1: Extremely bad coated feeling as compared with the hair shampoo of Comparative Example 7.

TABLE 5

| Hair Wash Composition (hair shampoo) | | | Example | | | | | | | | | |
|---|---|---|---|---|---|---|---|---|---|---|---|---|
| | | | 33 | 34 | 35 | 36 | 37 | 38 | 39 | 40 | 41 | 42 |
| Composition (mass %) | CCE | CCE(2) | 0.3 | | | | | | | | | |
| | | CCE(3) | | 0.3 | | | | | | | | |
| | | CCE(4) | | | 0.3 | | | | | | | |
| | | CCE(8) | | | | 0.3 | | | | | | |
| | | CCE(9) | | | | | 0.3 | | | | | |
| | | CCE(10) | | | | | | 0.3 | | | | |
| | | CCE(11) | | | | | | | 0.3 | | | |
| | | CCE(12) | | | | | | | | 0.3 | | |
| | | CCE(13) | | | | | | | | | 0.3 | |
| | | CCE(17) | | | | | | | | | | 0.3 |
| | | CCE(18) | | | | | | | | | | |
| | | CCE(19) | | | | | | | | | | |
| | Cationic Polymer | Guar hydroxypropyltrimonium chloride*1 | 0.1 | 0.1 | 0.1 | 0.1 | 0.1 | 0.1 | 0.1 | 0.1 | 0.1 | 0.1 |
| | | Polyquaternium-10*2 | | | | | | | | | | |
| | | C-HPC*3 | | | | | | | | | | |
| | | Polyquaternium-70*4 | | | | | | | | | | |
| | | Cassia hydroxypropyltrimonium chloride*5 | | | | | | | | | | |
| | | Locust bean hydroxypropyltrimonium chloride *6 | | | | | | | | | | |
| | | Polyquaternium-7*7 | | | | | | | | | | |
| | Surfactant | Sodium laureth(1) sulfate*8 | 13.0 | 13.0 | 13.0 | 13.0 | 13.0 | 13.0 | 13.0 | 13.0 | 13.0 | 13.0 |
| | | Coconut oil fatty acid amide propylbetaine*9 | 1.5 | 1.5 | 1.5 | 1.5 | 1.5 | 1.5 | 1.5 | 1.5 | 1.5 | 1.5 |

TABLE 5-continued

|  |  |  |  |  |  |  |  |  |  |  |  |
|---|---|---|---|---|---|---|---|---|---|---|---|
|  |  | Coconut oil fatty acid monoethanolamide*10 | 0.3 | 0.3 | 0.3 | 0.3 | 0.3 | 0.3 | 0.3 | 0.3 | 0.3 | 0.3 |
|  | Oil Agent | High-polymerized dimethylpolysiloxane *11 | 2.0 | 2.0 | 2.0 | 2.0 | 2.0 | 2.0 | 2.0 | 2.0 | 2.0 | 2.0 |
|  | Others | Pearl agent*12 |  |  |  |  | adequate dose |  |  |  |  |  |
|  |  | pH regulator |  |  |  |  | adequate dose |  |  |  |  |  |
|  |  | Pure water |  |  |  |  | balance |  |  |  |  |  |
| Evaluation Results |  | Foam softness in washing | 4.8 | 4.0 | 4.0 | 4.8 | 4.4 | 4.6 | 4.6 | 4.4 | 4.6 | 3.8 |
|  |  | Finger-combability in washing | 4.8 | 4.4 | 4.0 | 4.6 | 5.0 | 4.6 | 4.6 | 4.6 | 4.4 | 4.4 |
|  |  | Hair softness in washing | 4.6 | 4.6 | 4.0 | 5.0 | 4.6 | 4:2 | 5.0 | 4.2 | 4.4 | 4.2 |
|  |  | Smoothness in rinsing | 4.8 | 4.2 | 4.4 | 4.6 | 5.0 | 4.8 | 4.8 | 4.4 | 4.4 | 4.2 |
|  |  | Hair softness in rinsing | 4.8 | 4.4 | 4.6 | 5.0 | 4.8 | 4.4 | 5.0 | 4.4 | 4.4 | 4.2 |
|  |  | Long-lasting smoothness | 4.8 | 4.4 | 4.4 | 5.0 | 4.8 | 4.6 | 5.0 | 4.4 | 4.4 | 4.4 |
|  |  | Coated feeling in rinsing | 4.8 | 4.6 | 4.6 | 5.0 | 4.8 | 4.4 | 5.0 | 4.4 | 4.4 | 4.4 |

| Hair Wash Composition |  |  | Example |  |  |  |  |  |  |  | Comparative Example |
|---|---|---|---|---|---|---|---|---|---|---|---|
| (hair shampoo) |  |  | 43 | 44 | 45 | 46 | 47 | 48 | 49 | 50 | 7 |
| Composition (mass %) | CCE | CCE(2) |  |  |  |  |  |  |  |  |  |
|  |  | CCE(3) |  |  |  |  |  |  |  |  |  |
|  |  | CCE(4) |  |  |  |  |  |  |  |  |  |
|  |  | CCE(8) |  |  | 0.3 | 0.3 | 0.3 | 0.3 | 0.3 |  |  |
|  |  | CCE(9) |  |  |  |  |  |  |  |  |  |
|  |  | CCE(10) |  |  |  |  |  |  |  |  |  |
|  |  | CCE(11) |  |  |  |  |  |  |  |  |  |
|  |  | CCE(12) |  |  |  |  |  |  |  |  |  |
|  |  | CCE(13) |  |  |  |  |  |  |  |  |  |
|  |  | CCE(17) |  |  |  |  |  |  |  |  |  |
|  |  | CCE(18) | 0.3 |  |  |  |  |  |  |  |  |
|  |  | CCE(19) |  | 0.3 |  |  |  |  |  |  |  |
|  | Cationic Polymer | Guar hydroxypropyltrimonium chloride*1 | 0.1 | 0.1 |  |  |  |  |  |  | 0.4 |
|  |  | Polyquaternium-10*2 |  |  | 0.1 |  |  |  |  |  |  |
|  |  | C-HPC*3 |  |  |  | 0.1 |  |  |  |  |  |
|  |  | Polyquaternium-70*4 |  |  |  |  | 0.1 |  |  |  |  |
|  |  | Cassia hydroxypropyltrimonium chloride*5 |  |  |  |  |  | 0.1 |  |  |  |
|  |  | Locust bean hydroxypropyltrimonium chloride *6 |  |  |  |  |  |  | 0.1 |  |  |
|  |  | Polyquaternium-7*7 |  |  |  |  |  |  |  | 0.1 |  |
|  | Surfactant | Sodium laureth(1) sulfate*8 | 13.0 | 13.0 | 13.0 | 13.0 | 13.0 | 13.0 | 13.0 | 13.0 | 13.0 |
|  |  | Coconut oil fatty acid amide propylbetaine*9 | 1.5 | 1.5 | 1.5 | 1.5 | 1.5 | 1.5 | 1.5 | 1.5 | 1.5 |
|  |  | Coconut oil fatty acid monoethanolamide*10 | 0.3 | 0.3 | 0.3 | 0.3 | 0.3 | 0.3 | 0.3 | 0.3 | 0.3 |
|  | Oil Agent | High-polymerized dimethylpolysiloxane *11 | 2.0 | 2.0 | 2.0 | 2.0 | 2.0 | 2.0 | 2.0 | 2.0 | 2.0 |
|  | Others | Pearl agent*12 |  |  |  |  | adequate dose |  |  |  |  |
|  |  | pH regulator |  |  |  |  | adequate dose |  |  |  |  |
|  |  | Pure water |  |  |  |  | balance |  |  |  |  |
| Evaluation Results |  | Foam softness in washing | 4.8 | 4.4 | 4.0 | 4.2 | 4.0 | 4.0 | 4.6 | 5.0 | 3.0 |
|  |  | Finger-combability in washing | 4.6 | 4.4 | 4.4 | 4.4 | 4.4 | 4.2 | 4.8 | 4.0 | 3.0 |
|  |  | Hair softness in washing | 4.2 | 4.4 | 4.4 | 4.6 | 4.4 | 4.8 | 5.0 | 4.0 | 3.0 |
|  |  | Smoothness in rinsing | 4.4 | 4.8 | 4.2 | 4.2 | 4.4 | 4.2 | 4.2 | 4.2 | 3.0 |
|  |  | Hair softness in rinsing | 4.0 | 4.4 | 4.6 | 4.8 | 4.8 | 4.2 | 5.0 | 4.0 | 3.0 |
|  |  | Long-lasting smoothness | 4.4 | 4.8 | 4.6 | 4.4 | 4.8 | 4.4 | 5.0 | 4.4 | 3.0 |
|  |  | Coated feeling in rinsing | 4.2 | 4.4 | 4.4 | 4.8 | 4.8 | 5.0 | 5.0 | 4.4 | 3.0 |

The details of the components used in Table 5 are shown below.
*1Rhodia's "Jaguar C-13S"
*2Dow Chemical's "UCARE LR30M"
*3Production Example 25
*4Dow Chemicals "SOFTCAT SL-100"
*5Lubrizol's "Sensomer CT400 Polymer"

TABLE 5-continued

*6 Toho Chemical's "Catinal CLB100"
*7 Lubrizol's "Merquat 550"
*8 Kao's "Emal 170J" (active ingredient 70%)
*9 Kao's "Amphitol 55AB" (active ingredient 30%)
*10 Kawaken Fine Chemical's "Amizole CME"
*11 Toray Dow Corning's "BY22-029" (active ingredient 50%)
*12 Kao's "Pearl Concentrate SA-M2" (active ingredient 20%)

From Table 5, it is known that the hair shampoos of Examples 33 to 50 are excellent in the foam softness, the finger-combability and the hair softness in washing, and in the smoothness, the softness, the long-lasting smoothness and the coated feeling in rinsing.

Example 51 (Hair Shampoo)

A composition comprising the components mentioned below was produced in the same manner as in Example 1. Artificial hair tresses (20 g, 20 cm) were washed with the plain shampoo described in Example 1, then well wetted with warm water at 35 to 40° C., 0.5 g of the hair shampoo was applied thereto and the hair was washed for 1 minute. Subsequently, the hair was rinsed with warm water for 30 seconds, wiped with a towel and combed, and further dried with warm air from a drier. Finally, the hair was combed. The hair thus washed with the hair shampoo

| (Components) | (%) |
| --- | --- |
| Sodium laureth-1 sulfate *1 | 13.0 |
| Coconut oil fatty acid amide propylbetaine *2 | 2.0 |
| Coconut oil fatty acid monoethanolamide *3 | 1.0 |
| CCE (20) | 0.3 |
| Cationized hydroxyethyl cellulose *4 | 0.1 |
| Dimethyldiallylammonium chloride-acrylamide copolymer *5 | 0.1 |
| High-polymerized dimethylpolysiloxane *6 | 2.0 |
| Amino-modified high-polymerized dimethylpolysiloxane *7 | 1.0 |
| PPG-3 caprylyl ether *8 | 0.5 |
| Pearl agent *9 | 1.0 |
| Fragrance, Preservative | adequate dose |
| Pure water | balance |
| Total | 100.0 |

*1: Kao's "Emal 170J" (active ingredient 70%)
*2: Kao's "Amphitol 55AB" (active ingredient 30%)
*3: Kao's "Aminone C-11S"
*4: Kao's "POIZ C-80M"
*5: Lubrizol's "Merquat 550" (active ingredient 9%)
*6: Toray Dow Corning's "BY22-029" (active ingredient 50%)
*7: Toray Dow Corning's "SM8904" (active ingredient 40%)
*8: Kao's "Kao Sofcare GP-1"
*9: Kao's "Pearl Concentrate SA-M2"

Example 52 (Hair Shampoo)

A hair shampoo having the composition mentioned below was produced in the same manner as in Example 1. This was evaluated according to the same method as in Example 18, and as a result, the hair washed with the hair shampoo and dried had an excellent moist feeling.

| (Components) | (%) |
| --- | --- |
| Sodium laureth-1 sulfate *1 | 13.0 |
| Coconut oil fatty acid amide propylbetaine *2 | 1.5 |
| Coconut oil fatty acid monoethanolamide *3 | 1.0 |
| CCE (20) | 0.3 |
| C-HPC | 0.1 |
| High-polymerized dimethylpolysiloxane *4 | 2.0 |
| PPG-3 caprylyl ether *5 | 1.0 |
| Pearl agent *6 | 1.0 |
| Fragrance, Preservative | adequate dose |
| Pure water | balance |
| Total | 100.0 |

*1: Kao's "Emal 170J" (active ingredient 70%)
*2: Kao's "Amphitol 55AB" (active ingredient 30%)
*3: Kao's "Aminone C-11S"
*4: Toray Dow Corning's "BY22-029" (active ingredient 50%)
*5: Kao's "Kao Sofcare GP-1"
*6: Kao's "Pearl Concentrate SA-M2"

Example 53 (Body Shampoo)

A body shampoo having the composition mentioned below was produced according to an ordinary method, and evaluated in the same manner as in Example 15. As a result, the skin washed with the body shampoo and dried had an excellent moist feeling.

| (Components) | (%) |
| --- | --- |
| Lauric acid | 8.6 |
| Myristic acid | 8.4 |
| Palmitic acid | 2.5 |
| Sodium polyoxyethylene alkyl ether sulfate *1 | 2.9 |
| Glycerin | 1.9 |
| Propylene glycol | 1.2 |
| Coconut oil fatty acid amide propylbetaine *2 | 0.9 |
| CCE (4) | 0.2 |
| Cationized guar gum *3 | 0.1 |
| Potassium hydroxide (to make pH 9.6) | adequate dose |
| Fragrance, Preservative | adequate dose |
| Pure water | balance |
| Total | 100.0 |

*1: Kao's "Emal 270J" (active ingredient 70%) (In the above composition, the content is in terms of sodium polyoxyethylene alkyl ether sulfate.)
*2: Kao's "Amphitol 55AB" (active ingredient 30%) (In the above composition, the content is in terms of coconut oil fatty acid amide propylbetaine.)
*3: Rhodia's "Jaguar C-13S" (active ingredient 100%)

Example 54 (Body Shampoo)

A body shampoo having the composition mentioned below was produced according to an ordinary method, and evaluated in the same manner as in Example 15. As a result, the skin washed with the body shampoo and dried had an excellent moist feeling.

| (Components) | (%) |
| --- | --- |
| Sodium polyoxyethylene alkyl ether sulfate *1 | 10.0 |
| Coconut oil fatty acid amide propylbetaine *2 | 1.5 |

-continued

| (Components) | (%) |
| --- | --- |
| Coconut oil fatty acid monoethanolamide | 1.0 |
| Glycerin | 2.0 |
| Sodium chloride | 1.0 |
| CCE (4) | 0.2 |
| Polyquaternium-10 *3 | 0.1 |
| Fragrance, Preservative | adequate dose |
| Pure water | balance |
| Total | 100.0 |

*1: Kao's "Emal 270J" (active ingredient 70%) (In the above composition, the content is in terms of sodium polyoxyethylene alkyl ether sulfate.)
*2: Kao's "Amphitol 55AB" (active ingredient 30%) (In the above composition, the content is in terms of coconut oil fatty acid amide propylbetaine.)
*3: Kao's "POIZ C-80M" (active ingredient 100%)

Example 55 (Body Shampoo)

A body shampoo having the composition mentioned below was produced according to an ordinary method, and evaluated in the same manner as in Example 15. As a result, the skin washed with the body shampoo and dried had an excellent moist feeling.

| (Components) | (%) |
| --- | --- |
| Potassium lauroylsarcosinate *1 | 6.0 |
| Sodium polyoxyethylene alkyl ether sulfate *2 | 3.3 |
| Propylene glycol | 3.2 |
| Coconut oil fatty acid amide propylbetaine *3 | 2.8 |
| Glycol distearate | 1.0 |
| Coconut oil fatty acid diethanolamide | 0.7 |
| CCE (4) | 0.2 |
| Polyquaternium-10 *4 | 0.1 |
| Fragrance, Preservative | adequate dose |
| pH regulator | adequate dose *5 |
| Pure water | balance |
| Total | 100.0 |

*1: Nikko Chemical's "NIKKOL SARCOSINATE LK-30" (active ingredient 30%) (In the above composition, the content is in terms of potassium lauroylsarcosinate.)
*2: Kao's "Emal 270J" (active ingredient 70%) (In the above composition, the content is in terms of sodium polyoxyethylene alkyl ether sulfate.)
*3: Kao's "Amphitol 55AB" (active ingredient 30%) (In the above composition, the content is in terms of coconut oil fatty acid amide propylbetaine.)
*4: Kao's "POIZ C-80M" (active ingredient 100%)
*5: The pH of the body shampoo was controlled to be 6.0, using citric acid and sodium hydroxide.

Example 56 (Face Wash)

A face wash having the composition mentioned below was produced and evaluated in the same manner as in Example 15. As a result, the skin washed with the body shampoo and dried had an excellent moist feeling.

| (Components) | (%) |
| --- | --- |
| Na cocoylmethyltaurate *1 | 1.4 |
| Lauric acid | 28.2 |
| Myristic acid | 2.8 |
| Palmitic acid | 3.1 |
| PEG-32 *2 | 2.0 |
| Glycerin | 16.0 |
| CCE (4) | 0.2 |
| Polyquaternium-10 *3 | 0.1 |
| Fragrance, Preservative | adequate dose |
| pH regulator | adequate dose *4 |
| Pure water | balance |
| Total | 100.0 |

*1: Nikko Chemical's "NIKKOL CMT-30" (active ingredient 30%) (In the above composition, the content is in terms of sodium cocoylmethyltaurate.)
*2: NOF's "PEG#1500" (active ingredient 100%)
*3: Kao's "POIZ C-80M" (active ingredient 100%)
*4: The pH of the face wash was controlled to be 9.0, using citric acid and sodium hydroxide.

Examples 57 to 71 (Production and Evaluation of Hair Conditioner Composition), Comparative Example 8)

Using any of CCE (2) to (4), (8) to (19) and CPGC (2), a hair conditioner composition (conditioner) having the composition shown in Table 6 was prepared according to an ordinary method.

Concretely, CCE or CPGC, an adequate amount of water and an adequate amount of a pH regulator (aqueous 50% citric acid solution) were taken in a beaker, and dissolved under heat at 80° C. A surfactant that had been melted at 80° C. was added thereto and emulsified with stirring for 1 hour. This was cooled down to 50° C., and an oily agent was added thereto and uniformly mixed. Finally, water that had been evaporated away by heating was replenished, and the pH of the composition was measured. If desired, the pH of the composition was controlled to be 5, using a pH regulator (aqueous 50% citric acid solution and aqueous 48% sodium hydroxide solution).

Artificial hair tresses (20 g, 20 cm) that had been washed with the plain shampoo described in Example 1 were well wetted with warm water at 35 to 40° C., 1 g of the conditioner of Examples 57 to 71 and Comparative Example 8 was applied thereto and left as such for 1 minute, then rinsed with warm water for 30 seconds, toweled to remove water, and then combed. Subsequently, the hair was dried with warm air from a drier, and finally combed.

Five panelists evaluated the hair in point of the presence in application of the conditioner to the hair, and in point of the softness and the long-lasting smoothness in rinsing, and the coated feeling in drying. The results are shown in Table 6.

(Evaluation Criteria, Evaluation Methods)
Presence in Application
  5: Excellent presence as compared with the conditioner of Comparative Example 8.
  4: Good presence as compared with the conditioner of Comparative Example 8.
  3: Average (presence in application of the conditioner of Comparative Example 8).
  2: Poor presence as compared with the conditioner of Comparative Example 8.
  1: No presence.
Softness in Rinsing
  5: Extremely soft as compared with the conditioner of Comparative Example 8.
  4: Soft as compared with the conditioner of Comparative Example 8.

3: Average (softness in rinsing with the conditioner of Comparative Example 8).

2: Hard as compared with the conditioner of Comparative Example 8.

1: Extremely hard as compared with the conditioner of Comparative Example 8.

Long-Lasting Smoothness:

5: Extremely good long-lasting smoothness as compared with the conditioner of Comparative Example 8.

4: Good long-lasting smoothness as compared with the conditioner of Comparative Example 8.

3: Average (long-lasting smoothness in rinsing with the conditioner of Comparative Example 8).

2: Bad long-lasting smoothness as compared with the conditioner of Comparative Example 8.

1: Extremely bad long-lasting smoothness as compared with the conditioner of Comparative Example 8.

Coated Feeling after Drying

5: Extremely good coated feeling as compared with the conditioner of Comparative Example 8.

4: Good coated feeling as compared with the conditioner of Comparative Example 8.

3: Average (coated feeling after drying with the conditioner of Comparative Example 8).

2: Bad coated feeling as compared with the conditioner of Comparative Example 8.

1: No coated feeling.

From Table 6, it is known that the hair conditioner compositions of Examples 57 to 71 are excellent in presence in application, the softness and the long-lasting smoothness in rinsing, and the coated feeling after drying.

Example 72 (Leave-in Hair Conditioner)

In the same manner as in Example 57, a leave-in hair conditioner having the composition mentioned below was prepared.

| (Components) | (%) |
|---|---|
| CCE (20) | 0.05 |
| Stearyl alcohol | 0.4 |
| High-polymerized dimethylsiloxane *1 | 0.1 |
| Behenyltrimethylammonium chloride | 0.2 |
| Citric acid | adequate dose *2 |
| Pure water | balance |
| Total | 100.0 |

*1: Toray Dow Corning's "BY22-060" (active ingredient 60%) (In the above composition, the content is in terms of high-polymerized dimethylsiloxane.)
*2: The pH of the hair conditioner was controlled to be 5.0.

Artificial hair tresses (20 g, 20 cm) that had been washed with the plain shampoo described in Example 1 were well wetted with warm water at 35 to 40° C., water was removed from the hair tresses, which were then dried with warm air from a drier, and then combed. One g of the hair conditioner

TABLE 6

| | | | Example | | | | | | | | | | | | | Comparative Example |
|---|---|---|---|---|---|---|---|---|---|---|---|---|---|---|---|---|
| Hair Conditioner Composition | | | 57 | 58 | 59 | 60 | 61 | 62 | 63 | 64 | 65 | 66 | 67 | 68 | 69 | 70 | 71 | 8 |
| Composition (mass %) | Polymer | CCE(2) | 0.3 | | | | | | | | | | | | | | | | |
| | | CCE(3) | | 0.3 | | | | | | | | | | | | | | |
| | | CCE(4) | | | 0.3 | | | | | | | | | | | | | |
| | | CCE(8) | | | | 0.3 | | | | | | | | | | | | |
| | | CCE(9) | | | | | 0.3 | | | | | | | | | | | |
| | | CCE(10) | | | | | | 0.3 | | | | | | | | | | |
| | | CCE(11) | | | | | | | 0.3 | | | | | | | | | |
| | | CCE(12) | | | | | | | | 0.3 | | | | | | | | |
| | | CCE(13) | | | | | | | | | 0.3 | | | | | | | |
| | | CCE(14) | | | | | | | | | | 0.3 | | | | | | |
| | | CCE(15) | | | | | | | | | | | 0.3 | | | | | |
| | | CCE(16) | | | | | | | | | | | | 0.3 | | | | |
| | | CCE(17) | | | | | | | | | | | | | 0.3 | | | |
| | | CCE(18) | | | | | | | | | | | | | | 0.3 | | |
| | | CCE(19) | | | | | | | | | | | | | | | 0.3 | |
| | | CPGC(2) | | | | | | | | | | | | | | | | 0.3 |
| | Surfactant | Behenyltrimethylammonium chloride*1 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 |
| | Oily Agent | Cetyl alcohol*2 | 1.3 | 1.3 | 1.3 | 1.3 | 1.3 | 1.3 | 1.3 | 1.3 | 1.3 | 1.3 | 1.3 | 1.3 | 1.3 | 1.3 | 1.3 | 1.3 |
| | | Stearyl alcohol*3 | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 |
| | | High-polymerized dimethylpolysiloxane*4 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 |
| | Others | pH regulator | | | | | | adequate dose | | | | | | | | | | |
| | | Solvent | | | | | | adequate dose | | | | | | | | | | |
| | | Pure water | | | | | | balance | | | | | | | | | | |
| Evaluation Results | | Presence in application | 4.4 | 4.0 | 4.0 | 5.0 | 4.6 | 3.8 | 5.0 | 4.4 | 3.8 | 4.2 | 3.8 | 3.8 | 4.2 | 4.4 | 3.8 | 3.0 |
| | | Softness in rinsing | 4.6 | 4.0 | 4.4 | 5.0 | 4.8 | 4.4 | 5.0 | 4.8 | 5.0 | 4.0 | 4.2 | 4.2 | 4.4 | 4.8 | 4.6 | 3.0 |
| | | long-lasting smoothness | 4.6 | 4.2 | 4.6 | 4.6 | 4.6 | 4.2 | 4.4 | 4.2 | 5.0 | 4.0 | 4.4 | 4.4 | 4.2 | 4.8 | 4.0 | 3.0 |
| | | Coated feeling after drying | 4.0 | 4.0 | 4.0 | 5.0 | 4.4 | 4.8 | 5.0 | 5.0 | 4.6 | 3.8 | 4.4 | 3.8 | 4.2 | 4.8 | 4.0 | 3.0 |

The details of the components used in Table 6 are shown below.
*1 Kao's "QUARTAMIN 2285E-E"
*2 Kao's "Kalcol 6098"
*3 Kao's "Kalcol 8098"
*4 Toray Dow Corning's "BY22-029" (active ingredient 50%)

was applied to the hair tresses and left as such for 1 minute. After dried at room temperature, the hair tresses were organoleptically evaluated.

As a result, the hair conditioner gave a good coated feeling to the dried hair.

Example 73 (Leave-in Hair Conditioner)

In the same manner as in Example 57, a leave-in hair conditioner having the composition mentioned below was

| (Components) | (%) |
|---|---|
| CCE (20) | 0.5 |
| Stearyl alcohol | 4.0 |
| High-polymerized dimethylsiloxane *1 | 4.0 |
| Cetyltrimethylammonium chloride | 5.0 |
| Citric acid | adequate dose *2 |
| Pure water | balance |
| Total | 100.0 |

*1: Toray Dow Corning's "BY22-060" (active ingredient 60%) (In the above composition, the content is in terms of high-polymerized dimethylsiloxane.)
*2: The pH of the hair conditioner was controlled to be 5.0.

Artificial hair tresses (20 g, 20 cm) that had been washed with the plain shampoo described in Example 1 were well wetted with warm water at 35 to 40° C., water was removed from the hair tresses, which were then dried with warm air from a drier, and then combed. 0.1 g of the hair conditioner was applied to the hair tips and left as such for 1 minute. After dried at room temperature, the hair tresses were organoleptically evaluated.

The hair conditioner gave a good coated feeling to the dried hair.

Examples 74 to 84 (Production and Evaluation of Two-Pack Hair Bleach Composition), Comparative Example 9)

(1) Preparation of First Pack

The other components than the oil agent (higher alcohol), aqueous 28% ammonia solution and propylene glycol shown in Table 7 (first pack) were mixed with an adequate amount of water and stirred. This was heated at 60° C. and completely dissolved. To this was added a mixture prepared by previously mixing cetyl alcohol and propylene glycol and heated at 70° C., and emulsified for 30 minutes. After this was cooled down to 40° C., aqueous 28% ammonia solution and the remaining water were added and uniformly mixed to prepare a first pack.

(2) Preparation of Second Pack

As shown in Table 7 (second pack), the surfactants (ceteareth-13 and sodium laureth-1 sulfate), the other components (EDTA-2-sodium, phosphoric acid, disodium hydrogenphosphate), and an adequate amount of water were mixed with stirring, and completely dissolved by heating up to 60° C. To this was added the oil agent (higher alcohol) that had been heated at 70° C., and emulsified. After this was cooled down to 40° C., aqueous 35% hydrogen peroxide solution and the remaining water were added thereto and uniformly mixed to prepare a second pack. The pH was 4.

(3) Evaluation of Two-Pack Hair Bleach Composition

Hair (artificial black hair, BS-B3A) with no chemical treatment history, which is commercially sold by Beaulax and which has a length of 30 cm and a mass of 10 g, was used. 3 g of the hair sample was dressed in a width of 2 cm so as to have a uniform thickness. One end of the hair was fixed to a plastic plate having a width of 2 cm with an adhesive, thereby preparing a test piece of hair tresses.

The hair tresses were washed with the plain shampoo described in Example 1, and dried with warm air from a drier. The first pack and the second pack obtained in the above (1) and (2) were mixed in a ratio by mass of 2/3, and 3 g of the resulting blend was applied to the hair tresses. Subsequently, the hair tresses were left at 30° C. for 30 minutes.

Five panelists rinsed the evaluation tresses with warm water for 1 minute, and then evaluated for the smoothness feeling, the coat feeling and the softness in rinsing, according to the following evaluation criteria.

The results are shown in Table 7.

The evaluation results of the five panelists were averaged to be a score of the sample.

Smoothness in Rinsing

5: Extremely good Smoothness as compared with the hair bleach of Comparative Example 9.

4: Good Smoothness as compared with the hair bleach of Comparative Example 9.

3: Average (Smoothness in rinsing with the hair bleach of Comparative Example 9).

2: Bad Smoothness as compared with the hair bleach of Comparative Example 9.

1: Extremely bad Smoothness as compared with the hair bleach of Comparative Example 9.

Coated Feeling in Rinsing

5: Extremely good coated feeling as compared with the hair bleach of Comparative Example 9.

4: Good coated feeling as compared with the hair bleach of Comparative Example 9.

3: Average (coated feeling in rinsing with the hair bleach of Comparative Example 9).

2: Bad coated feeling as compared with the hair bleach of Comparative Example 9.

1: No coated feeling at all.

Softness in Rinsing

5: Extremely soft as compared with the hair bleach of Comparative Example 9.

4: Soft as compared with the hair bleach of Comparative Example 9.

3: Average (softness in rinsing with the hair bleach of Comparative Example 9).

2: Poorly soft as compared with the hair bleach of Comparative Example 9.

1: No softness at all.

TABLE 7

| | | | Example | | | | | | | | | | | Comparative Example |
|---|---|---|---|---|---|---|---|---|---|---|---|---|---|---|
| Two-Pack Hair Bleach | | | 74 | 75 | 76 | 77 | 78 | 79 | 80 | 81 | 82 | 83 | 84 | 9 |
| First Pack (mass %) | Polymer | CCE(2) | 0.1 | | | | | | | | | | | |
| | | CCE(3) | | 0.1 | | | | | | | | | | |
| | | CCE(4) | | | 0.1 | | | | | | | | | |
| | | CCE(8) | | | | 0.1 | | | | | | | | |

TABLE 7-continued

|  |  |  | Example | | | | | | | | | | | Comparative Example |
|---|---|---|---|---|---|---|---|---|---|---|---|---|---|---|
| Two-Pack Hair Bleach | | | 74 | 75 | 76 | 77 | 78 | 79 | 80 | 81 | 82 | 83 | 84 | 9 |
|  |  | CCE(9) |  |  |  |  | 0.1 |  |  |  |  |  |  |  |
|  |  | CCE(10) |  |  |  |  |  | 0.1 |  |  |  |  |  |  |
|  |  | CCE(11) |  |  |  |  |  |  | 0.1 |  |  |  |  |  |
|  |  | CCE(13) |  |  |  |  |  |  |  | 0.1 |  |  |  |  |
|  |  | CCE(15) |  |  |  |  |  |  |  |  | 0.1 |  |  |  |
|  |  | CCE(16) |  |  |  |  |  |  |  |  |  | 0.1 |  |  |
|  |  | CCE(19) |  |  |  |  |  |  |  |  |  |  | 0.1 |  |
|  |  | CPGC(2) |  |  |  |  |  |  |  |  |  |  |  | 0.1 |
|  | Treatment agent | Aqueous 28% ammonia | 6.5 | 6.5 | 6.5 | 6.5 | 6.5 | 6.5 | 6.5 | 6.5 | 6.5 | 6.5 | 6.5 | 6.5 |
|  |  | Monoethanolamine | 0.5 | 0.5 | 0.5 | 0.5 | 0.5 | 0.5 | 0.5 | 0.5 | 0.5 | 0.5 | 0.5 | 0.5 |
|  | Surfactant | Ceteareth-13*[1] | 1.0 | 1.0 | 1.0 | 1.0 | 1.0 | 1.0 | 1.0 | 1.0 | 1.0 | 1.0 | 1.0 | 1.0 |
|  |  | Sodium laureth-1 sulfate*[2] | 2.0 | 2.0 | 2.0 | 2.0 | 2.0 | 2.0 | 2.0 | 2.0 | 2.0 | 2.0 | 2.0 | 2.0 |
|  | Oily Agent | Cetyl alcohol | 5.0 | 5.0 | 5.0 | 5.0 | 5.0 | 5.0 | 5.0 | 5.0 | 5.0 | 5.0 | 5.0 | 5.0 |
|  | Others | Propylene glycol | 4.0 | 4.0 | 4.0 | 4.0 | 4.0 | 4.0 | 4.0 | 4.0 | 4.0 | 4.0 | 4.0 | 4.0 |
|  |  | Sodium sulfite | 0.3 | 0.3 | 0.3 | 0.3 | 0.3 | 0.3 | 0.3 | 0.3 | 0.3 | 0.3 | 0.3 | 0.3 |
|  |  | Sodium ascorbate | 0.3 | 0.3 | 0.3 | 0.3 | 0.3 | 0.3 | 0.3 | 0.3 | 0.3 | 0.3 | 0.3 | 0.3 |
|  |  | EDTA-2-sodium | 0.3 | 0.3 | 0.3 | 0.3 | 0.3 | 0.3 | 0.3 | 0.3 | 0.3 | 0.3 | 0.3 | 0.3 |
|  |  | Pure water | | | | | | balance | | | | | | |
| Second Pack (mass %) | Treatment agent | aqueous 35% hydrogen peroxide | 16.9 | 16.9 | 16.9 | 16.9 | 16.9 | 16.9 | 16.9 | 16.9 | 16.9 | 16.9 | 16.9 | 16.9 |
|  | Surfactant | Ceteareth-13*[1] | 0.5 | 0.5 | 0.5 | 0.5 | 0.5 | 0.5 | 0.5 | 0.5 | 0.5 | 0.5 | 0.5 | 0.5 |
|  |  | Sodium laureth-1 sulfate*[2] | 1.0 | 1.0 | 1.0 | 1.0 | 1.0 | 1.0 | 1.0 | 1.0 | 1.0 | 1.0 | 1.0 | 1.0 |
|  | Oily Agent | Cetyl alcohol | 3.0 | 3.0 | 3.0 | 3.0 | 3.0 | 3.0 | 3.0 | 3.0 | 3.0 | 3.0 | 3.0 | 3.0 |
|  | Others | EDTA-2-sodium | 0.1 | 0.1 | 0.1 | 0.1 | 0.1 | 0.1 | 0.1 | 0.1 | 0.1 | 0.1 | 0.1 | 0.1 |
|  |  | Phosphoric acid | 0.1 | 0.1 | 0.1 | 0.1 | 0.1 | 0.1 | 0.1 | 0.1 | 0.1 | 0.1 | 0.1 | 0.1 |
|  |  | Disodium hydrogenphosphate | 0.2 | 0.2 | 0.2 | 0.2 | 0.2 | 0.2 | 0.2 | 0.2 | 0.2 | 0.2 | 0.2 | 0.2 |
|  |  | Pure water | balance | balance | balance | balance | balance | balance | balance | balance | balance | balance | balance | balance |
| Evaluation Results |  | Smoothness in rinsing | 4.0 | 3.8 | 3.6 | 3.6 | 4.0 | 3.8 | 3.8 | 3.4 | 4.2 | 4.0 | 3.8 | 3.0 |
|  |  | Coated feeling in rinsing | 4.4 | 4.0 | 4.0 | 3.6 | 4.0 | 3.4 | 4.4 | 4.0 | 4.2 | 3.8 | 3.6 | 3.0 |
|  |  | Softness in rinsing | 4.4 | 3.6 | 3.4 | 3.6 | 4.2 | 3.6 | 4.4 | 4.0 | 4.0 | 3.6 | 3.8 | 3.0 |

*[1]Kao's "Emulgen 220"
*[2]Kao's "Emal 170J" (active ingredient 70%)

From Table 7, it is known that the hair bleaches of Examples 74 to 84 gave good smoothness, coated feeling and softness to the treated hair in rinsing.

Example 85 and Comparative Example 10
(Production and Evaluation of Permanent Wave Composition)

(1) Preparation of First Pack

As shown in Table 8, the other components than 50% ammonium thioglycolate and 28% ammonia were mixed with an adequate amount of water and stirred until complete dissolution. 50% ammonium thioglycolate, 28% ammonia and the remaining water were added thereto and stirred for complete dissolution, thereby preparing a first pack. The pH was 9.

(2) Preparation of Second Pack

As shown in Table 8, sodium bromate, propylene glycol, surfactants (ceteareth-13, laureth-3), keratin hydrolyzates and an adequate amount of water were mixed and stirred until complete dissolution. Amodimethicone was added thereto and uniformly mixed to prepare a second pack. The pH was 7.

(3) Evaluation of Permanent Wave Composition

Hair (artificial black hair, BS-B3A) with no chemical treatment history, which is commercially sold by Beaulax and which has a length of 30 cm and a mass of 10 g, was used. 2 g of the hair sample was dressed in a width of 2 cm so as to have a uniform thickness. One end of the hair was fixed to a plastic plate having a width of 2 cm with an adhesive, thereby preparing a test piece of hair tresses.

Thus prepared, the hair tresses were washed with the plain shampoo described in Example 1, then toweled to remove water, and dried with warm air from a drier. The hair tresses were wound around a rod having a diameter of 9 mm (Dariya's Venezel Cold Rod No. 6), then 2 g of the first pack was applied thereto, left as such at 30° C. for 15 minutes, and thereafter the hair was rinsed with warm water for 3 minutes. Further, 2 g of the second pack was applied, left as such at 30° C. for 15 minutes, and the hair was removed from the rod.

Five panelists rinsed the evaluation tresses with warm water for 1 minute, and then evaluated for the smoothness, the coated feeling and the softness in rinsing in the same manner as in Example 1 except that the sample of Comparative Example 10 was taken as the standard criterion. In addition, the tresses were rinsed with a plain conditioner having the composition mentioned below, and evaluated for the finger-combability, the smoothness and the long-lasting smoothness in rinsing.

The permanent wave compositions were evaluated, based on the sample of Comparative Example 10 given a standard score of 3. The results are shown in Table 8.

[Composition of Plain Conditioner]

| (Components) | (%) |
| --- | --- |
| Stearoxypropyltrimethylammonium chloride | 1.0 |
| Cetyl alcohol | 0.6 |
| Stearyl alcohol | 2.3 |
| Propylene glycol | 1.0 |
| Phenoxyethanol | 0.3 |
| Pure water | balance |
| Total | 100.0 |

[Production of Plain Conditioner]

Phenoxyethanol and an adequate amount of water were mixed and heated up to 80° C. To this, added was a mixture prepared by previously mixing stearoxypropyltrimethylammonium chloride, cetyl alcohol, stearyl alcohol and propylene glycol and heating up to 70° C., and emulsified, and then cooled down to room temperature.

(Evaluation Criteria: Based on Comparative Example 10 Given a Standard Score of 3)

The evaluation results made by the five panelists were averaged to be the score of each sample.

Finger-Combability after Treatment with Conditioner

5: Extremely good finger-combability as compared with the permanent wave composition of Comparative Example 10.

4: Good finger-combability as compared with the permanent wave composition of Comparative Example 10.

3: Average (finger-combability after conditioner treatment with the permanent wave composition of Comparative Example 10).

2: Bad finger-combability as compared with the permanent wave composition of Comparative Example 10.

1: Extremely bad finger-combability as compared with the permanent wave composition of Comparative Example 10.

Smoothness after Conditioner Treatment

5: Extremely good Smoothness as compared with the permanent wave composition of Comparative Example 10.

4: Good Smoothness as compared with the permanent wave composition of Comparative Example 10.

3: Average (Smoothness after conditioner treatment with the permanent wave composition of Comparative Example 10).

2: Bad Smoothness as compared with the permanent wave composition of Comparative Example 10.

1: Extremely bad Smoothness as compared with the permanent wave composition of Comparative Example 10.

Long-Lasting Smoothness after Conditioner Treatment

5: Extremely good long-lasting smoothness as compared with the permanent wave composition of Comparative Example 10.

4: Good long-lasting smoothness as compared with the permanent wave composition of Comparative Example 10.

3: Average (long-lasting smoothness after conditioner treatment with the permanent wave composition of Comparative Example 10).

2: Bad long-lasting smoothness as compared with the permanent wave composition of Comparative Example 10.

1: No long-lasting smoothness at all.

TABLE 8

| Permanent Wave Composition | | | Example 85 | Comparative Example 10 |
| --- | --- | --- | --- | --- |
| First Pack (mass %) | Polymer | CCE (20) | 0.5 | |
| | | Cationized hydroxyethyl cellulose*[1] | | 0.5 |
| | Treatment agents (alkali agents) | 50% ammonium thioglycolate | 12.0 | 12.0 |
| | | Ammonium hydrogencarbonate | 2.5 | 2.5 |
| | | 28% ammonia | 1.5 | 1.5 |
| | | Monoethanolamine | 1.0 | 1.0 |
| | Surfactant | Ceteareth-13*[2] | 1.0 | 1.0 |
| | Others | Ethanol | 5.0 | 5.0 |
| | | Propylene glycol | 5.0 | 5.0 |
| | | EDTA-2-sodium | 0.5 | 0.5 |
| | | Pure water | balance | balance |
| Second Pack (mass %) | Treatment agent (oxidizing agent) | Sodium bromate | 7.5 | 7.5 |
| | Surfactant | Ceteareth-13*[2] | 0.8 | 0.8 |
| | | Laureth-3*[3] | 0.3 | 0.3 |
| | Others | Amodimethicone | 0.5 | 0.5 |
| | | Propylene glycol | 5.0 | 5.0 |
| | | Keratin hydrolyzate | 0.1 | 0.1 |
| | | Pure water | balance | balance |
| Evaluation Results | | Smoothness in rinsing | 4.0 | 3.0 |
| | | Coated Feeling in rinsing | 5.0 | 3.0 |
| | | Softness in rinsing | 5.0 | 3.0 |
| | | Finger-Combability in rinsing after conditioner treatment | 5.0 | 3.0 |
| | | Smoothness in rinsing after conditioner treatment | 4.6 | 3.0 |
| | | Long-lasting smoothness in rinsing after conditioner treatment | 5.0 | 3.0 |

*[1]Kao's "POIZ C-80M"
*[2]Kao's "Emulgen 220"
*[3]Kao's "Emulgen 103"

From Table 8, it is known that the permanent wave composition of Example 85 gave good smoothness, coated feeling and softness in treatment and rinsing. In addition, it is also known that the composition also gave good finger-combability, smoothness and long-lasting smoothness in hair rinsing after conditioner treatment.

Example 86 and Comparative Example 11
(Production and Evaluation of Hair Relaxer)

(1) Preparation of First Pack

As shown in Table 9, the other components than 50% ammonium thioglycolate were mixed with an adequate amount of water and stirred until complete dissolution. 50% ammonium thioglycolate and the remaining water were added thereto and stirred for complete dissolution, thereby preparing a first pack. The pH was 9.

Thus prepared, the hair tresses were treated with the same plain shampoo as in Example 1, towel-dried and combed. 1.5 g of the first pack was applied to the hair tresses, then left as such at 25° C. for 15 minutes, thereafter rinsed with warm water for 30 seconds, and towel-dried. Subsequently, the hair tresses were treated with a high-temperature hair iron set at 130° C. Next, 1.5 g of the second pack was applied thereto and left as such at 25° C. for 5 minutes.

Five panelists rinsed the-thus treated hair tresses with warm water for 1 minute, and evaluated them in the same manner as in Example 85 except that the sample of Comparative Example 11 given a standard score 3 was taken as the evaluation criteria, in point of the finger-combability, smootheness and long-lasting smoothness in rinsing after conditioner treatment. The hair relaxer was evaluated, based on the sample of Comparative Example 11 given a standard score of 3. The results are shown in Table 9.

TABLE 9

| Hair Relaxer | | | Example 86 | Comparative Example 11 |
|---|---|---|---|---|
| First Pack (mass %) | Polymer | CCE (20) | 1.0 | |
| | | Cationized hydroxyethyl cellulose*[1] | | 1.0 |
| | Treatment agents | 50% ammonium thioglycolate | 13.0 | 13.0 |
| | | Monoethanolamine | 2.0 | 2.0 |
| | | Ammonium hydrogencarbonate | 2.0 | 2.0 |
| | Others | β-naphthalenesulfonic acid | 2.0 | 2.0 |
| | | Benzyloxyethanol | 3.5 | 3.5 |
| | | Ethanol | 4.0 | 4.0 |
| | | Propylene glycol | 5.0 | 5.0 |
| | | EDTA-2-sodium | 0.5 | 0.5 |
| | | Pure water | Balance | balance |
| Second Pack (mass %) | Treatment agents | 35% hydrogen peroxide | 5.0 | 5.0 |
| | | Aqueous 48% sodium hydroxide solution | 0.1 | 0.1 |
| | Surfactant | Ceteareth-13*[2] | 1.0 | 1.0 |
| | Others | Lactic acid | 4.5 | 4.5 |
| | | β-naphthalenesulfonic acid | 1.5 | 1.5 |
| | | Benzyloxyethanol | 3.5 | 3.5 |
| | | Ethanol | 10.0 | 10.0 |
| | | Pure water | Balance | balance |
| Evaluation Results | | Smoothness in rinsing | 5.0 | 3.0 |
| | | Coated feeling in rinsing | 5.0 | 3.0 |
| | | Softness in rinsing | 5.0 | 3.0 |
| | | Finger-combability in rinsing after conditioner treatment | 4.0 | 3.0 |
| | | Smoothness in rinsing after conditioner treatment | 5.0 | 3.0 |
| | | Long-lasting smoothness in rinsing after conditioner treatment | 5.0 | 3.0 |

*[1]Kao's "POIZ C-80M"
*[2]Kao's "Emulgen 220"

(2) Preparation of Second Pack

As shown in Table 9, Lactic acid, β-naphthalenesulfonic acid, benzyloxyethanol, ethanol, ceteareth-13 and an adequate amount of water were mixed and stirred until complete dissolution. Next, an aqueous 48% sodium hydroxide solution was added thereto, stirred and mixed. Further, aqueous 35% hydrogen peroxide and the remaining water were added and stirred until complete dissolution to prepare a second pack. The pH was 3.

(3) Evaluation of Hair Relaxer

Unruly hair tresses provided by a Japanese adult woman, having a length of 26 cm and a mass of 10 g, were tested here as a sample. This was treated with the same plain shampoo as in Example 1, rinsed with running water and air-dried. 2 g of the sample hair tresses were trimmed to have a uniform thickness and a width of 2 cm. One end of the sample was fixed to a plastic board having a width of 2 cm with an adhesive, thereby preparing test hair tresses.

From Table 9, it is known that the hair relaxer of Example 86 gave good smoothness, coated feeling and softness in treatment and rinsing. In addition, it is also known that the hair relaxer also gave good finger-combability, smoothness and long-lasting smoothness in hair rinsing after conditioner treatment.

Examples 87 to 99, Comparative Example 12
(Production and Evaluation of Hair Shampoo)

In the same manner as in Examples 18 to 29 but using any of CCE (12) and (20) and cationized guar gum, hair shampoos were prepared to have the composition shown in Table 10.

Artificial hair tresses (20 g, 20 cm) were washed with the plain shampoo described in Example 1, then well wetted with warm water at 35 to 40° C., and 0.5 g of the shampoo of Examples 87 to 99 and Comparative Example 12 was applied thereto and washed for 1 minute. Subsequently, the hair tresses were rinsed with warm water for 30 seconds, toweled to remove water, then combed, and further dried with warm air from a drier, and finally combed.

Five panelists evaluated the hair in point of the finger-combability in hair washing, the smoothness and the long-lasting smoothness in rinsing, and the most feeling and the uniformity after drying, according to the evaluation criteria and the evaluation methods mentioned below.
(Evaluation Criteria, Evaluation Methods)
Finger-Combability in Washing
  5: Extremely good finger-combability as compared with the hair shampoo of Comparative Example 12.
  4: Good finger-combability as compared with the hair shampoo of Comparative Example 12.
  3: Average (finger-combability in rinsing with the hair shampoo of Comparative Example 12).
  2: Bad finger-combability as compared with the hair shampoo of Comparative Example 12.
  1: Extremely bad finger-combability as compared with hair shampoo of Comparative Example 12.
Smoothness in Rinsing
  5: Extremely good smoothness as compared with hair shampoo of Comparative Example 12.
  4: Good smoothness as compared with the hair shampoo of Comparative Example 12.
  3: Average (smoothness in rinsing with the hair shampoo of Comparative Example 12).
  2: Bad smoothness as compared with the hair shampoo of Comparative Example 12.
  1: Extremely bad smoothness as compared with the hair shampoo of Comparative Example 12.
Long-Lasting Smoothness
  5: Extremely good long-lasting smoothness as compared with the hair shampoo of Comparative Example 12.
  4: Good long-lasting smoothness as compared with the hair shampoo of Comparative Example 12.
  3: Average (long-lasting smoothness with the hair shampoo of Comparative Example 12).
  2: Bad long-lasting smoothness as compared with the hair shampoo of Comparative Example 12.
  1: Extremely bad long-lasting smoothness as compared with the hair shampoo of Comparative Example 12.
Moist Feeling after Drying
  5: Extremely good moist feeling as compared with the hair shampoo of Comparative Example 12.
  4: Good moist feeling as compared with the hair shampoo of Comparative Example 12.
  3: Average (moist feeling after drying with the hair shampoo of Comparative Example 12).
  2: Bad moist feeling as compared with the hair shampoo of Comparative Example 12.
  1: Extremely bad moist feeling as compared with the hair shampoo of Comparative Example 12.
Uniformity after Drying
  5: Extremely good uniformity as compared with the hair shampoo of Comparative Example 12.
  4: Good uniformity as compared with the hair shampoo of Comparative Example 12.
  3: Average (uniformity after drying with the hair shampoo of Comparative Example 12).
  2: Hair tips scattering as compared with the hair shampoo of Comparative Example 12.
  1: Noticeable hair tips scattering as compared with the hair shampoo of Comparative Example 12.

TABLE 10

| | | Hair Wash Composition (hair shampoo) | 87 | 88 | 89 | 90 | 91 | 92 | 93 | 94 | 95 | 96 | 97 | 98 | 99 | Comparative Example 12 |
|---|---|---|---|---|---|---|---|---|---|---|---|---|---|---|---|---|
| Composition (part by mass) | Polymer | CCE (12) | | | | | 0.3 | | | | | | 0.3 | | | |
| | | CCE (20) | 0.3 | 0.3 | 0.3 | | 0.3 | 0.3 | 0.3 | 0.3 | 0.3 | 0.3 | | 0.3 | 0.3 | |
| | | Cationized guar gum*1 | | | | | | | | | | | | | | 0.3 |
| | Surfactant | Internal olefinsulfonate (1) | 10.0 | | | 8.0 | 8.0 | 8.0 | 12.0 | | | | | | | |
| | | Internal olefinsulfonate (2) | | 10.0 | | 2.0 | 2.0 | 2.0 | 3.0 | | | | | | | |
| | | Internal olefinsulfonate (3) | | | | | | | | 10.0 | | | | | | |
| | | Internal olefinsulfonate (4) | | | | | | | | | 10.0 | | 8.0 | 8.0 | 8.0 | 12.0 | |
| | | Internal olefinsulfonate (5) | | | | | | | | | | 10.0 | 2.0 | 2.0 | 2.0 | 3.0 | |
| | | Sodium laureth(2) sulfate*2 | | | | | | | | | | | | | | 10.0 |
| | | coconut oil fatty acid amide propylbetaine*3 | 2.0 | 2.0 | 2.0 | 2.0 | | 2.0 | 2.0 | 2.0 | 2.0 | 2.0 | 2.0 | | 2.0 | 2.0 |
| | | Lauryl-dimethyl-aminoacetate betaine*4 | | | | | 2.0 | | | | | | | 2.0 | | |
| | | coconut oil fatty acid mono-ethanolamide *5 | 0.3 | 0.3 | 0.3 | 0.3 | 0.3 | 0.3 | 0.3 | 0.3 | 0.3 | 0.3 | 0.3 | 0.3 | 0.3 | 0.3 |
| | Oily Agent | High-polymerized dimethylsiloxane*6 | 2.0 | 2.0 | 2.0 | 2.0 | 2.0 | 2.0 | 2.0 | 2.0 | 2.0 | 2.0 | 2.0 | 2.0 | 2.0 | 2.0 |
| | Others | Pearl agent*7 | | | | | | | adequate dose | | | | | | | |
| | | pH regulator | | | | | | | adequate dose | | | | | | | |
| | | Pure water | | | | | | | Balance | | | | | | | |
| Evaluation | | Finger-combability in washing | 4.4 | 3.4 | 4.8 | 4.4 | 4.8 | 5.0 | 4.0 | 4.6 | 3.4 | 5.0 | 4.4 | 4.4 | 5.0 | 3.0 |
| | | Smoothness in rinsing | 4.4 | 3.6 | 4.4 | 4.0 | 4.2 | 4.0 | 4.2 | 4.4 | 4.6 | 4.8 | 4.0 | 4.0 | 4.4 | 3.0 |

TABLE 10-continued

| Hair Wash Composition (hair shampoo) | 87 | 88 | 89 | 90 | 91 | 92 | 93 | 94 | 95 | 96 | 97 | 98 | 99 | Comparative Example 12 |
|---|---|---|---|---|---|---|---|---|---|---|---|---|---|---|
| Long-lasting smoothness in rinsing | 4.8 | 4.0 | 4.8 | 4.2 | 4.8 | 4.0 | 4.8 | 4.6 | 4.6 | 4.8 | 4.2 | 4.8 | 4.4 | 3.0 |
| Moist feeling after drying | 4.6 | 3.4 | 4.6 | 4.8 | 4.8 | 4.6 | 4.6 | 4.2 | 4.2 | 4.2 | 4.2 | 4.6 | 4.4 | 3.0 |
| Uniformity after drying | 4.6 | 3.6 | 4.6 | 4.6 | 4.4 | 4.6 | 4.0 | 4.6 | 4.6 | 4.8 | 4.0 | 4.8 | 4.6 | 3.0 |

*1 Rhodia's (Jaguar C-13S" (active ingredient 100%)
*2 Kao's "Emal 270J" (active ingredient 70%)
*3 Kao's "Amphitol 55AB" (active ingredient 30%)
*4 Kao's "Amphitol 20BS" (active ingredient 31%)
*5 Kawaken Fine Chemical's "Amizol CME"
*6 Toray Dow Coming's "BY22-029" (active ingredient 50%)
*7 Kao's "Pearl Concentrate SA-M2" (active ingredient 20%)

From Table 10, it is known that the hair shampoos of Examples 87 to 99 are excellent hair shampoos capable of providing good finger-combability in hair washing, good smoothness and long-lasting smoothness in rinsing, and good moist feeling and uniformity after drying.

INDUSTRIAL APPLICABILITY

When incorporated in a hair wash composition such as hair shampoo or the like, the cationic group-containing cellulose ether of the present invention can provide foam softness, good finger-combability and hair softness in washing, excellent smoothness, long-lasting smoothness, softness and coated feeling in hair rinsing, and moist feeling and uniformity after drying. When incorporated in a skin cleanser composition such as body wash, face wash or the like, the cationic group-containing cellulose ether can provide excellent moisturizing feeling in skin washing. When incorporated in a hair conditioner composition, the cationic group-containing cellulose ether can provide good presence in application, excellent smoothness, long-lasting smoothness and softness in rising, and excellent coated feeling after drying. In addition, when incorporated in a hair treatment composition, the cationic group-containing cellulose ether can provide good smoothness, coated feeling and softness to the hair in rinsing after treatment.

The invention claimed is:

1. A cationic group-containing cellulose ether, which has a main chain derived from an anhydroglucose represented by the following general formula (1), and in which the degree of substitution with a cationized oxyalkylene group per the anhydroglucose unit is from 0.01 to 1.0, the degree of substitution with a glycerol group is from 0.5 to 5.0, and the degree of substitution with a group that contains a branched hydrocarbon group having from 8 to 18 carbon atoms and is represented by any of the following general formulae (6) to (8) is from 0.001 to 0.2:

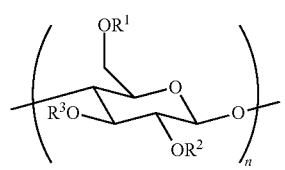

(1)

wherein $R^1$, $R^2$ and $R^3$ each independently represent a substituent comprising at least one structural unit selected from the following formulae (2) to (8), or a hydrogen atom; n indicates a mean degree of polymerization of the anhydroglucose-derived main chain, and is a number of from 100 to 12000,

[Chem. 2]

(2)

(3)

(4)

(5)

(6)

(7)

(8)

wherein the structural unit represented by the formula (2) or (3) is a cationized oxyalkylene group; the structural unit represented by the formula (4) or (5) is a glycerol group; and the structural unit represented by any of the formulae (6) to (8) is a group that contains a branched hydrocarbon group having from 8 to 18 carbon atoms; $R^4$ to $R^9$ each independently represent a linear or branched alkyl group having from 1 to 3 carbon atoms; $X^-$ and $Y^-$ each represent an anion; and r and s each indicate an integer of from 0 to 3; $R^{10}$ and $R^{11}$ each independently represent a branched hydrocarbon group having from 6 to 16 carbon atoms; $R^{12}$ represents a branched hydrocarbon group having from 8 to 18 carbon atoms; and p indicates an integer of 0 or 1; and, in the structural unit represented by any of the formulae (2) to (7), the oxygen atom bonds to a hydrogen atom or to the carbon atom of the above-mentioned structural unit.

2. The cationic group-containing cellulose ether according to claim 1, of which the cation charge density is from 0.05 mmol/g to 2.0 mmol/g.

3. A surfactant composition comprising the cationic group-containing cellulose ether of claim 1, a surfactant and water.

4. The surfactant composition according to claim 3, wherein the content of the cationic group-containing cellulose ether is from 0.01% by mass to 10% by mass.

5. The surfactant composition according to claim 3, wherein the ratio by mass of the cationic group-containing cellulose ether to the surfactant is from 0.0002 to 10.

6. The surfactant composition according to claim 3, wherein the content of the surfactant is from 0.01% by mass to 80% by mass.

7. The surfactant composition according to claim 3, wherein the degree of substitution with a cationized oxyalkylene group in the cationic group-containing cellulose ether is from 0.03 to 0.9, the degree of substitution with a glycerol group is from 0.5 to 3.0, and the degree of substitution with a hydrocarbon group-containing group is from 0.001 to 0.1.

8. A hair wash composition comprising the cationic group-containing cellulose ether of claim 1, a surfactant and water.

9. A skin cleanser composition comprising the cationic group-containing cellulose ether of claim 1, a surfactant and water.

10. A hair conditioner composition comprising the cationic group-containing cellulose ether of claim 1, a surfactant, an oily agent and water.

11. A hair treatment composition comprising the cationic group-containing cellulose ether of claim 1, as well as at least one treatment agent selected from a hair-coloring dye, an oxidizing agent, an alkali agent, and a keratin-reducing agent.

12. A method of washing hair, comprising washing hair with the composition comprising the cationic group-containing cellulose ether of claim 1, a surfactant and water, then rinsing and drying the hair.

13. A method of cleansing a skin, comprising washing a skin with the composition comprising the cationic group-containing cellulose ether of claim 1, a surfactant and water, then rinsing and drying the skin.

14. A method of conditioning hair, comprising washing hair with a detergent, and then applying the composition comprising the cationic group-containing cellulose ether of claim 1, a surfactant, an oily agent and water to the hair.

15. A method of treating hair, comprising treating hair with the composition comprising the cationic group-containing cellulose ether of claim 1, as well as at least one treatment agent selected from a hair-coloring dye, an oxidizing agent, an alkali agent, and a keratin-reducing agent, then rinsing and drying the hair.

* * * * *